United States Patent
Sarpotdar et al.

(12) 
(10) Patent No.: US 11,517,560 B2
(45) Date of Patent: *Dec. 6, 2022

(54) STABILIZED OXYMETAZOLINE FORMULATIONS AND THEIR USES

(71) Applicant: EPI Health, LLC, Charleston, SC (US)

(72) Inventors: Pramod Sarpotdar, Rohnert Park, CA (US); Kevin Warner, Anaheim, CA (US); Steven Zhang, Newton, MA (US); Gurpreet Ahluwalia, Tustin, CA (US); Amy Kuang, Irvine, CA (US)

(73) Assignee: EPI HEALTH, LLC, Charleston, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/924,782

(22) Filed: Jul. 9, 2020

(65) Prior Publication Data

US 2021/0169855 A1 Jun. 10, 2021

Related U.S. Application Data

(60) Continuation of application No. 16/380,538, filed on Apr. 10, 2019, now Pat. No. 10,751,325, which is a continuation of application No. 15/984,918, filed on May 21, 2018, now Pat. No. 10,335,391, which is a continuation of application No. 15/429,873, filed on Feb. 10, 2017, now Pat. No. 9,974,773, which is a division of application No. 14/737,360, filed on Jun. 11, 2015, now Pat. No. 9,801,857.

(60) Provisional application No. 62/069,624, filed on Oct. 28, 2014, provisional application No. 62/010,838, filed on Jun. 11, 2014.

(51) Int. Cl.

| *A61K 31/4164* | (2006.01) |
| *A61K 9/00* | (2006.01) |
| *A61K 47/14* | (2017.01) |
| *A61K 9/06* | (2006.01) |
| *A61K 9/107* | (2006.01) |
| *A61K 47/18* | (2017.01) |
| *A61K 31/4174* | (2006.01) |
| *A61K 47/10* | (2017.01) |
| *A61K 47/12* | (2006.01) |
| *A61K 47/44* | (2017.01) |

(52) U.S. Cl.

CPC ........ *A61K 31/4164* (2013.01); *A61K 9/0014* (2013.01); *A61K 9/06* (2013.01); *A61K 9/107* (2013.01); *A61K 31/4174* (2013.01); *A61K 47/10* (2013.01); *A61K 47/12* (2013.01); *A61K 47/14* (2013.01); *A61K 47/183* (2013.01); *A61K 47/44* (2013.01)

(58) Field of Classification Search
CPC .............. A61K 31/4174; A61K 31/4164
See application file for complete search history.

(56) References Cited

U.S. PATENT DOCUMENTS

| 3,147,275 | A | 9/1964 | Fruhstorfer et al. |
| 6,420,688 | B1 | 7/2002 | Emmerich et al. |
| 6,433,024 | B1 | 8/2002 | Popp et al. |
| 6,960,615 | B2 | 11/2005 | Glassman et al. |
| 7,439,241 | B2 | 10/2008 | DeJovin et al. |
| 7,812,049 | B2 | 10/2010 | Shanler et al. |
| 8,815,929 | B2 | 8/2014 | Shanler et al. |
| 9,801,857 | B2 * | 10/2017 | Sarpotdar .......... A61K 31/4164 |
| 9,974,773 | B2 * | 5/2018 | Sarpotdar .......... A61K 31/4174 |
| 10,335,391 | B2 * | 7/2019 | Sarpotdar ............ A61K 47/183 |
| 10,751,325 | B2 * | 8/2020 | Sarpotdar .............. A61K 47/44 |
| 2003/0108496 | A1 | 6/2003 | Yu et al. |
| 2005/0165079 | A1 | 7/2005 | Shanler et al. |
| 2008/0193551 | A1 | 8/2008 | De Waard et al. |
| 2009/0130027 | A1 | 5/2009 | Shanler et al. |
| 2012/0149748 | A1 | 6/2012 | Shanler et al. |
| 2012/0208858 | A1 | 8/2012 | Shanler et al. |
| 2013/0079379 | A1 | 3/2013 | Shanler et al. |

FOREIGN PATENT DOCUMENTS

| WO | WO-2007000192 A1 | 1/2007 |
| WO | WO-2012075319 A2 | 6/2012 |

OTHER PUBLICATIONS

Afrin Original—Oxymetazoline Hydrochloride Spray Product Label, Bayer Healthcare LLC, Feb. 2017.
Bechtel et al. "Rosacea: Choosing Among the Topical and Systemic Therapeutic Options" Dec. 2011, Practical Dermatology 45-48.
Berge et al. "Pharmaceutical Salts" Jan. 1977, J. Pharma. Sci. 66(1):1-18.
Blount et al. "Rosacea: A Common, Yet Commonly Overlooked, Condition" Aug. 1, 2002, American Family Physician, 66(3):435-440.
Ghosh et al. "Transdermal and Topical Drug Delivery Systems," Chapter 14 1997 Interpharm Press.
Gould Salt Selection for Basic Drugs, 1986, Intl. J. Pharmac. 33:201-217.
Guarrera et al. "Flushing in Rosacea: A Possible Mechanism" 1982, Archives Dermatol Res. 272:311-316.
Guimaraes et al. "Vascular Adrenoceptors: An Update" Jun. 2001, Pharmacol Rev. 53(2):319-356.

(Continued)

Primary Examiner — Rei Tsang Shiao
(74) Attorney, Agent, or Firm — Blank Rome LLP

(57) ABSTRACT

The present invention provides stabilized cream formulations of oxymetazoline and uses thereof. The present invention also provides a method of treating facial erythema associated with rosacea in a patient in need of such treatment, comprising topically administering once or twice daily to the site of erythema on the face of the patient a pharmaceutical composition comprising 0.5%, 1.0% or 1.5% oxymetazoline or a pharmaceutically acceptable salt thereof as the sole active ingredient.

17 Claims, 3 Drawing Sheets

(56) References Cited

OTHER PUBLICATIONS

Jarajapu et al. "Functional Characterization of alpha1-Adrenoceptor Subtypes in Human Subcutaneous Resistance Arteries" Nov. 2001, J Pharmacol Exp Ther 299(2):729-734.
McClellan et al. "Topical Metronidazole: A Review of its Use in Rosacea" May-Jun. 2000, Am. J. Clin. Dermatol. 1 (3):191-199.
Piascik et al. "alpha1-Adrenergic Receptors: New Insights and Directions" Aug. 2001, J Pharmacol Exp Ther. 298 (2):403-410.
Rebora "The Management of Rosacea" 2002, American Journal of Clinical Dermatology 3(7):489-496.
Ruffolo et al. "Receptor Interactions of Imidazolines, IX. Cirazoline is an Alpha-1 Adrenergic Agonist and an Alpha-2 Adrenergic Antagonist" Jul. 1982, J. Pharmacol. Exp. Ther. 222(1):29-36.
Scholz "Imidazole Derivatives With Sympathomimetic Activity" Feb. 1, 1945, Ind. Eng. Chem. 37(2):120-125.
Shanler et al. Successful Treatment of the Erythema of Flushing of Rosacea Using a Topically Applied Selective ?1 Adrenergic Receptor Agonist, Oxymetazoline Nov. 2007, Arch Dermatol. 143(11):1369-1371.
Tan et al. "Rosacea and Migraine" Jan. 3, 1976, British Medical Journal 1 (6000):21.

\* cited by examiner

STABILIZED OXYMETAZOLINE FORMULATIONS AND THEIR USES

CROSS-REFERENCE TO RELATED APPLICATIONS

This application is a continuation of U.S. patent application Ser. No. 16/380,538, filed Apr. 10, 2019, which is a continuation of U.S. patent application Ser. No. 15/984,918, filed May 21, 2018, now U.S. Pat. No. 10,335,391, which is a continuation of U.S. patent application Ser. No. 15/429,873 filed on Feb. 10, 2017, now U.S. Pat. No. 9,974,773, which is a divisional of U.S. patent application Ser. No. 14/737,360 filed on Jun. 11, 2015, now U.S. Pat. No. 9,801,857, which claims the benefit of U.S. Provisional Application Ser. No. 62/010,838 filed on Jun. 11, 2014 and U.S. Provisional Application Ser. No. 62/069,624 filed on Oct. 28, 2014, all of which are incorporated by reference herein in their entirety.

FIELD OF THE INVENTION

The present invention is directed to stabilized cream formulations of oxymetazoline and uses thereof.

BACKGROUND

Oxymetazoline and its use for the treatment of skin diseases and disorders, including rosacea, is described in U.S. Pat. Nos. 7,812,049 and 8,883,838, the entireties of which are hereby incorporated by reference. Oxymetazoline is an alpha-2 adrenergic agonist currently being investigated for the treatment of the erythematous component of rosacea. Due to the high ionic strength of the formulation imparted by the presence of oxymetazoline, creating a stable, efficacious, and cosmetically elegant formulation is difficult.

Rosacea is a chronic disease most commonly characterized by facial erythema (redness). There are at least four identified rosacea subtypes and patients may have more than one subtype present. The four most well recognized subtypes are erythematotelangiectatic rosacea (ETR); papulopustular rosacea; phymatous rosacea; and ocular rosacea. Other less common forms exist and the signs and symptoms of each subtype are not unique to that subtype and may overlap or coexist with any of the manifestations of any other subtype. ETR may be characterized by transient and/or permanent erythema with a tendency to flush and blush easily and telangiectasias, which in its milder form may resemble or present as erythema (redness) and in its more pronounced state may manifest as discrete visible blood vessels on the surface of the skin. Papulopustular rosacea may be characterized by transient and/or permanent erythema with papules (red bumps) and pustules (pus filled bumps). Without wishing to be bound by theory, though the papules and other inflammatory lesions (e.g. pustules) of papulopustular rosacea may be mistaken for acne, it is believed that the papules and pustules of rosacea are different from the papules and pustules of acne and arise from different underlying pathophysiologic processes. Phymatous rosacea may be characterized by thickening skin, irregular surface nodularities, enlargement of facial areas (e.g. nose and cheeks), erythema and telangiectasias. Ocular rosacea may be characterized by red, dry and irritated eyes and eyelids. In each subtype, erythema and telangiectasias of varying degree may be a feature.

Rosacea patients may need topical or oral (systemic) medication to alleviate their distress; however, a patient's skin may be so sensitive that many products are irritating and, in fact, may exacerbate the symptoms of rosacea and may cause more redness and discomfort than patients can tolerate. Thus, rosacea can be very difficult to effectively treat and thus may not only be physically distressing but also psychologically distressing. Accordingly, there is a need for a cosmetically and pharmaceutically acceptable therapeutic which addresses the myriad manifestations of rosacea including, but not limited to, the erythema or redness associated with rosacea and the telangiectasias associated with rosacea. Additionally, there is a need for a cosmetically and pharmaceutically acceptable therapeutic which addresses the inflammatory lesions and manifestations associated with rosacea including the papules, pustules and phymas (skin thickening).

There exists a need for improved stabilized cream formulations of oxymetazoline that are effective and well tolerated after topical administration to human patients.

SUMMARY OF THE INVENTION

The present invention provides stabilized cream formulations of oxymetazoline and uses thereof. The present invention also provides a method of treating facial erythema associated with rosacea in a patient in need of such treatment, comprising topically administering once or twice daily to the site of erythema on the face of the patient a pharmaceutical composition comprising 0.5%, 1.0% or 1.5% oxymetazoline or a pharmaceutically acceptable salt thereof as the sole active ingredient.

Figure 1:
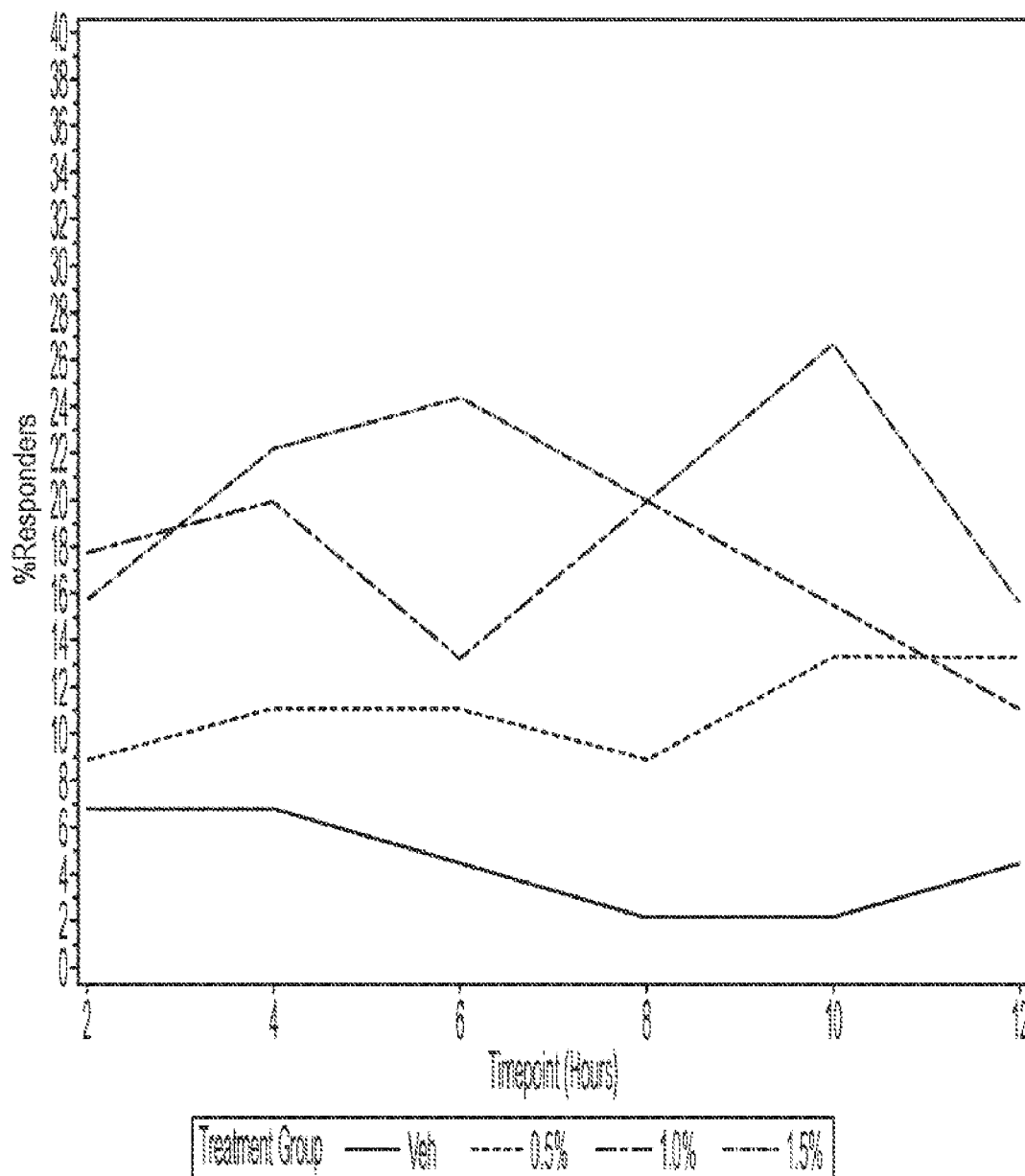
FIG. 1 shows Treatment Response Over 12 Hours on Day 28 (mITT Population)—Twice daily Dosing.
Figure 2:
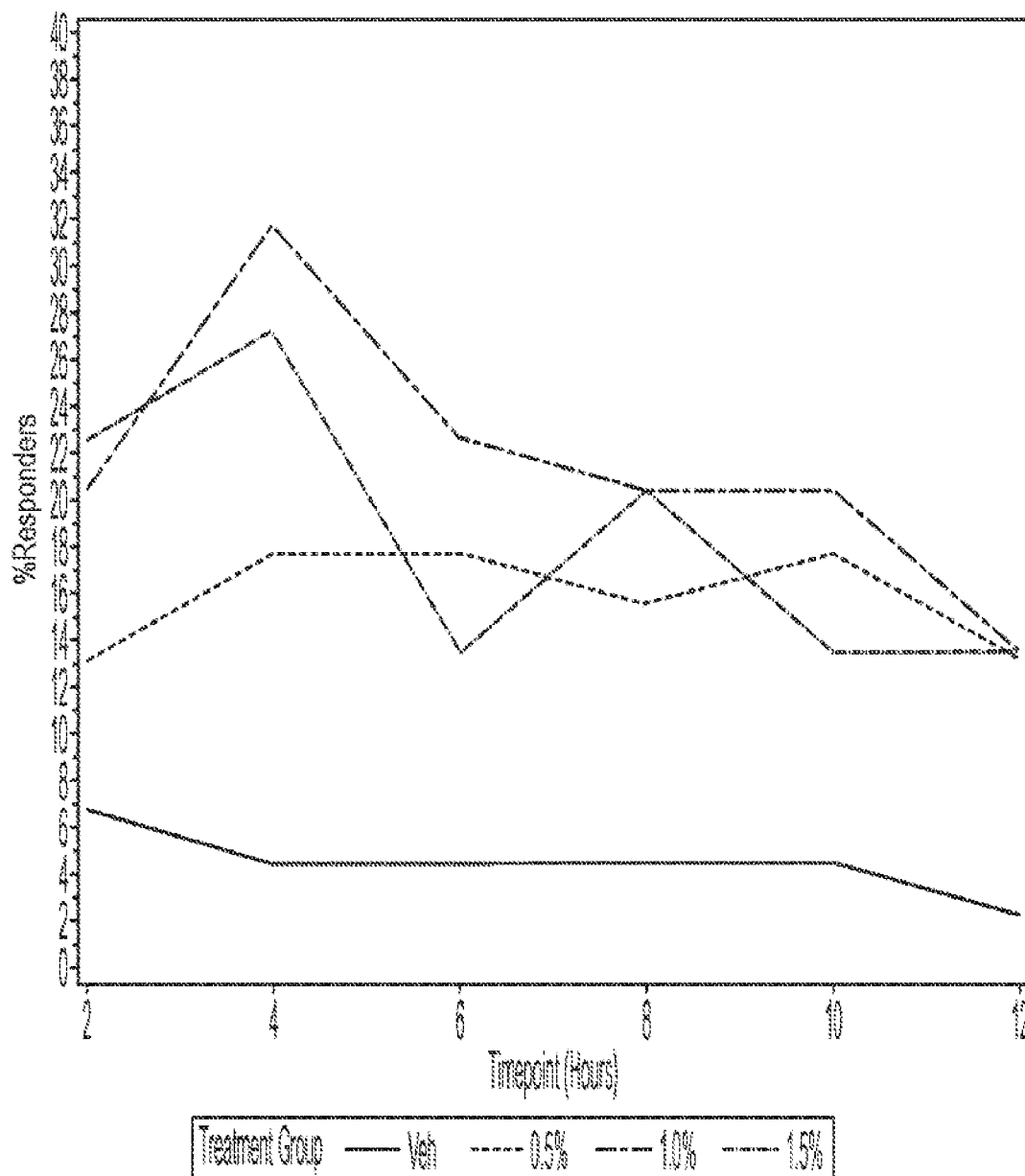
FIG. 2 shows Treatment Response Over 12 Hours on Day 28 (mITT Population)—Once daily Dosing.

Note: For both FIGS. 1 and 2, a treatment response was defined as a ≥2-grade decrease (improvement) from baseline on both Clinician's Erythema Assessment and SSA=Subject Self-Assessment of Erythema.

DETAILED DESCRIPTION OF THE INVENTION

Oxymetazoline HCl is an alpha-2 adrenergic agonist currently being investigated for the treatment of the erythematous component of rosacea. Due to the high ionic strength of the formulation imparted by the presence of oxymetazoline, creating a stable, efficacious, and cosmetically elegant formulation is difficult. Provided herein is a unique, stable formulation composition that facilitates delivery of oxymetazoline into and through the skin. Formulation composition disclosed comprises the following unique properties:

1) Complex oil phase (multiple excipients with varied physical/chemical properties and high concentration of about 23%) and an ionic API (oxymetazoline). The combination of a complex oil phase and ionic API factors pose an unique challenge to develop a physically stable, efficacious formulation.

2) Complex oil phase comprises a minimum viscosity. An oil phase with a minimum viscosity is required to support stabilizing the cream.
3) A complex oil phase that supports increased oxymetazoline flux (and therefore greater expected efficacy) relative to gel and creams with simple or no oil phase.

As provided herein, the terms "therapeutically effective" or "effective" may be used interchangeably and refer to an amount of a therapeutic composition of embodiments of the present invention (e.g., a composition comprising oxymetazoline). For example, a therapeutically effective amount of a composition is an amount of the composition, and particularly the active ingredient, such as oxymetazoline, that generally achieves the desired effect.

A "therapeutically effective amount" or "effective amount" of a composition is an amount necessary or sufficient to achieve the desired result. The activity contemplated by the embodiments herein includes medically therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. However, the effective amount administered can be determined by the practitioner or manufacturer or patient in light of the relevant circumstances including the condition to be treated, the choice of compound to be administered, and the chosen route of administration, and therefore, the above dosage ranges are not intended to limit the scope of the invention in any way. A therapeutically effective amount of the compound of embodiments herein is typically an amount such that when it is administered in a physiologically tolerable excipient composition, it is sufficient to achieve an effective systemic concentration or local concentration in or on the tissue to achieve the desired therapeutic or clinical outcome.

The terms "treat," "treated," or "treating" as used herein refers to therapeutic treatment and/or prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects.

As used herein, the term "consists of" or "consisting of" means that the formulation includes only the elements, steps, or ingredients specifically recited in the particular claimed embodiment or claim.

As used herein, the term "consisting essentially of" or "consists essentially of" means that the only active pharmaceutical ingredient in the formulation or method that treats the specified condition (e.g. erythema or redness associated with the particular disease to be treated) is the specifically recited therapeutic in the particular embodiment or claim.

The term "about" as used herein includes a 5%, 10%, 20%, 30%, 40%, 50%, 60%, 70%, 80%, 90% or 100% deviation above or below the given value. For an amount of an active ingredient in a pharmaceutical formulation provided herein, the term "about" refers to a 5%, 10%, 20% or 30% deviation above or below the given value. For example, an amount of an active ingredient in a pharmaceutical formulation given as "about 1.0% w/w" includes a range of 0.95% to 1.05% w/w, 0.9% to 1.1% w/w, 0.8% to 1.2% w/w, or 0.7% to 1.3% w/w. For an amount of an inactive ingredient or excipient in a pharmaceutical formulation provided herein, the term "about" refers to a 5%, 10%, 20%, 30%, 40%, 50%, 60%, 70%, 80%, 90% or 100% deviation above or below the given value. One skilled in the art is able to determine reasonable deviations based on the specific value evaluated.

As used herein, the term "erythema" refers to any redness of the skin due to hyperemia, congestion of the vasculature or dilation of the vasculature of the skin and its surrounding structures. Erythema may occur in many conditions of the skin including, but not limited to, rosacea and symptoms associated with rosacea, including, for example, papules, pustules, phymas (skin thickening), telangiectasias or erythema associated with rosacea, other skin erythemas, telangiectasias, purpura or the like, and other manifestations associated therewith; other inflammatory conditions of the skin as provided herein.

The term "salt(s)", as employed herein, denotes acidic salts formed with inorganic and/or organic acids, as well as basic salts formed with inorganic and/or organic bases. In addition, when a compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts may be formed, for example, by reacting the free form of a compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartrates, thiocyanates, toluenesulfonates (also known as tosylates) and the like.

Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

In an especially preferred embodiment, the pharmaceutically acceptable salt is a hydrochloride salt, i.e., the compound of the present composition is oxymetazoline hydrochloride.

In some embodiments, the stabilized cream formulations provided herein may be used in a method of treating a skin condition, including, but not limited to, rosacea, including, for example, erythematotelangiectatic rosacea, papulopustular rosacea, phymatous rosacea, ocular rosacea or combinations thereof; and symptoms associated with rosacea, including, for example, papules, pustules, phymas (skin thickening), telangiectasias or erythema associated with rosacea, other skin erythemas, telangiectasias, purpura or the like, and other manifestations associated therewith; other inflammatory conditions of the skin including, but not limited to, keratosis pilaris, lupus miliaris disseminatus faciei, eczema, dermatitis, such as contact dermatitis, atopic dermatitis, seborrheic dermatitis, nummular dermatitis, generalized exfoliative dermatitis, stasis dermatitis, neurodermatitis, lichen simplex chronicus, xerosis and xerotic dermatitis, dyshidrosis and dyshidrotic dermatitis, asteatotic dermatitis or other conditions characterized by sensitive skin or a disturbance of the epidermal barrier; disorders characterized by rough, dry, cracked or fissured skin, disorders characterized by hyperkeratotic skin such as keratodermas and ichthyosis and ichthyosiform dermatoses; disorders of hair follicles and sebaceous glands, such as acne, perioral dermatitis, and pseudofolliculitis barbae; disorders of sweat glands, such as miliaria, including, but not limited to, miliaria crystallina, miliaria rubra, miliaria profunda, miliaria pustulosa; sunburn, chronic actinic damage, poikiloderma, radiation dermatitis, actinic purpura ("solar purpura"); other inflammatory dermatoses, reactions and conditions of the skin, including, but not limited to, psoriasis, drug eruptions, erythema multiforme, erythema nodosum, and granuloma annulare; diseases and conditions characterized by bleeding or bruising such as petechiae, ecchymosis, purpura and the like including any accumulation of blood in the skin due to vascular extravasation, irrespective of size or cause, bleeding or bruising due to any skin injury which may include any trauma including surgical or procedural trauma; infection, inflammatory dermatoses or inflammation due to any cause or combinations thereof comprising administering a cream formulation provided herein.

Example 1: Stabilized Oxymetazoline HCl Cream Formulations

The stabilized cream formulations of oxymetazoline HCl have the following unique properties:
1) Complex oil phase (multiple excipients with varied physical/chemical properties and high concentration of about 23%) and an ionic API (oxymetazoline). The combination of a complex oil phase and ionic API factors pose an unique challenge to develop a physically stable, efficacious formulation.
2) Complex oil phase comprises a minimum viscosity. An oil phase with a minimum viscosity is required to support stabilizing the cream.
3) A complex oil phase that supports increased oxymetazoline flux (and therefore greater expected efficacy) relative to gel and creams with simple or no oil phase.

Each of the tested formulations contain a complex oil phase (multiple excipients with varied physical/chemical properties and high concentration of about 23%) and an ionic API (oxymetazoline). The combination of a complex oil phase and ionic API posed a unique challenge to develop a physically stable formulation that maintained good efficacy at the given concentration of API. The formulations of Table 1 below were found to have good physical stability thereby predicting good shelf life as a commercial topical drug product.

TABLE 1

Exemplary formulations evaluated for physical stability

| | | Example | | | |
|---|---|---|---|---|---|
| | | 1 | 2 | 3 | 4 |
| Function | Ingredient | % w/w | | | |
| Active | Oxymetazoline HCl | 1.5 | 1.5 | 1.0 | 0.5 |
| Preservative | Methylparaben | 0.2 | 0.2 | 0.2 | 0.2 |
| | Propylparaben | 0.05 | 0.05 | 0.05 | 0.05 |
| | Phenoxyethanol | 0.8 | 0.8 | 0.8 | 0.8 |
| Buffer | Sodium citrate, dihydrate | 0.3 | 0.7 | 0.3 | 0.3 |
| | Citric acid, anhydrous | 0.219 | — | 0.219 | 0.219 |
| Chelating Agent | Edetate, disodium | 0.01 | — | 0.01 | 0.01 |
| Antioxidant | BHT | 0.05 | — | 0.05 | 0.05 |
| Oil Phase | Lanolin, anhydrous | 2 | — | 2 | 2 |
| | Medium chain triglycerides | 7 | 2 | 7 | 7 |
| | Diisopropyl adipate | 7 | 7 | 7 | 7 |
| | Oleyl alcohol | 7 | — | 7 | 7 |
| Solvent | PEG-300 | 4 | 2 | 4 | 4 |
| Emulsifier | Stearic Acid | — | 2 | — | — |
| | Emulsifying wax | — | 5 | — | — |
| | PEG-6/PEG-32/Glycol Stearate (Tefose-63) | 8 | — | 8 | 8 |
| | Cetostearyl alcohol | 8 | — | 8 | 8 |
| | Ceteareth-6/Stearyl alcohol (Cremophor A6) | 2 | 1 | 2 | 2 |
| | Ceteareth-25 (Cremophor A25) | 2 | 1 | 2 | 2 |
| Vehicle | Purified water | QS | QS | QS | QS |

Formulations 1, 3 and 4 of Table 1 each comprises a thickened cream with viscosity around 200,000-600,000 cPs. Formulation 2 has a reduced oil phase composition and different emulsifiers, which resulted in a formulation of significantly lower viscosity.

A complex oil phase supports increased oxymetazoline flux relative to gel and creams with simple or no oil phase as shown in Table 1a. Formulations in Table 1b-1c describe cream formulations comprising simplified oil phase systems (Table 1b) and emulsified gel formulations with high solvent phase systems (Table 1c).

TABLE 1a

Oxymetazoline cream control formulation

| | | Formulation Number Oxy cream control |
|---|---|---|
| Function | Ingredient | % w/w |
| Active | Oxymetazoline HCl | 0.5 |
| Preservative | Methylparaben | 0.2 |
| | Propylparaben | 0.05 |
| | Phenoxyethanol | 0.8 |

TABLE 1a-continued

Oxymetazoline cream control formulation

| Function | Ingredient | Formulation Number Oxy cream control % w/w |
|---|---|---|
| Buffer | Sodium citrate, dihydrate | 0.3 |
|  | Citric acid, anhydrous | 0.219 |
| Chelating Agent | Edetate, disodium | 0.01 |
| Antioxidant | BHT | 0.05 |
| Oil Phase | Lanolin, anhydrous | 2 |
|  | Medium chain triglycerides | 7 |
|  | Diisopropyl adipate | 7 |
|  | Oleyl alcohol | 7 |
| Solvent | PEG-300 | 4 |
| Emulsifier | PEG-6/PEG-32/Glycol Stearate (Tefose-63) | 8 |
|  | Cetostearyl alcohol | 8 |
|  | Ceteareth-6/Stearyl alcohol (Cremophor A6) | 2 |
|  | Ceteareth-25 (Cremophor A25) | 2 |
| Vehicle | Purified water | QS |

TABLE 1b

Oxymetazoline cream formulations with simplified oil phase systems

| | | Cream Formulations | |
|---|---|---|---|
| | | D1 | F1 |
| Function | Components | Amt (wt %) | |
| API | Oxy | 0.5 | 0.5 |
| Emulsifier | Tefose 63 | 8 | 8 |
|  | Cetostearyl alcohol | 5 | 0 |
|  | Cetyl alcohol | 5 | 5 |
|  | Emulsifying wax | 0 | 3 |
| Solvent | Glycerin | 0 | 4 |
| Oil Phase | Isopropyl palmitate | 0 | 2 |
|  | Labrafil M1944 CS | 5 | 0 |
| Preservative | Methyl paraben | 0.2 | 0.2 |
|  | Phenoxyethanol | 0.8 | 0.8 |
|  | Propyl paraben | 0.05 | 0.05 |
| Buffer | Citric acid | 0.74 | 0.74 |
| Vehicle | Water | QS 100% | QS 100% |

TABLE 1c

Oxymetazoline gel formulations with solvent phase system

| | | Gel Formulations | | | |
|---|---|---|---|---|---|
| | | 1 | 2 | 3 | 11 |
| Function | Components | Amt (wt %) | | | |
| API | Oxy | 0.5 | 1.5 | 0.5 | 0.5 |
| Preservatives | Methyl paraben | 0.2 | 0.2 | 0.2 | 0.2 |
|  | Propyl paraben | 0.02 | 0.02 | 0.02 | 0.02 |
|  | Phenoxyethanol | 1 | 1 | — | — |
| Solvent | Glycerol | 5 | 5 | — | — |
|  | Transcutol | 5 | 5 | 10 | 10 |
|  | Ethanol | 5 | 5 | — | — |
| Emulsifier | Lutrol F127 | 1 | 1 | — | — |
| Antioxidant | EDTA | 0.03 | 0.03 | 0.03 | 0.03 |
| Thickeners | Carbopol 974 | 2 | — | — | 2 |
|  | Sepineo P 600 | — | — | 4 | — |
|  | HEC HHX | — | 1 | — | — |
| Buffer | NaOH/Citric | ps pH 4.75 | ps pH 4.75 | ps pH 4.75 | ps pH 4.75 |
| Emollient | Cyclomethicone | 13 | 13 | — | — |
| Vehicle | Buffered water (phosphate/citrate) | QS 100% | QS 100% | QS 100% | QS 100% |

Example 2: In Vitro Study

Methodology

Human cadaver skin from the back or leg region was mounted on a diffusion chamber. Skin samples from two donors were evaluated. Skin samples were applied stratum corneum side up on a Franz diffusion cell. Formulation was applied in a defined volume to the skin sample and gently rubbed into the skin with a glass stir rod. The receptor chamber of the diffusion cell was filled with phosphate buffered saline. At each timepoint the entire receptor chamber was emptied and replaced with fresh buffer. The aqueous samples were analyzed for oxymetazoline and presented as a cumulative amount versus time plot in FIG. 1 below.

Results

Figure 3:
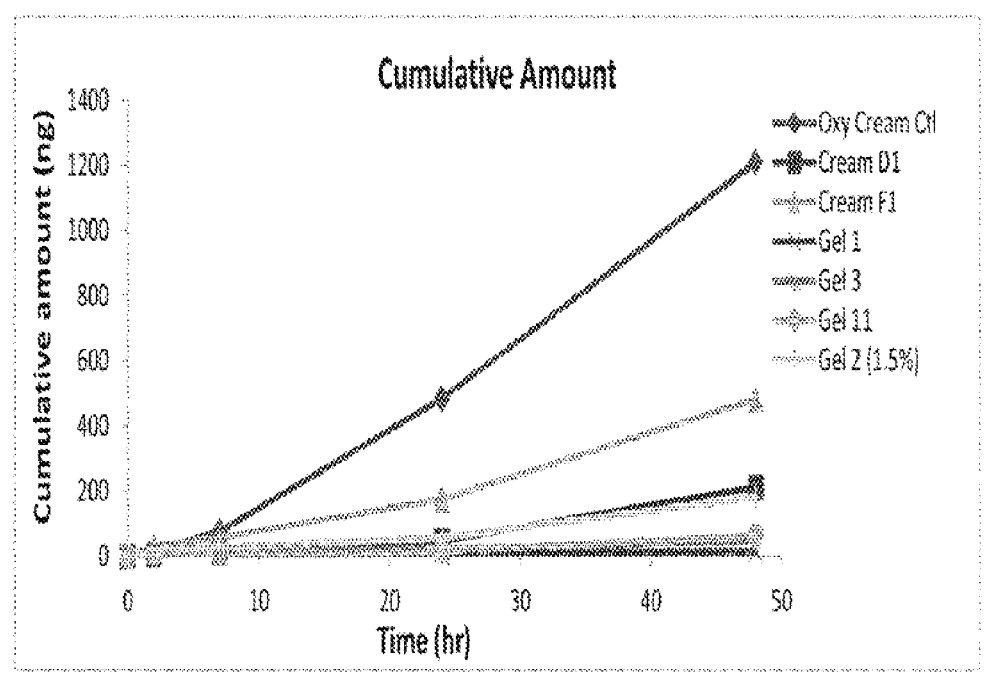
FIG. 3 shows Cumulative amount of Oxymetazoline versus time plots for each formulation studied. Each data point represents the mean of six determinations (three determinations each from a single skin donor). Two donors were studied.

FIG. 3 presents the oxymetazoline concentration in the receptor fluid as a function of time. The results show that the oxymetazoline cream control formulation comprising a complex oil phase produces the highest permeation. Results from this skin penetration study show the unexpected combination of the excipients in the oxy cream control produce a higher skin permeation relative to other cream and gel formulations. It was not anticipated that the oil phase components of the control formulation would result in an increase in the cumulative amount of oxymetazoline relative to the compositions in Table 1b because oxymetazoline is hydrophilic.

Example 3: Clinical Efficacy and Safety of Oxymetazoline HCl Cream Formulations

Clinical Study Objectives

To evaluate the safety and efficacy of oxymetazoline HCl cream 0.5%, 1.0%, and 1.5%, once-daily and twice-daily topical application compared to vehicle for 28 consecutive days for the treatment of patients with moderate to severe facial erythema associated with rosacea.

Methodology

Structure: Multicenter, randomized, double-blind, parallel-group, vehicle-controlled study Duration: Approximately 86 days; up to a 30-day screening period, 28-day treatment period, and 28-day follow-up period Study Treatment Groups: Oxymetazoline HCl cream 0.5%, 1.0%, and 1.5%

Control: Vehicle cream

Dosage/Dose Regimen:

| Group 1 | Oxymetazoline 0.5% once-daily (hereafter referred to as Oxy 0.5% QD) |
| Group 2 | Oxymetazoline 1.0% once-daily (hereafter referred to as Oxy 1.0% QD) |
| Group 3 | Oxymetazoline 1.5% once-daily (hereafter referred to as Oxy 1.5% QD) |
| Group 4 | Vehicle once-daily (hereafter referred to as vehicle QD) |
| Group 5 | Oxymetazoline 0.5% twice-daily (hereafter referred to as Oxy 0.5% BID) |
| Group 6 | Oxymetazoline 1.0% twice-daily (hereafter referred to as Oxy 1.0% BID) |
| Group 7 | Oxymetazoline 1.5% twice-daily (hereafter referred to as Oxy 1.5% BID) |
| Group 8 | Vehicle twice-daily (hereafter referred to as vehicle BID) |

Duration of dosing for all 8 groups was 28 consecutive days. Patients assigned to the once-daily dosing groups were instructed to apply study medication in the morning each day. Patients assigned to the twice-daily dosing groups were instructed to apply study medication in the morning and a second dose approximately 6 to 10 hours after the morning dose. On days 1, 2, 14, and 28, all patients were instructed to apply the study medication at the clinic. Patients in the twice-daily dosing groups were instructed to apply the second dose 6 hours after the morning dose at the clinic.

Randomization/Stratification: At each investigational site, eligible patients were randomized to 1 of 8 treatment groups in a 1:1:1:1:1:1:1:1 ratio to receive either once or twice daily application of oxymetazoline HCl cream 0.5%, 1.0%, or 1.5% or vehicle.

Visit Schedule: 8 scheduled study visits: screening (days −30 to −2), treatment period (days 1, 2, 14, and 28), follow-up (days 29 and 35), and exit (day 56)

Number of Patients (Planned and Enrolled)

Approximately 360 patients were planned to be enrolled. A total of 357 patients were enrolled, of which 356 patients were randomized: 45, 44, 44, 44, 45, 45, 45, and 44 patients were randomized to the Oxy 0.5% QD, Oxy 1.0% QD, Oxy 1.5% QD, vehicle QD, Oxy 0.5% BID, Oxy 1.0% BID, Oxy 1.5% BID, and vehicle BID treatment groups, respectively.

Diagnosis and Main Criteria for Eligibility

Condition/Disease: Moderate to severe facial erythema associated with rosacea

Key Inclusion Criteria: Male or female patients 18 years of age or older with moderate to severe facial erythema associated with rosacea defined as a grade of ≥3 on the Allergan Clinician Erythema Assessment (CEA) scale with photonumeric guide as assessed by the investigator and either "more redness than I prefer" or "completely unacceptable redness" on the Subject Self-Assessment (SSA) of erythema scale as assessed by the patient, and stable facial erythema associated with rosacea with minimal variation from day to day and within each day, in the opinion of the patient.

Key Exclusion Criteria: Any uncontrolled systemic disease or any of the following conditions: clinically unstable hypertension, orthostatic hypotension, clinically unstable cerebral insufficiency, coronary insufficiency, cardiac arrhythmia (ie, tachyarrhythmias, advanced ventricular arrhythmias), ischemic heart disease, benign prostate hypertrophy, or Raynaud's syndrome. Greater than 3 inflammatory lesions on the face, facial acne that may have interfered with study assessments as determined by the investigator, clinical signs of actinic damage (eg, actinic lentigines, mottled hyperpigmentation or hypopigmentation, yellowish discoloration, excessive telangiectasia) on the face that may have interfered with study evaluations in the opinion of the investigator, narrow angle glaucoma, current use of monoamine oxidase (MAO) inhibitors.

Test Product, Dose and Mode of Administration, Batch Number: Oxymetazoline HCl cream 0.5%, 1.0%, or 1.5% administered topically to the face by the patient once or twice daily, based on the randomization assignment; formulation numbers 11007X (0.5%), 11008X (1.0%), 11009X (1.5%); batch numbers EHC-C (0.5%), EHD-C (1.0%), EHE-C (1.5%).

Reference Therapy, Dose and Mode of Administration, Batch Number: Oxymetazoline HC cream vehicle administered topically to the face by the patient once or twice daily, based on the randomization assignment; formulation number 11006X; batch number EHB-C.

Duration of Treatment: The total duration of study participation for each patient was approximately 86 days and each patient received treatment for approximately 28 consecutive days.

Efficacy, Health Outcomes, Drug Concentration, Safety, and Other Measurements

Efficacy: Efficacy measures were:
  investigator's assessment of the severity of facial erythema using the CEA scale with photonumeric guide
  patient's assessment of the severity of facial erythema using the SSA of erythema scale An additional efficacy measure was included in this study as an exploratory measure to assess the patient's perception of facial erythema (using different response options/categories of erythema than the SSA) for potential use in future studies.
  the patient's assessment of the severity of facial erythema as measured by the Subject Self-Assessment for Rosacea Facial Redness (referred to as SSA-2), which included a photoguide.

The SSA-2 is similar to the SSA in that it is a 5-point patient assessment of facial redness from a score of 0 (clear) to 4 (severe); however, patients use a photoguide (similar to the CEA photonumeric guide) to complete their assessments.

Health Outcomes: The following patient-reported outcome (PRO) measures were included in this study as exploratory measures to assess treatment responsiveness and determine an appropriate responder definition for use in future studies:
  the patient's assessment of symptoms associated with erythema as measured by the Symptom Assessment for Rosacea Facial Redness (Symptoms Assessment)
  the patient's assessment of functional impacts (eg, emotional, social) associated with erythema as measured by the Impact Assessment for Rosacea Facial Redness (Impact Assessment)
  the patient's assessment of satisfaction with treatment as measured by the Satisfaction Assessment for Rosacea Facial Redness (Satisfaction Assessment: baseline and follow-up versions)

Drug Concentration: Blood samples were drawn on days 1 and 28 at predose, 2, 4, 6, 8, 10, and 12 hours after the morning dose throughout the study. Additional trough samples were collected on days 2, 14, and 29. The final pharmacokinetic sample was collected on day 35 after all assessments were completed. Plasma was analyzed for oxymetazoline concentrations using a validated liquid chromatography-tandem mass spectrometry method with a lower limit of quantification of 10 pg/mL.

Safety: Adverse events, facial dermal tolerability assessment, 12-lead electrocardiograms (ECGs), laboratory tests (fasting biochemistry and hematology, urinalysis), urine pregnancy tests for women of childbearing potential, physical examinations, vital sign measurements (blood pressure, pulse rate, respiratory rate, and oral body temperature).

Other Measures: Other measures included Clinician Telangiectasia Assessment (CTA), lesion count, Aesthetic Questionnaire, and standardized photography/digital image analysis (DIA).

Statistical and Data Analysis Methods

Analysis Populations: The following 3 populations were analyzed. The modified intent-to-treat (mITT) population consisted of all randomized patients who applied study medication during the study, had both CEA and SSA measurements at baseline (ie, predose on day 1), and at least 1 postbaseline measurement for both CEA and SSA. The per-protocol (PP) population consisted of randomized patients with no major protocol violation during the study. The PP population was determined prior to database lock. The safety population consisted of patients who applied at least 1 dose of study medication in the study. Efficacy analyses were performed on the mITT population as the primary population. Primary efficacy analyses were also performed on the PP population. Safety analyses were based on the safety population.

Primary Efficacy Analysis: The primary efficacy variable was defined as patients with at least a 2-grade decrease (improvement) on both CEA and SSA from baseline (pre-dose on day 1) over a 12-hour period measured at hours 2, 4, 6, 8, 10, and 12 on day 28. A generalized linear model with a logit link function and exchangeable covariance structure using generalized estimation equations (GEE) was performed to analyze the primary variable at hours 2, 4, 6, 8, 10, and 12 on day 28 to compare treatment difference (ie, Oxy 0.5% QD versus vehicle QD, Oxy 1.0% QD versus vehicle QD, and Oxy 1.5% QD versus vehicle QD, separately). The model included fixed effects of treatment group and timepoint. Similar analyses were performed to compare each active twice-daily treatment group to vehicle twice-daily.

Secondary Efficacy Analysis: The secondary efficacy variables were defined as follows: the proportion of patients with at least a 2-grade decrease (improvement) on both CEA and SSA from baseline at hour 0.5 postdose on day 28; and the proportion of patients with at least a 2-grade decrease (improvement) on both CEA and SSA from baseline at 1 hour postdose on day 28. A frequency distribution of patients with at least a 2-grade decrease (improvement) on both CEA and SSA by timepoint (hours 0.5 and 1) on day 28 and treatment group was tabulated. A 2-sided 90% confidence interval (CI) for the treatment difference (ie, each active treatment minus vehicle) by timepoint was provided using a normal approximation method. A Pearson's chi-square test was used to test the treatment difference. If 25% or more of the cells had expected counts less than 5, a Fisher's exact test was used.

The same statistical method used in the primary efficacy analysis was used to analyze the primary variable between 2 active treatment groups (eg, Oxy 1.5% QD versus Oxy 0.5% QD). In addition, a frequency distribution of patients with at least a 2-grade decrease (ie, treatment responder) on both CEA and SSA by timepoint (hours 2, 4, 6, 8, 10, and 12) on day 28 and treatment group was tabulated. A 2-sided 90% CI for the treatment difference (ie, Oxy 0.5% QD minus vehicle QD, Oxy 1.0% QD minus vehicle QD, and Oxy 1.5% QD minus vehicle QD, separately) by timepoint was provided using a normal approximation method. The same analyses were performed for twice-daily dosing and for the difference between 2 active treatment groups (eg, Oxy 0.5% BID and Oxy 1.0% QD).

Health Outcomes Analysis: The health outcomes analyses were defined as the proportion of patients with at least a 1-grade improvement on each question of the 3 PRO measures from baseline on day 28.

Pharmacokinetic Analysis: Noncompartmental analysis was performed to determine the maximum observed plasma concentration ($C_{max}$), corresponding time to reach maximum observed plasma concentration ($T_{max}$), area under the plasma concentration-time curve from time 0 to time t ($AUC_{0-t}$), accumulation ratio ($R_0$), and effective half-life ($T_{eff}$) of oxymetazoline in plasma. These parameters were calculated, whenever possible.

Safety Analysis: For pretreatment adverse events (PTAEs), number and percent of patients reporting the PTAEs at least once were tabulated by descending order of incidence rate, by primary system organ class (SOC) and by preferred term (PT), and primary SOC, PT, and severity. Treatment-emergent adverse events (TEAEs) regardless of causality were analyzed in the same manner. All analyses were by treatment group. Each active once-daily treatment group was compared to vehicle once-daily using a Pearson's chi-square test or a Fisher's exact test if 25% or more of cells had expected counts less than 5. The same analyses were performed for twice-daily dosing groups. Treatment-related TEAEs were analyzed using the same statistical methods as the TEAEs. Data from facial dermal tolerability assessments were summarized using frequency distributions and shift tables by treatment group. All other safety data were summarized by descriptive statistics or frequency distribution.

Summary of Results

Patient Disposition and Demographics: A total of 357 patients were enrolled into the study, of which 356 patients were randomized. A majority of patients (95.2% [339/356]) completed the study. In the twice-daily treatment groups, 6.7% (9/135) of the Oxy patients and 4.5% (2/44) of the vehicle patients discontinued the study. In the once-daily treatment groups, 3.0% (4/133) of the Oxy patients and 4.5% (2/44) of the vehicle patients discontinued the study. The primary reason for discontinuation from the study was adverse events in 2.8% (10/356) of all patients.

The demographic variables were similar across all treatment groups. The mean age of the patients was 50.0 years (range 19 to 79 years). The largest proportion of patients (60.4%) was aged between 45 and 64 years of age, with 29.5% being <45 years of age, and 10.1% being ≥65 years of age. There were more females than males (80.1% versus 19.9%), and the majority of the population was Caucasian (91.3%).

Efficacy:
A statistically significant reduction in facial erythema as measured by the composite assessment, i.e., the proportions of patients with at least a 2-grade decrease (improvement) from baseline over a 12-hour period for both the CEA and SSA on day 28, was demonstrated with the 1.5% and 1.0% doses of oxymetazoline cream following twice-daily dosing (p=0.006 and p=0.021, respectively), and with all 3 doses of oxymetazoline cream (1.5%, 1.0%, and 0.5%) following once-daily dosing (p=0.012, p=0.006, and p=0.049, respectively).
The proportions of responders in the twice-daily treatment groups at hour 4 (peak timepoint) on day 28 were 22.2%, 20.0% and 11.1% with Oxy 1.5%, 1.0%, and 0.5%, respectively, compared to 6.8% with vehicle. The proportions of responders in the twice-daily treatment groups were maintained at hour 12 on day 28, with 15.6%, 11.1% and 13.3% in the Oxy 1.5%, 1.0%, and 0.5% groups, respectively, compared to only 4.5% in the vehicle group.
The proportions of responders in the once-daily treatment groups at hour 4 (peak timepoint) on day 28 were 27.3%, 31.8% and 17.8% with Oxy 1.5%, 1.0%, and 0.5%, respectively, compared to 4.5% with vehicle. The proportions of responders in the once-daily treatment groups were maintained at hour 12 on day 28, with 13.6%, 13.6%, and 13.3% in the Oxy 1.5%, 1.0%, and 0.5% groups, respectively, compared to only 2.3% in the vehicle group.
A statistically significant difference based on the composite 2-grade improvement was observed as early as 2 hours after the first application on day 1 for a majority of the Oxy treatment groups compared with vehicle.
The pair-wise comparison showed no statistically significant differences in response rates over a 12-hour time period on day 28 between any of the Oxy twice-daily or once-daily treatment groups, demonstrating that twice-daily dosing did not provide any significant improvement over once-daily dosing for any of the Oxy treatment groups. A numerically higher response rate was observed for Oxy 1.0% QD versus Oxy 0.5% QD at most timepoints. When comparing the Oxy 1.5% QD and the 1.0% QD doses, the response rates were similar.

For the secondary efficacy variables (defined as the proportions of patients with at least a 2-grade improvement on both the CEA and SSA from baseline at hour 0.5 and hour 1.0 after application of the first dose on day 28), only the Oxy 1.5% QD treatment group showed statistically significant differences compared with vehicle at hour 1.0.

The response rates on day 28 were higher compared with response rates on day 1 for all Oxy treatment groups, demonstrating that no tachyphylaxis was observed during the study.

A statistically significant reduction in rosacea facial redness, as demonstrated by the proportions of patients with at least a 2-grade decrease (improvement) from baseline over a 12-hour period for both the CEA and SSA-2, was observed with Oxy 1.5% and 1.0% given twice-daily and once-daily compared with vehicle on day 28, with responses observed as early as day 1.

Correlation analyses demonstrated that there was a high correlation between the SSA and SSA-2 with a Spearman correlation coefficient of 0.85 (90% CI [0.842, 0.851]).

There were no statistically significant between-group differences in the proportions of responders at any timepoint during the 4-week posttreatment period. During this follow-up phase, During this follow-up phase, no patients had rebound or worsening of erythema, as defined by a 1-grade worsening from baseline on both of the CEA and SSA scales, as well as both of the CEA and SSA-2 scales.

Subgroup analyses of the primary efficacy variable demonstrated that treatment with oxymetazoline was efficacious in the reduction of erythema regardless of sex, age, CEA score at baseline, or SSA score at baseline.

Health Outcomes:

A summary of the proportion of patients with at least a 1-grade improvement on each question of the PRO measures from baseline on day 28 is provided below. Note that all PRO measures were administered at predose (prior to treatment) for validation purposes (for a separate study), which may have resulted in lower scores.

On day 28, the proportions of patients with at least a 1-grade improvement on each question of the Symptom Assessment PRO ranged from 35.6% to 68.9% for the active treatment groups (once-daily and twice-daily) compared to 31.8% to 72.7% for the vehicle groups, suggesting appropriate responsiveness to active treatment with oxymetazoline.

The proportions of patients with at least a 1-grade improvement on each question of the Impact Assessment PRO were similar for all treatment arms on day 28. The proportions ranged from 21.4% to 77.8% for the active treatment groups compared to 23.3% to 77.3% for the vehicle groups.

On day 28, the proportions of patients with at least a 1-grade improvement on each question of the Satisfaction Assessment were up to 43.2% for the active treatment groups and up to 45.2% for the vehicle groups.

Pharmacokinetics:

Pharmacokinetic parameters, where applicable, were calculated for each patient following dermal administration of oxymetazoline cream. The maximum concentrations in the once-daily and twice-daily dose groups were observed between 6 to 12 hours (median $T_{max}$) and 4 to 6 hours (median $T_{max}$) postdose, respectively. Following once-daily dosing, the mean $C_{max}$ in the 1.5% dose group on day 28 was 98.0 pg/mL which was similar to the 115 pg/mL mean $C_{max}$ observed in the Oxy 1.5% BID treatment group on day 28. The highest mean $AUC_{0-24}$ following administration of 1.5% once-daily or twice-daily was 1680 and 2660 pg·hr/mL, respectively.

With an increase in dosing frequency (twice-daily), there did not appear to be a dose proportional increase in systemic exposure when compared to once-daily dosing. Systemic exposure appeared to increase nearly dose proportionally. Following 28 days of dosing, a mean accumulation ratio of approximately 2 was observed across all once-daily treatment groups. Increased accumulation was observed in the twice-daily treatment groups, with a mean accumulation ratio between 4.86 to 6.48 when comparing AUC after the first dose on days 1 and 28.

Data indicates that steady state may have been reached by the second dose for the once-daily groups and after the third dose for the twice-daily groups. An effective half-life of 18 to 28 hours was observed following repeated dermal administration of oxymetazoline cream.

Digital Image Analysis:

Among the 6 measures evaluated from the DIA (ie, Fractional Area, Erythema Severity, Erythema Redness, Erythema Contrast, Intensity of Erythema, and Erythema Visibility), Fractional Area had the best correlation with the CEA scale, with a Spearman correlation coefficient of 0.47 (95% CI [0.436, 0.498]). In general, there was a good differentiation on the improvement from baseline in Fractional Area between the Oxy once-daily groups and the vehicle once-daily group.

Safety:

All 3 doses of oxymetazoline (1.5%, 1.0%, and 0.5%) were well-tolerated after once-daily or twice-daily application for up to 28 consecutive days, with TEAEs reported in 33.1% (118/356) of all patients and treatment-related adverse events reported in 9.8% (35/356) of patients.

The overall incidences of TEAEs and treatment-related TEAEs were similar across the 3 Oxy twice-daily treatment groups, but slightly higher in the Oxy 1.5% QD group than the Oxy 1.0% and 0.5% QD groups. Most TEAEs were considered to be of mild or moderate severity.

The most frequently reported TEAEs (in ≥2% of all patients) were headache, application site dermatitis, contact dermatitis, upper respiratory tract infection, application site papules, application site erythema, and application site acne.

Treatment-related TEAEs were reported in 28 oxymetazoline-treated patients and 5 vehicle-treated patients. The most frequently reported treatment-related TEAEs (in >1% of all patients) were application site events, including dermatitis, papules, pain (ie, stinging, burning), erythema, pruritus, and acne. A majority of the events were mild or moderate in severity and resolved without sequelae. Most of these application site events (except 4 cases of acne and papules) were resolved in the 4-week posttreatment follow-up period.

The most frequently reported non-application site TEAE was headache, which occurred similarly in oxymetazoline-treated patients and vehicle-treated patients (4.9% and 4.5%, respectively).

A total of 2.8% (10/356) of patients discontinued the study due to TEAEs (8 oxymetazoline-treated patients and 2 vehicle-treated patients), the majority of which were due to application site adverse events, including application site dermatitis, application site acne, application site erythema, application site pruritus, application site irritation, and application site pain.

There were no deaths reported during the study. There were 5 serious adverse events reported in 3 patients, none of which were considered to be related to study treatment.

Subgroup analyses demonstrated that the incidence of TEAEs was similar across the age and sex subgroups.

The proportions of patients with worsening in severity of facial tolerability were similar between oxymetazoline-treated and vehicle-treated patients following twice-daily or once-daily dosing on days 1, 14, and 28, demonstrating that all Oxy treatment groups had an acceptable local tolerability profile.

There were no clinically relevant changes from baseline or differences between treatment groups with respect to laboratory values, vital signs, and physical examination findings.

There was no increase in mean lesion counts or in the proportions of patients with moderate or severe telangiectasia in any of the treatment groups during the study or posttreatment period.

There were no clinically relevant ECG findings observed during the study.

Conclusion(s)

This multicenter, randomized, double-blind, vehicle-controlled, parallel-group study demonstrated that oxymetazoline hydrochloride cream at concentrations of 1.5%, 1.0%, and 0.5% given once daily significantly reduced the facial erythema associated with rosacea, as assessed by the investigator using the CEA and by the patient using the SSA. A statistically significant reduction in facial erythema was also demonstrated with the 1.5% and 1.0% doses of oxymetazoline cream following twice-daily dosing (with the second dose administered 6 hours after the first dose); however, no additional treatment benefit was observed with twice-daily dosing over once-daily dosing. All concentrations of oxymetazoline were well tolerated when administered once or twice daily, with the majority of adverse events limited to localized dermatological effects.

LIST OF ABBREVIATIONS AND DEFINITION OF TERMS

| Abbreviation/ Term | Definition |
| --- | --- |
| ACL | anterior cruciate ligament |
| AQ | Aesthetic Questionnaire |
| $AUC_{0-t}$ | area under the plasma concentration-time curve from time 0 to time t |
| BID | twice daily |
| BLQ | below the lower limit of quantitation |
| CEA | Clinician Erythema Assessment |
| CI | confidence interval |

-continued

| Abbreviation/ Term | Definition |
| --- | --- |
| $C_{max}$ | maximum observed plasma concentration |
| CTA | Clinician Telangiectasia Assessment |
| DIA | digital image analysis |
| DMP | Data Management Plan |
| ECG | electrocardiogram |
| eCRF | electronic case report form |
| EDC | electronic data capture |
| ERT | eResearch Technology |
| FDA | Food and Drug Administration |
| GCP(s) | Good Clinical Practice(s) |
| GEE | generalized estimation equations |
| HCl | hydrochloride |
| HIPAA | Health Insurance Portability and Accountability Act |
| ICF | informed consent form |
| ICH | International Conference on Harmonisation |
| IPL | intense pulsed light |
| IRB | Institutional Review Board |
| IVRS | interactive voice response system |
| IWRS | interactive web response system |
| LC-MS/MS | liquid chromatography-tandem mass spectrometry |
| LLOQ | lower limit of quantitation |
| MAO | monoamine oxidase |
| MedDRA | Medical Dictionary for Regulatory Activities |
| Min | minute |
| mITT | modified intent-to-treat |
| NA or N/A | not applicable or not available |
| OTC | over-the-counter |
| Oxy | oxymetazoline hydrochloride |
| PDF | portable document format |
| PDT | photodynamic therapy |
| PEG | polyethylene glycol |
| PP | per protocol |
| PRO | patient-reported outcome |
| PT | preferred term |
| PTAE | pretreatment adverse event |
| $R_0$ | accumulation ratio |
| QD | once daily |
| QTcB | QT interval corrected using the Bazett's correction |
| QTcF | QT interval corrected using the Fridericia's correction |
| SOC | system organ class |
| SOP(s) | standard operating procedure(s) |
| SSA | Subject Self-Assessment; Subject Self-Assessment of Erythema Scale |
| SSA-2 | Subject Self-Assessment for Rosacea Facial Redness (with photo guide) |
| $T_{1/2}$ | terminal half-life |
| $T_{eff}$ | effective half-life |
| TEAE | treatment-emergent adverse event |
| $T_{max}$ | time corresponding to maximum observed plasma concentration |
| US | United States |

1. Introduction

Oxymetazoline hydrochloride (HCl) is a potent and highly specific α1a-adrenergic receptor agonist and an effective vasoconstrictor. Itis currently approved by the United States (US) Food and Drug Administration (FDA) as an over-the-counter (OTC) eye drop product for the indications of conjunctivitis and ocular irritation, and as an OTC nasal spray for nasal congestion (Oxymetazoline: DRUGDEX®). Each route of administration uses a different formulation and concentration of oxymetazoline (eye drops up to 0.025% and nasal sprays up to 0.05%). In the current study, oxymetazoline HCl was formulated as a cream (referred to hereafter as oxymetazoline cream) for topical facial dermal application and was being evaluated for the treatment of erythema associated with rosacea.

Rosacea is a common, chronic dermatological condition of uncertain etiology that is characterized by a myriad of clinical manifestations, including persistent erythema (which may be accompanied by facial stinging and burning), facial edema, superficial telangiectasias, recurrent papules and pustules, facial phymas (most commonly rhinophyma), and ocular manifestations (Rebora, 2002). It is estimated to affect more than 16 million Americans (National Rosacea Society, 2012). Rosacea is common, especially in fair-skinned individuals of Celtic or northern European origin (Jansen and Plewig 1997). Its onset is typically between the ages of 30 and 50, and women are affected 2 to 3 times more often than men (Jansen and Plewig, 1997; Norwood and Norwood, 2007). Of all the clinical manifestations of rosacea, facial flushing and persistent erythema are among the most common and are often associated with psychological distress (Breneman et al. 2004; Drummond and Su, 2012; Su and Drummond, 2012). Although the precise etiology and pathogenesis of erythematous rosacea remain uncertain, it is theorized that abnormal flushing and persistent erythema result from a progressive dysregulation in the cutaneous vasomotor response (ie, persistently dilated facial blood vessels)(Crawford et al, 2004, Parodi et al. 1980). Evaluation of neurovascular and neuroimmune changes of rosacea using quantitative real-time polymerase chain reaction and immunohistochemistry supports the significant presence of vasodilatation of blood vessels and lymphatics in rosacea, demonstrates the upregulation of genes involved in vasodilatation, and supports the observation that blood vessels in rosacea retain their ability to respond to vasoactive stimuli (Del Rosso, 2012).

While rosacea is not curable, it is a treatable condition; treatment goals include alleviation of signs and symptoms, improvement of appearance, and delay or prevention of advancement of the condition. Effective treatments have been developed to treat papulopustular rosacea using topical anti-infective agents such as sulfonamides, metronidazole, azelaic acid, and tetracyclines (Elewski et al. 2011).

Conspicuous facial redness may have a deep impact on a patient's self-esteem and quality of life. Surveys of rosacea patients conducted by the National Rosacea Society indicate that more than 76% had lowered self-esteem and self-confidence; of rosacea patients with severe symptoms, 88% said the condition had adversely affected their professional interactions (National Rosacea Society, 2012).

Five clinical studies of topical, dermal oxymetazoline have been conducted for the treatment of facial erythema associated with rosacea by Allergan and Vicept Therapeutics, Inc. All clinical studies have been conducted with the same cream formulation with varying concentrations of oxymetazoline. Across these studies, 314 patients with rosacea have been exposed to the cream formulation with concentrations of oxymetazoline varying from 0.01% to 1.5%.

A phase 1, multicenter, randomized, double-blind, vehicle-controlled, parallel-group, split face study in patients with stable moderate to severe erythema associated with rosacea (Study 199201-001) demonstrated that topical facial administration of oxymetazoline cream 1.5%, 1.0%, and 0.5% twice-daily for 5 consecutive days were well tolerated. There were no serious adverse events and no patients discontinued the study. The majority of the treatment-emergent adverse events (TEAEs) reported were considered related to study treatment and were mild or moderate in severity. The proportion of responders, defined as patients' facial sites (left or right) with at least a 2 grade improvement on both the Clinician Erythema Assessment (CEA) and Subject Self-Assessment (SSA) scales, increased in a dose-dependent manner for the majority of timepoints. The best response rates were observed with oxymetazoline 1.0% and 1.5%. A peak in response rate was observed at 4 hours postdose. The proportion of responders at hour 4 on day 1 was 37.5% with oxymetazoline 1.5%, 34.4% with oxymetazoline 1.0%, and 18.8% with oxymetazoline 0.5%, compared to 0.0% with vehicle. On day 1, the proportion of responders was statistically significantly superior to vehicle with oxymetazoline 1.5% at 2, 4, 6, and 10 hours postdose; with oxymetazoline 1.0% at 1, 2, 4, and 6 hours postdose; and with oxymetazoline 0.5% at 2, 4, and 6 hours postdose. Continued efficacy was maintained throughout the study; however, the results on day 1 were more pronounced than those on day 5.

Four randomized, double-blind, vehicle-controlled studies were conducted by Vicept in which patients with stable, moderate to severe erythema associated with rosacea received a single or once-daily facial application of oxymetazoline cream at concentrations of 0.01% to 0.5%. These studies included 254 patients who were treated with oxymetazoline cream. A bioavailability study demonstrated no measurable systemic exposure of oxymetazoline following application of 0.15% cream. A second bioavailability study found the mean maximum concentration ($C_{max}$) and the area under the plasma concentration-time curve (AUC) following an application of 0.5% cream to be approximately 7- and 6-fold lower, respectively, than those following administration of Afrin® nasal spray 0.05%. Two vehicle-controlled dose-ranging studies with concentrations up to 0.5% cream showed evidence of dose-dependent efficacy as evaluated using the CEA and SSA. The only TEAEs considered to be treatment-related in patients treated with oxymetazoline cream were erythema, pruritus, and eye irritation. There were no serious adverse events or discontinuations due to adverse events. There were no notable changes during these studies in clinical laboratory tests, vital signs, or (in the studies in which they were evaluated) electrocardiograms (ECGs) or intraocular pressure.

Results from these 5 studies support topical dermal safety of oxymetazoline cream up to 1.5% twice-daily. Additionally, 4 human dermal safety studies of 0.5% oxymetazoline cream (a 21 day cumulative irritation study, a repeat-insult patch test, a phototoxicity study, and a photo contact-allergy study) indicate acceptable dermal safety with the product. Detailed results of these studies can be found in the oxymetazoline cream Investigator's Brochure.

The current trial was designed to further evaluate the safety and efficacy of oxymetazoline cream in the treatment of facial erythema associated with rosacea at concentrations of 0.5%, 10%, and 1.5%, with longer exposure (28 consecutive days) and administered once-daily or twice-daily.

2. Study Objectives

To evaluate the safety and efficacy of oxymetazoline cream 0.5%, 1.0%, and 1.5%, once-daily and twice-daily topical application compared to vehicle for 28 consecutive days for the treatment of patients with moderate to severe facial erythema associated with rosacea.

3. Investigational Plan 3.1 Overall Study Design and Plan

This was a multicenter, randomized, double-blind, vehicle-controlled, parallel-group study to investigate the safety, efficacy, facial dermal tolerability, and pharmacokinetic profile of oxymetazoline cream 0.5%, 1.0%, and 1.5% (also referred to as Oxy 0.5%, Oxy 1.0%, and Oxy 1.5%, respectively) compared to vehicle (once-daily or twice-daily) topical application in patients with moderate to severe facial erythema associated with rosacea.

The total duration of study participation for each patient was up to approximately 86 days from the screening visit to study exit. The 8 study visits included: screening (days −30 to −2), randomization day 1, treatment period visits (days 2, 14, and 28), follow-up (days 29 and 35), and exit (day 56). After the screening visit, each qualified patient returned on day 1 for confirmation of eligibility. Eligible patients were randomized and study medication was dispensed. All patients were to apply study medication for 28 consecutive days.

At the day 1, day 14, and day 28 visits, patients remained at the clinic for at least 12 hours. During these study visits, patients applied study medication at the clinic. At the day 2 visit, patients applied study medication (morning dose only) at the clinic. Eligible patients were randomized to 1 of 8 treatment groups as shown in a 1:1:1:1:1:1:1:1 ratio.

| Group 1 | Oxymetazoline 0.5% once-daily | (hereafter referred to as Oxy 0.5% QD) |
|---|---|---|
| Group 2 | Oxymetazoline 1.0% once-daily | (hereafter referred to as Oxy 1.0% QD) |
| Group 3 | Oxymetazoline 1.5% once-daily | (hereafter referred to as Oxy 1.5% QD) |
| Group 4 | Vehicle once-daily | (hereafter referred to as vehicle QD) |
| Group 5 | Oxymetazoline 0.5% twice-daily | (hereafter referred to as Oxy 0.5% BID) |
| Group 6 | Oxymetazoline 1.0% twice-daily | (hereafter referred to as Oxy 1.0% BID) |
| Group 7 | Oxymetazoline 1.5% twice-daily | (hereafter referred to as Oxy 1.5% BID) |
| Group 8 | Vehicle twice-daily | (hereafter referred to as vehicle BID) |

Each of the 4 different treatments (oxymetazoline 0.5%, 1.0%, 1.5%, or vehicle) was administered once or twice daily for a total of 8 treatment groups. Study site staff and patients knew the regimen (once or twice daily) but did not know the treatment that the patient was receiving. Treatment started after randomization on day 1 at the clinic. The site staff dispensed the study medication to patients and instructed them on how to properly apply the study medication to their face. All patients applied study medication starting on day 1 through the day 28 visit. The patients assigned to groups 1, 2, 3, or 4 were instructed to apply study medication in the morning each day. Patients assigned to groups 5, 6, 7, or 8 were instructed to apply study medication in the morning each day and a second dose approximately 6 to 10 hours later.

3.2 Discussion of Study Design

This study used a randomized and double-blind design to minimize investigator and patient bias. A vehicle-controlled, parallel-group design eliminates many confounding effects that are inherent in other study designs (eg, uncontrolled). Data from clinical studies to date indicate a dose-dependent response for the reduction of facial erythema as reported by scoring on the CEA and SSA scales, a clinician and patient scale, respectively. Although a clear drug effect can be seen after a single dose of oxymetazoline, it is not known to what extent this efficacy may change over 4 weeks of continuous dosing. The peak drug effect was observed 4 hours post-treatment after a single treatment with concentrations up to 1.5% (Study 199201-001). With daily dosing, the peak efficacy as well as maintenance of effective reduction in erythema may change over a 4-week dosing period. This study was designed to assess these changes at oxymetazoline concentrations of 0.5%, 1.0%, and 1.5% administered for 28 consecutive days.

In addition to evaluating the effect of once-daily dosing over a 12-hour observation period, twice-daily dosing was included to study the effect of a second dose during the 12-hour observation period, with the intent to maintain a high level of efficacy over a period of 12 hours.

3.3 Selection of Study Population

The study included patients with moderate to severe facial erythema associated with rosacea. For enrollment into the study, each patient had to meet all of the following inclusion criteria and none of the following exclusion criteria.

3.3.1 Inclusion Criteria

Patients must have met the following inclusion criteria to be enrolled in the study:

male or female, 18 years of age or older moderate to severe facial erythema associated with rosacea, defined as a grade of ≥3 on the Allergan CEA scale with photonumeric guide as assessed by the investigator moderate to severe facial erythema associated with rosacea, defined as either "more redness than I prefer" or "completely unacceptable redness" on the SSA of erythema scale as assessed by the patient stable erythema associated with rosacea, with minimal variation from day to day and within each day, in the opinion of the patient written informed consent had been obtained prior to any study-related procedures written Authorization for Use and Release of Health and Research Study Information ability to follow study instructions and complete study assessment tools without assistance, and was likely to complete all required visits including staying at the investigational site for 3 separate visits that were to last for at least 12 hours 3.3.2 Exclusion Criteria Patients were excluded from the study if they met any of the following exclusion criteria:

any uncontrolled systemic disease any of the following conditions: clinically unstable hypertension, orthostatic hypotension, clinically unstable cerebral insufficiency, coronary insufficiency, cardiac arrhythmia (ie, tachyarrhythmias, advanced ventricular arrhythmias), ischemic heart disease, benign prostate hypertrophy, or Raynaud's syndrome history or current evidence of drug or alcohol abuse within 12 months prior to the screening visit narrow angle glaucoma known hypersensitivity or allergies to any component of the study treatment greater than 3 inflammatory lesions on the face facial acne that may have interfered with study assessments, as determined by the investigator clinical signs of actinic damage (eg, actinic lentigines, mottled hyperpigmentation or hypopigmentation, yellowish discoloration, excessive telangiectasia) on the face that might have interfered with the study evaluations, in the opinion of the investigator any of the following procedures or treatments occurring within the specified period prior to baseline assessments of erythema:

a. 2 hours:
  any topical products including, but not limited to, lotions, creams, ointments, and cosmetics applied to the face (facial cleansers were allowed)

b. 14 days:
  products containing oxymetazoline (eg, eye drops, nasal sprays), topical glucocorticosteroids applied to the face, any prescription or OTC product for the treatment of acne or rosacea, and ANY product to reduce redness to the face c. 28 days:
   systemic antibiotics that were known to have an effect on rosacea
d. 180 days:
   isotretinoin
e. 6 months:
   laser, light-source (eg, intense pulsed light [IPL], photodynamic therapy [PDT]) or other energy-based therapy to the face excessive facial hair, or other facial characteristics that could have made assessments of erythema difficult, as determined by the investigator current use of monoamine oxidase (MAO) inhibitors current use of niacin ≥500 mg/day females who were pregnant, nursing, or planning a pregnancy during the study or who were of childbearing potential not using a reliable method of contraception and/or not willing to maintain a reliable method of contraception during their participation in the study current enrollment in an investigational drug or device study or participation in such a study within 30 days of entry into this study patient had a condition or was in a situation that, in the investigator's opinion, that may have put the patient at significant risk, may have confounded the study results, or may have significantly interfered with the patient's participation in the study patients with a facial photograph that appeared in the Allergan photonumeric guide were not eligible for participation 3.3.3 Removal of Patients from Therapy or Assessment Patients could have voluntarily withdrawn from the study at any time. Additionally, patients could have been discontinued from the study by an investigator for reasons such as adverse events, pregnancy, loss to follow-up, protocol violations, personal reasons, or lack of efficacy as determined by the investigator. The study could have been stopped at the study site(s) at any time by the site investigator(s). Allergan could have stopped the study (study site[s]) with appropriate notification.

If a patient discontinued participation in the study early, every attempt was made to complete all exit study procedures, as indicated in Table 3-2, and an exit form outlining the reason for withdrawal was to be completed. Notification of early patient discontinuation from the study and the reason for discontinuation was made to Allergan and was clearly documented on the appropriate eCRF.

3.4 Treatments 3.4.1 Treatments Administered

Approximately 0.5 grams of oxymetazoline cream 0.5%, 1.0%, 1.5%, or vehicle was to be applied topically to the face by the patient once or twice daily, based on the randomization assignment, for 28 consecutive days.

Patients were instructed to wash their hands before and after each application of study medication. The patient was to apply approximately a pea size amount of study medication on the finger-tip and then dab the cream onto the erythematous area of the face, gently spreading the study medication to thinly cover the entire face (hairline to mandibular ridge and from ear to ear), and taking care not to over apply study medication. A pea size amount of the study medication represented approximately 0.5 grams of the product. Patients were instructed to avoid applying the study medication to the eyes, eyelids, scalp, neck, ears, and any membrane of the inner nose, mouth, lips, or open wounds.

3.4.2 Identity of Investigational Product(s)

Each tube of oxymetazoline hydrochloride 0.5% (Allergan formulation number 11007X, batch number EHC-C), 1.0% (Allergan formulation number 11008X, batch number EHD-C), and 1.5% (Allergan formulation number 11009X, batch number EHE-C) cream contained oxymetazoline HCl, methylparaben, propylparaben, phenoxyethanol, sodium citrate dihydrate, citric acid anhydrous, disodium edetate, butylated hydroxytoluene, anhydrous lanolin, medium chain triglycerides, diisopropyl adipate, oleyl alcohol, polyethylene glycol (PEG)-300, PEG-6 (and) PEG-32 (and) glycol stearate, cetostearyl alcohol, ceteareth-6 (and) stearyl alcohol, ceteareth-25, and purified water.

Each tube of oxymetazoline cream vehicle (Allergan formulation number 11006X, batch number EHB-C) cream contained propylparaben, phenoxyethanol, methylparaben, sodium citrate dihydrate, citric acid anhydrous, disodium edetate, butylated hydroxytoluene, anhydrous lanolin, medium chain triglycerides, diisopropyl adipate, oleyl alcohol, PEG-300, PEG-6 (and) PEG-32 (and) glycol stearate, cetostearyl alcohol, ceteareth-6 (and) stearyl alcohol, ceteareth-25, and purified water.

Formulation characteristics are provided in Table 3-1.

TABLE 3-1

Formulation Characteristics

| Formulation Characteristics | Formulation | | | |
|---|---|---|---|---|
| | Oxy 0.5% | Oxy 1.0% | Oxy 1.5% | Vehicle |
| Strength | 5 mg/g | 10 mg/g | 15 mg/g | 0.0 mg/g |
| Dosage form | Topical Cream | Topical Cream | Topical Cream | Topical Cream |
| Bulk product lot number | EHC-C | EHD-C | EHE-C | EHB-C |
| Potency (% of label claim) | 0.5 | 1.0 | 1.5 | 0.0 |
| Manufacturing site | DPT, San Antonio, TX | DPT, San Antonio, TX | DPT, San Antonio, TX | DPT, San Antonio, TX |
| Manufacturing date | 19 Sep. 2012 | 20 Sep. 2012 | 21 Sep. 2012 | 18 Sep. 2012 |
| Batch size | 32 kg | 32 kg | 27 kg | 32 kg |
| Expiration/retest date | 31 Aug. 2013 | 31 Aug. 2013 | 31 Aug. 2013 | 31 Aug. 2013 |

Oxy = oxymetazoline hydrochlordide;
TX = Texas 3.4.3 Method of Assigning Patients to Treatment Groups Prior to initiation of study treatment, each patient who provided informed consent was assigned a patient number that served as the patient identification number on all study documents throughout the study.

At the time of randomization on day 1, eligible patients were randomized via an automated interactive voice response system/interactive web response system (IVRS/IWRS) that was used to manage the randomization and treatment assignment based on a randomization scheme prepared by Allergan Biostatistics. At each investigational site, eligible patients were randomized to 1 of 8 treatment groups in a 1:1:1:1:1:1:1:1 ratio to receive a once-daily or twice-daily regimen of oxymetazoline 0.5%, 1.0%, 1.5%, or vehicle.

Study medication tubes were labeled with medication kit numbers. At the time of randomization the IVRS/IWRS provided the site with the specific medication kit number(s) for each randomized patient, corresponding to the treatment group assigned via central randomization. Sites dispensed study medication according to the IVRS/IWRS instructions. Sites received the IVRS/IWRS confirmation notifications for each transaction. All notifications were to be maintained with the study source documents.

On day 14, sites called the IVRS or logged onto the IWRS to obtain a kit number to dispense additional study medication to patients randomized to twice-daily dosing groups.

3.4.4 Selection of Doses in the Study

The doses of 0.5%, 1.0% and 1.5% oxymetazoline were selected based on data obtained from nonclinical studies in rats and minipigs in conjunction with data from 4 clinical dermal safety studies (a 21-day cumulative irritation study, a repeat-insult patch test, a phototoxicity study, and a photo contact-allergy study) and 5 clinical studies.

3.4.5 Selection and Timing of Dose for Each Patient

As described in Section 3.2, in addition to evaluating the effect of once-daily dosing over a 12-hour observation period, twice-daily dosing was included to study the effect of a second dose during the 12-hour observation period, with the intent to maintain a high level of efficacy over a period of 12 hours. Based on their randomization assignment, patients were instructed to apply study medication to their face starting on day 1 through the day 28 visit. Patients assigned to group 1, 2, 3, or 4 (once-daily dosing groups) were instructed to apply study medication in the morning each day. Patients assigned to group 5, 6, 7, or 8 (twice-daily dosing groups) were instructed to apply study medication in the morning and a second dose approximately 6 to 10 hours later. On days 1, 2, 14, and 28, all patients were instructed to apply the study medication at the clinic. The morning dose was to be applied after predose study assessments and procedures were complete. Patients in the twice-daily dosing groups were to apply the second (evening dose) 6 hour after the morning dose. On day 2 only the morning dose was to be applied at the clinic.

3.4.6 Blinding

This was a double-blinded clinical trial. Study medications were provided in identical tubes and cartons to maintain study masking. The investigator, investigator staff, and patients were masked to the study medication.

If necessary for the safety and proper treatment of the patients, the investigator was able to unmask the patient's treatment assignment to conduct appropriate follow-up care. Whenever possible, Allergan was to be notified before unmasking the study medication. The date and signature of the person breaking the code as well as the reason for breaking the code and any associated adverse events were to be recorded in the patient's source documentation.

3.4.7 Prior and Concomitant Therapy 3.4.7.1 Permissible Medications/Treatments

Therapy considered necessary for the patient's welfare may have been given at the discretion of the investigator. If the permissibility of a specific medication/treatment was in question, Allergan was to be contacted.

3.4.7.2 Prohibited Medications/Treatments

The decision to administer a prohibited medication/treatment was made with the safety of the study participant as the primary consideration. When possible, Allergan was to be notified before the prohibited medication/treatment was administered.

Prohibited Medications/Treatments:
the application of any facial products (eg, makeup, lotions, or ointments) was prohibited during all study visits from 2 hours before the first assessment and until all assessments were complete. Use of facial products was permitted on all other dosing days; however, they must have been removed at least 20 minutes before drug application and patients must have waited at least 20 minutes after drug application before applying.

products containing oxymetazoline (eg, Afrin®, Vicks Sinex®, Visine L.R.®, Ocuclear®, Zoamet®, Mucinex® nasal spray, Sudafed OM® nasal spray) except for study medication any prescription or OTC product for the treatment of acne or rosacea any prescription or OTC product that caused vasoconstriction or was primarily used to decrease facial redness topical retinoids any topical treatment that may have affected erythema or caused skin irritation new topical facial regimens systemic antibiotics that were known to have an effect on rosacea topical glucocorticosteroids applied to the face any new use of systemic or inhaled glucocorticosteroids MAO inhibitors isotretinoin niacin ≥500 mg/day niacin ≤500 mg/day if not at a stable dose or if it was known to cause flushing systemic alpha-1 adrenergic receptor antagonists (eg, tamsulosin, terazosin, doxazosin, and alfuzosin)

medications that the patient knew may have increased erythema or flushing patients were also to refrain from changing the use of any concomitant therapies after the screening visit until study completion Prohibited Treatments laser light-source (eg, IPL or PDT)

other energy-based therapy to the face

Prohibited Activities 24 Hours Before Study Visits:

consumption of any food or beverage that was known to increase erythema for the patient use of saunas, steam rooms, and hot tubs, or any other activities that were known to increase erythema for the patient 3.4.7.3 Special Diet or Activities Twenty-four hours before the study visits, patients were to avoid any foods, beverages, or activities that were known specifically to them to increase their facial erythema. In addition, patients were instructed to avoid all prohibited medications, treatments, and activities, as described in Section 3.4.7.2.

Patients were instructed to fast (only water was permitted) for at least 10 hours prior to blood collections for laboratory safety tests at screening, day 29, and (if applicable) early exit. If a patient was not fasting at the screening visit, he/she was asked to return to the clinic for laboratory safety tests prior to the day 1 visit.

Patients were to remain at the investigational site for at least 12 hours during days 1, 14, and 28; the study site provided meals and beverages. Patients were to only consume the food and beverages provided by the study staff. The meals provided were not to contain items that may have increased the patients' facial erythema, such as certain spices, caffeine, nicotine, hot beverages, or alcohol. Patients could have consumed water on an ad libitum basis.

3.4.8 Treatment Compliance

The investigator was instructed to keep an accurate accounting of the number of investigational units received from Allergan, dispensed to the patients, the number of units returned to the investigator by the patient, and the number of units returned to Allergan during and at the completion of the study. A detailed inventory was to be completed for the study medication. The study medication was to be dispensed only by an appropriately qualified person to patients in the study. The medication was to be used in accordance with the protocol by patients who were under the direct supervision of an investigator.

All patients were to apply study medication topically to their face for 28 consecutive days. On days 1, 14, and 28, patients applied the study medication at the clinic (1 dose for the once-daily patients and 2 doses for the twice-daily patients). On day 2, patients applied only the morning dose at the clinic. The study medication tubes were weighed predose and postdose for the morning treatment application and postdose after the evening treatment application at each in-clinic treatment visit. The weights were recorded on source documentation.

3.5 Efficacy, Health Outcomes, Drug Concentration, Safety, and Other Measurements The study included scheduled visits at screening (days −30 to −2), randomization day 1, treatment period visits (days 2, 14, and 28), follow-up (days 29 and 35), and exit (day 56). The schedule of visits and the study variables evaluated at each visit are presented in Table 3-2. Evaluations were to be performed by the same evaluator throughout the study whenever possible. If it was not possible to use the same evaluator to follow the patient, then evaluations were to overlap for at least 1 visit.

Efficacy Measurements 3.5.1.1 Primary Efficacy Measurements

Efficacy measures were:
investigator's assessment of the severity of facial erythema using the CEA scale with photonumeric guide
patient's assessment of the severity of facial erythema using the SSA scale The CEA and SSA scales are shown below.

CEA Scale

| Grade | Description |
|---|---|
| 0 | Clear skin with no signs of erythema[a] |
| 1 | Almost clear of erythema, slight redness |
| 2 | Mild erythema, definite redness |
| 3 | Moderate erythema, marked redness |
| 4 | Severe erythema, fiery redness |

[a]Normal healthy skin color as seen in individuals without rosacea

SSA Scale

| Grade | Description |
|---|---|
| 0 | Clear of unwanted redness |
| 1 | Nearly clear of unwanted redness |
| 2 | Somewhat more redness than I prefer |
| 3 | More redness than I prefer |
| 4 | Completely unacceptable redness |

Primary Efficacy Variable:

The primary efficacy variable was derived from the efficacy measures: the investigator's assessment of the severity of facial erythema using the 5-point CEA scale with photonumeric guide and the patient's assessment of the severity of facial erythema using the 5-point SSA scale.

The primary efficacy variable was defined as a treatment responder at hours 2, 4, 6, 8, 10, and 12 on day 28. A responder was defined as at least a 2-grade improvement from baseline on both CEA and SSA. The baseline value was the value collected on day 1 predose (baseline). If day 1 predose data were missing, screening visit data was used.

3.5.1.2 Secondary Efficacy Measurements

The secondary efficacy variables were defined as follows:
proportion of patients with at least a 2-grade decrease (improvement) on both CEA and SSA from baseline at hour 0.5 postdose on day 28
proportion of patients with at least a 2-grade decrease (improvement) on both CEA and SSA from baseline at hour 1 postdose on day 28

3.5.1.3 Other Efficacy Measurements

An additional efficacy measure was included in this study as an exploratory measure to assess the patient's perception of facial erythema (using different response options/categories of erythema than the SSA) for potential use in future studies.

the patient's assessment of the severity of facial erythema as measured by the Subject Self-Assessment for Rosacea Facial Redness (referred to as SSA-2), which included a photoguide The SSA-2 is similar to the SSA in that it is a 5-point patient assessment of facial redness from a score of 0 (clear) to 4 (severe); however, patients use a photoguide (similar to the CEA photonumeric guide) to complete their assessments.

3.5.2 Health Outcomes Measurements

The following patient-reported outcome (PRO) measures were included in this study as exploratory measures to assess treatment responsiveness and determine an appropriate responder definition for use in future studies:

the patient's assessment of symptoms associated with erythema as measured by the Symptom Assessment for Rosacea Facial Redness (hereafter referred to as Symptom Assessment)

the patient's assessment of functional impacts (eg, emotional, social) associated with erythema as measured by the Impact Assessment for Rosacea Facial Redness (hereafter referred to as Impact Assessment)

the patient's assessment of satisfaction with treatment as measured by the Satisfaction Assessment for Rosacea Facial Redness (baseline and follow-up versions) (hereafter referred to as Satisfaction Assessment)

Response options for each question in the PROs were on 5-point adjectival and/or Likert-type scales.

3.5.3 Drug Concentration Measurements

Blood samples were collected from all patients to determine oxymetazoline concentrations in plasma at the following timepoints:

Day 1: predose, 2, 4, 6 (before evening dose for twice-daily groups), 8, 10, and 12 hours after morning dose
Day 2: predose (24 hours after day 1 morning dose)
Day 14: predose, 6 (before evening dose for twice-daily groups) and 12 hours after morning dose
Day 28: predose, 2, 4, 6 (before evening dose for twice-daily groups), 8, 10, and 12 hours after morning dose
Day 29: 24 hours after day 28 morning dose
Day 35: after all assessments were completed At the selected timepoints, approximately 6 mL of blood was collected into prelabeled $K_2$EDTA lavender top blood collection tubes and gently inverted at least 10 times to ensure adequate mixing of blood and anticoagulant. The tubes were immediately placed in an ice water bath for at least 5 minutes and then centrifuged (refrigerated at 4° C.) for 10 minutes at approximately 2,000×g (~2,500 rates per minute). A minimum of 1.0 mL of the harvested plasma was transferred into 2 prelabeled cryovials and stored at −20° C. or below until analyzed. The samples were analyzed using a validated high performance liquid chromatography-tandem mass spectrometry (LC-MS/MS) method with a lower limit of quantitation (LLOQ) of 10 pg/mL.

3.5.4 Other Measurements 3.5.4.1 Clinician Telangiectasia Assessment

The Clinician Telangiectasia Assessment (CTA) was the investigator's assessment of the average overall severity of telangiectasia on the application sites of the patient's face. The CTA was performed by the investigator at specified timepoints at screening, days 1, 14, 28, 29, 35, and 56/study exit (Table 3-2). The assessments were not to be compared with CTA assessments at any other timepoint. The investigator was not to refer to any other evaluation to assist with these assessments.

The CTA was performed based on the following scale:

| | Description |
|---|---|
| 0 | Clear skin with no signs of telangiectasia |
| 1 | Almost clear, a few barely visible telangiectasia |
| 2 | Mild, a few visible telangiectasia |
| 3 | Moderate, with the presence of clearly visible telangiectasia |
| 4 | Severe, with the presence of many visible telangiectasia |

3.5.4.2 Lesion Count

Lesion count of the face was done by the investigator at screening, predose on days 1, 14, and 28, and days 35 and 56/study exit.

3.5.4.3 Aesthetic Questionnaire

The Aesthetic Questionnaire (AQ) was administered to patients on days 14 and 28 and assessed patient's facial skin type, other medication used to treat rosacea, ease of application, smell, speed of drying, greasiness/stickiness, moisturizing effect, glossy/shiny appearance, residue, and any effect of treatment on routine application of makeup or sunscreen.

3.5.4.4 Standardized Photography

Canfield Scientific, Inc. (Fairfield, N.J.) provided instructions for taking photographs and processing digital photographs. Each site received instructions and training on taking photographs.

Facial photographs were to be taken for all patients. Photographs of patients in treatment groups 1, 2, 3, and 4 (once-daily dosing) taken at predose and 6 and 12 hours postdose on days 1, 14, and 28, and day 35 were used for exploratory digital image analysis (DIA) related to erythema. Three views (ie, right view, frontal view, and left view) of photographs were taken for patients at each timepoint.

3.5.5 Safety Measurements

Safety measurements included adverse events, facial dermal tolerability assessment, 12-lead ECG, fasting biochemistry and hematology, urinalysis, urine pregnancy tests for women of childbearing potential, physical examination, and vital sign measurements (blood pressure, pulse rate, respiratory rates, and body temperature).

3.5.5.1 Adverse Events

An adverse event was defined as any untoward medical occurrence in a patient administered a pharmaceutical product and that did not necessarily have a causal relationship with study treatment. An adverse event could therefore be any unfavorable and unintended sign (including an abnormal laboratory finding), symptom, or disease temporally associated with the use of a medicinal (investigational) product, whether or not related to the medicinal (investigational) product. In addition, during the screening period, adverse events were assessed regardless of the administration of a pharmaceutical product.

Adverse events were assessed and documented, as appropriate, throughout the study (ie, after informed consent had been obtained). At each visit, the investigator began by querying for adverse events by asking each patient a general, non-directed question such as "How have you been feeling since the last visit?" Directed questioning and examination were then done as appropriate. All reported adverse events were documented on the appropriate eCRF.

3.5.5.1.1 Serious Adverse Events

A serious adverse event was defined as any adverse event occurring at any dose that resulted in any of the following outcomes: death, a life-threatening adverse event, inpatient hospitalization or prolongation of existing hospitalization, a persistent or significant disability/incapacity, or a congenital anomaly/birth defect. Important medical events that may not have resulted in death, been life-threatening, or required hospitalization could have been considered a serious adverse event when, based upon appropriate medical judgment, they may have jeopardize the patient and may have required medical or surgical intervention to prevent one of the outcomes listed in this definition.

Note: Allergan considers all cancer adverse events as serious adverse events. In addition, Allergan considers any abortion (spontaneous or elective) as a serious adverse event.

3.5.5.1.2 Severity

A clinical determination was made of the intensity of an adverse event. The severity assessment for a clinical adverse event was completed using the following definitions as guidelines:

| | |
|---|---|
| Mild | Awareness of sign or symptom, but easily tolerated. |
| Moderate | Discomfort enough to cause interference with usual activity. |
| Severe | Incapacitating with inability to work or do usual activity. |
| Not applicable | In some cases, an adverse event may have been an 'all or nothing' finding that could not be graded. |

3.5.5.1.3 Relationship to Study Drug or Study Procedure

A determination was made of the relationship (if any) between an adverse event and the study drug or study procedure, as applicable. A causal relationship was present if a determination was made that there was a reasonable possibility that the adverse event may have been caused by the drug or study procedure.

3.5.5.1.4 Procedures for Reporting Adverse Events

Any adverse event was to be recorded on the appropriate eCRF.

All adverse events that were drug-related and unexpected (not listed as treatment-related in the current Investigator's Brochure) were to be reported to the governing IRB as required by the IRB, local regulations, and the governing health authorities. Any adverse event that was marked "ongoing" at the exit visit was to be followed-up as appropriate.

3.5.5.1.5 Procedures for Reporting a Serious Adverse Event

Any serious adverse event occurring during the study period (beginning with informed consent) and for at least 28 days after the last dose of study drug was to be immediately reported to an Allergan representative listed on the Allergan personnel page and recorded on the serious adverse event fax form. All patients with a serious adverse event were to be followed up and the outcomes reported. The investigator was required to supply Allergan and the IRB with any additional requested information (eg, autopsy reports and terminal medical reports).

3.5.5.2 Facial Dermal Tolerability Assessment

Facial dermal tolerability assessments were evaluated by investigators and patients at specified timepoints on days 1, 2, 14, 28, 35, and 56/study exit. Facial dermal tolerability assessment included the investigator's assessments (dryness and scaling of the treatment area) and the patient's assessments (stinging/burning and pruritus [itching] of skin in the application area) as described below:

Investigator's assessments: dryness and scaling of the treatment area

Dryness: skin roughness

| | |
|---|---|
| None (0) | No dryness |
| Mild (1) | Slight but definite roughness |
| Moderate (2) | Moderate roughness |
| Severe (3) | Marked roughness |

Scaling: abnormal peeling of the stratum corneum

| | |
|---|---|
| None (0) | No dryness |
| Mild (1) | Barely perceptible peeling, noticeable only on light scratching or rubbing |
| Moderate (2) | Obvious but not profuse peeling |
| Severe (3) | Heavy scale production |

Patient's assessments: stinging/burning and pruritus (itching) of skin in the application area The investigator asked the patient if he/she was experiencing stinging/burning and/or pruritus (itching) based on the scale below.

Stinging/Burning: prickling pain sensation

| | |
|---|---|
| None (0) | No stinging/burning |
| Mild (1) | Slight warm, tingling/stinging sensation; not really bothersome |
| Moderate (2) | Definite warm, tingling/stinging sensation that is somewhat bothersome |
| Severe (3) | Hot, tingling/stinging sensation that has caused definite discomfort |

Pruritus: itching in the application area

| | |
|---|---|
| None (0) | Normal, no itching in the application area |
| Mild (1) | Noticeable discomfort causing intermittent awareness |
| Moderate (2) | Noticeable discomfort causing continuous awareness |
| Severe (3) | Definite, continuous discomfort interfering with normal daily activities |

3.5.5.3 Physical Examination

The investigator examined the patient for any physical abnormalities at screening and study exit for the following body systems: general appearance, head, eyes, ears, nose, throat, heart/cardiovascular, lungs, abdomen, neurologic, extremities, back, musculoskeletal, lymphatic, skin, and other findings. The patient's height and weight were recorded at screening only.

3.5.5.4 Vital Signs

Vital signs including pulse rate, systolic and diastolic blood pressures, respiratory rate, and temperature were recorded at screening and days 1, 2, 14, 28, 35, and 56/study exit.

3.5.5.5 Clinical Laboratory Evaluations

Patients had samples of blood (fasting) and urine collected at screening, day 29, and day 56/study exit visits, as specified by the central laboratory, and used for the following tests:

Hematology: complete blood count including hemoglobin, hematocrit, red blood cells, white blood cells, red blood cell morphology, mean corpuscular volume, mean corpuscular hemoglobin, mean corpuscular hemoglobin concentration, white blood cell differential (% and absolute), neutrophils, lymphocytes, monocytes, basophils, eosinophils and platelets Chemistry: glucose, creatinine, blood urea nitrogen, total bilirubin, aspartate aminotransferase (serum glutamic oxaloacetic transaminase), alanine aminotransferase (serum glutamic pyruvic transaminase), alkaline phosphatase, uric acid, sodium, potassium, bicarbonate (carbon dioxide content), chloride, phosphorus, calcium, total protein, albumin, and lactate dehydrogenase Urinalysis: specific gravity, pH, color, protein, glucose, blood ketones, bilirubin, and microscopic examination

3.5.5.6 12-Lead ECGs 12-lead ECGs were performed at screening, day 1/baseline, and day 28 using standardized equipment and electrode placement. A qualified third party vendor (eResearch Technology [ERT]) read the ECGs and reported the findings as normal, abnormal, or unable to evaluate. For screening ECGs, prespecified significant abnormal findings were flagged as exclusion alerts, and generated an exclusion alert for the site and sponsor. For all subsequent ECGs, ERT also reported the appearance of any new, prespecified significant abnormal findings and generated a protocol alert for the site and sponsor. The cardiologists were blinded to patient treatment assignments.

3.5.5.7 Urine Pregnancy Test

Urine pregnancy tests were performed on females of childbearing potential at screening, prior to dosing at day 1/baseline, day 35, and at study exit (or early discontinuation visit). Further urinary pregnancy tests could be performed at any time during the study at the discretion of the investigator. A negative result was required prior to receiving study medication.

If a patient became pregnant during the study, the investigator was required to notify Allergan immediately after the pregnancy was confirmed and the patient was exited from the study after appropriate safety follow-up. The investigator was required to notify the patient's physician that the patient may have been treated with an investigational medication (oxymetazoline or vehicle), follow the progress of the pregnancy to term, and document the outcome of the pregnancy.

3.5.6 Appropriateness of Measurements

The primary efficacy measures in this study were assessed by using the CEA scale with photonumeric guide and the SSA scale.

The CEA was developed by Allergan and validated in a single-center study (Study 199201-003) with 104 patients representing all 5 CEA scale grades. Seven physician raters rated all subjects on the severity of their erythema using the 5-point CEA scale with photonumeric guide. The erythema assessment and ratings on day 1 were performed twice, at least 2 hours apart. Based on the weighted Kappa statistic there was "substantial" agreement for all 7 of the raters. The overall weighted Kappa statistic was 0.752, which was "substantial" agreement. The overall Kendall statistic was 0.908 which was deemed "almost perfect" agreement among raters. The data demonstrated that the CEA scale with photonumeric guide is a reliable instrument for grading the degree of facial erythema associated with rosacea.

The SSA tool has been derived from a similar tool used in Galderma studies called the Patient Self Assessment. Allergan has further developed the SSA instrument in accordance with the FDA PRO Guidance to test its content validity. Modifications were made to the SSA based on additional development and it was renamed Subject Self-Assessment for Rosacea Facial Redness (referred to in this study as SSA-2). The SSA-2 is a single item rating scale designed for subject assessment of severity of facial erythema in the present moment. The content validity of the SSA-2 (including the relevance of its content and ability of patients to understand and use the instrument) was supported in a qualitative study (AL6749A). In this same study, the content validity of the CEA photoguide was also evaluated for subject use with the SSA-2 and was shown to be valid. Psychometric properties of both the SSA and SSA-2 with photoguide will be assessed in the oxymetazoline clinical development program.

The safety measurements in this study are standard measures in clinical research and are recognized as reliable, accurate, and relevant for this therapeutic area.

The pharmacokinetic parameters reported in this study are the accepted standard recognized globally by scientists and regulatory authorities.

3.5.7 Schedule of Assessments

The frequency and timing of study visits and measurements are outlined in Table 3-2. Additional examinations were to be performed as necessary to ensure the safety and well-being of patients during the study.

TABLE 3-2

Schedule of Visits and Procedures

| Study Procedures | Visit 1 Screening Day −30 to −2 | Visit 2 Day 1/ Baseline ±0 Day ≥12 hrs in clinic | Visit 3 Day 2 ±0 Day | Visit 4 Day 14 Visit Window ±3 Days ≥12 hrs in clinic | Visit 5 Day 28 ±3 Days ≥12 hrs in clinic | Visit 6 Day 29 Follow-up ±0 Day | Visit 7 Day 35 Follow-up ±3 Days | Visit 8 Day 56/ Exit ±3 Days |
|---|---|---|---|---|---|---|---|---|
| Consent/Authorization | X | | | | | | | |
| Demographics | X | | | | | | | |
| Inclusion/Exclusion Criteria | X | predose | | | | | | |
| Facial Photographs[a] | X | predose, 6 and 12 hrs | | predose, 6 and 12 hrs | predose, 6 and 12 hrs | | X | X |
| Subject Self-Assessment (SSA) of Erythema Scale[a] | X | predose, 0.5, 1, 2, 4, 6, 8, 10, and 12 hrs | predose | predose, 0.5, 1, 2, 4, 6, 8, 10, and 12 hrs | predose, 0.5, 1, 2, 4, 6, 8, 10, and 12 hrs | X | X | X |
| Subject Self-Assessment for Rosacea Facial Redness (SSA-2)[a] | X | predose, 0.5, 1, 2, 4, 6, 8, 10, and 12 hrs | predose | predose, 0.5, 1, 2, 4, 6, 8, 10, and 12 hrs | predose, 0.5, 1, 2, 4, 6, 8, 10, and 12 hrs | X | X | X |
| Patient-reported Outcomes (PROs) Aesthetic Questionnaire (AQ) | | predose | | predose X | predose X | | X | X |
| Clinician Erythema Assessment (CEA)[a] | X | predose, 0.5, 1, 2, 4, 6, 8, 10, and 12 hrs | predose | predose, 0.5, 1, 2, 4, 6, 8, 10, and 12 hrs | predose, 0.5, 1, 2, 4, 6, 8, 10, and 12 hrs | X | X | X |
| Clinician Telangiectasia Assessment (CTA)[a] | X | predose, 4, 8, and 12 hrs | | predose, 4, 8, and 12 hrs | predose, 4, 8, and 12 hrs | X | X | X |
| Lesion Count | X | predose | | predose | predose | | X | X |
| Facial Dermal Tolerability Assessment (Patient and Investigator)[a] | | predose, 1, 2, 4, 6, 8, 10, and 12 hrs | predose | predose, 1, 2, 4, 6, 8, 10, and 12 hrs | predose, 1, 2, 4, 6, 8, 10, and 12 hrs | | X | X |
| Medical History | X | predose | | | | | | |
| Height and Weight | X | | | | | | | |
| Vital Signs Measurements | X | predose and 12 hrs | predose | predose and 12 hrs | predose and 12 hrs | | X | X |
| Physical Examination | X | | | | | | | X |
| Electrocardiogram (ECG)[a] | X | predose, 6 and 12 hrs | | | predose, 6 and 12 hrs | | | |
| Blood Sample for Fasting Biochemistry, Hematology[c]; Urine Sample for Urinalysis | X | | | | | X | | X[b] |
| Pharmacokinetic Sample[a,c] | | predose, 2, 4, 6, 8, 10, and 12 hrs | predose | predose, 6 and 12 hrs | predose, 2, 4, 6, 8, 10, and 12 hrs | 24 hrs after day 28 morning dose | X | |
| Pregnancy Test (Urine) | X | predose | | | | | X | X |
| Randomization | | X | | | | | | |
| Dispense Study Medication | | QD and BID groups | | BID group | | | | |

TABLE 3-2-continued

Schedule of Visits and Procedures

| | Visit Number | | | | | | | |
|---|---|---|---|---|---|---|---|---|
| | Visit 1 | Visit 2 | Visit 3 | Visit 4 | Visit 5 | Visit 6 | Visit 7 | Visit 8 |
| | | | | Visit | | | | |
| | Screening | Day 1/ Baseline | Day 2 | Day 14 Visit Window | Day 28 | Day 29 Follow-up | Day 35 Follow-up | Day 56/ Exit |
| Study Procedures | Day −30 to −2 | ±0 Day ≥12 hrs in clinic | ±0 Day | ±3 Days ≥12 hrs in clinic | ±3 Days ≥12 hrs in clinic | ±0 Day | ±3 Days | ±3 Days |
| Weigh Study Medication Tube | | morning: predose and postdose evening: postdose | morning: predose and postdose | morning: predose and postdose evening: postdose | morning: predose and postdose evening: postdose | | | |
| Dosing (days 1-28) | | X | X | X | X | | | |
| Concomitant Medications and Concurrent Procedures | X | X | X | X | X | X | X | X |
| Adverse Events | X | X | X | X | X | X | X | X |

BID = twice daily dosing (groups 5, 6, 7, and 8);
QD = once daily dosing (groups 1, 2, 3, and 4)
[a]For the twice-daily groups 5, 6, 7, and 8, all assessments at the 6-hour timepoint were to be performed before the evening dose at 6 hours.
[b]Only required for patients who discontinued prior to the day 29 visit
[c]Blood draws were always to occur after the SSA, SSA-2, and CEA assessments had been completed at all timepoints.

3.6 Data Quality Assurance 3.6.1 Study Monitoring

Allergan monitored the sites regularly during the study to assure protocol adherence, proper eCRF and source documentation completion and retention, accurate study drug accountability, and was in frequent contact through verbal and written communication. The Allergan monitor had access to all documents related to the study and the individual participants at any time these were requested. All essential documents were submitted to Allergan and copies retained at the study sites. Portable document format (PDF) copies of the eCRFs were distributed to each site for archival at the end of the study.

3.6.2 Investigator Meetings and Staff Training

Allergan sponsored an investigators training meeting to discuss the protocol procedures and conduct training on study requirements. Training was also conducted via a training portal. CEA training was conducted using live patients with/without rosacea, and with varying severity of erythema. A study initiation visit by the Allergan monitor was performed at all sites prior to the start of the study to review the study protocol in detail and ensure the availability of appropriate study personnel and compliance with GCP regulations and procedures. In addition, for those investigators who were unable to attend the investigator meeting, along with the Allergan monitor, additional Allergan clinical research personnel conducted onsite investigator training.

3.6.3 Clinical Data Management

Clinical Data Management personnel received, processed, and reviewed all data following Allergan Standard Operating Procedures (SOPs).

Study data entered into the electronic data capture (EDC) tool (Oracle InForm version 5.0) by the investigational site personnel was transferred to Allergan Clinical Data Management through validated and secured methods. Other data sources included Perceptive Informatics (used to assign subject, randomization, and medication kit numbers, and to manage medication), Covance Central Laboratory Services (used to analyze blood and urine samples collected during the study including pharmacokinetic data), eResearch Technologies (used to review digital ECG recordings), and Canfield Scientific, Inc. (used to conduct DIA of facial photographs).

The study specific Data Management Plan (DMP) defined data sources and the data review strategy that was applied for this study. The data review strategy ensured consistency, integrity, logical completeness and coding of collected data. Queries were generated within the EDC tool for all discrepancies requiring investigational site follow-up. Any necessary data corrections in EDC were made by the investigational site personnel and verified by Allergan Clinical Data Management. Any necessary data corrections for other data sources were authorized by the investigational site personnel and applied by the respective vendors.

Details and timing of any additional quality assessments carried out for the study were also captured within the study specific DMP.

Following completion of all data review activities, records within the EDC tool were locked and transferred to Allergan Clinical Data Management.

3.6.4 Clinical Quality Assurance Audits

An independent internal Quality Assurance unit conducted audits of randomly selected investigators and clinical data. During these audits, the study was assessed for compliance with the FDA's GCP regulations and guidelines, International Conference on Harmonisation (ICH) guidelines for GCP Topic E6, and applicable SOPs.

3.6.5 Investigational Site Procedures

Quality assurance activities provided by the investigational staff included eCRF review for accuracy and completeness and study medication accounting. Study center personnel were responsible for timely processing of eCRFs, data clarifications, and sending corrections to Allergan.

3.6.6 Laboratory Procedures

A central laboratory, Covance Central Laboratory Services, was used to analyze blood, urine, and plasma samples. This central clinical laboratory is licensed under the Clinical Laboratory Improvement Amendments and accredited by the College of American Pathology.

All blood samples drawn for pharmacokinetic analysis were stored at Covance Central Laboratory Services (Indianapolis, Ind.) until shipment to the Covance bioanalytical laboratory (Indianapolis, Ind.). Blood was assayed for oxymetazoline concentrations in plasma using a validated high performance LC-MS/MS method. The bioanalysis of human plasma oxymetazoline concentrations for this study was conducted in compliance with the US FDA "Guidance for Industry: Bioanalytical Method Validation" dated May 2001. The pharmacokinetic data analysis of this study was conducted according to applicable GCP and pertinent FDA/ICH guidelines.

3.6.7 Bioanalytical Methodology

All plasma samples collected for pharmacokinetic analysis were stored at Covance Central Laboratory Services (Indianapolis, Ind.) until shipment to the Covance Bioanalytical Services, LLC (Indianapolis, Ind.). Plasma was assayed for oxymetazoline concentrations using a validated LC-MS/MS method with an LLOQ of 10 pg/mL.

The treatment randomization code was released to Covance Bioanalytical Services in order to analyze patients on active treatment only.

The bioanalysis of human plasma oxymetazoline concentrations for this study was conducted in compliance with Covance Standard Operating Procedures and in accordance with Guidelines on Good Clinical Practice, ICH E6. The pharmacokinetic data analysis of this study was conducted according to applicable GCP and pertinent FDA/ICH guidelines.

3.6.8 Pharmacokinetic Data Handling and Storage

All electronic files were stored and archived on dedicated Allergan servers. Bioanalytical data files from the bioanalytical laboratories were provided to Allergan's Data Management and Programming group via secure File Transfer Protocol and followed the agreed-upon Data Transfer Agreement. A final analysis dataset was provided to Allergan's Pharmacokinetics and Drug Disposition Department from Allergan's Data Management Department via UNIX. Refer to the Pharmacokinetic Data Analysis Plan for details.

3.7 Statistical and Data Analysis Methods and Determination of Sample Size

A statistical analysis plan that expanded the statistical section of the protocol was approved prior to locking the database. The plan, comprising text with table and listing shells, contained a detailed description of methods to analyze data collected in the study. Ad hoc analyses are summarized in Section 3.8. Information on the pharmacokinetic analyses can be found in the Pharmacokinetic Data Analysis Plan and are summarized below.

3.7.1 Statistical and Analytical Plans
3.7.1.1 Analysis Populations
Three populations were utilized:
  the modified intent-to-treat (mITT) population consisted of all randomized patients who applied study medication during the study, and had both CEA and SSA measurements at baseline (ie, predose on day 1) and at least one post-baseline measurement for both CEA and SSA.
  the per protocol (PP) population consisted of randomized patients with no major protocol violation during the study. The PP population was determined prior to database lock.
  the safety population consisted of patients who applied at least 1 dose of study medication in the study.

If a patient received an incorrect study medication other than intended study medication as randomized, the analysis of that patient's data was based on the actual treatment received at baseline visit for the safety and PP analyses and the randomized assignment for the mITT analyses.

Efficacy analyses were performed on the mITT population as the primary population. Primary efficacy analyses were also performed on the PP population. Safety analyses were based on the safety population.

Missing data were imputed using the last observation carried forward (LOCF) method for the mITT population. No imputation was made for the PP and Safety populations.

3.7.1.2 Primary Efficacy Analysis

The primary efficacy variable was defined as a treatment responder at hours 2, 4, 6, 8, 10, and 12 on day 28. A responder was defined as at least a 2-grade improvement from baseline on both CEA and SSA. The baseline value was the value collected on day 1 predose (baseline). If day 1 predose data were missing, screening visit data were used.

The hypotheses were as follows:

Null hypothesis: Oxy 0.5% QD and vehicle QD were equally effective in reducing erythema over a 12-hour time period on day 28 as measured by patients with at least a 2-grade decrease (improvement) from baseline in both CEA and SSA at hours 2, 4, 6, 8, 10, and 12.

Alternative hypothesis: Oxy 0.5% QD and vehicle QD were not equally effective.

The same hypotheses as stated above were formulated to compare the following groups:
  Oxy 0.5% BID versus vehicle BID
  Oxy 1.0% QD versus vehicle QD
  Oxy 1.0% BID versus vehicle BID
  Oxy 1.5% QD versus vehicle QD
  Oxy 1.5% BID versus vehicle BID A generalized linear model with a logit link function and exchangeable covariance structure using generalized estimation equations (GEE) was performed to analyze the primary variable at hours 2, 4, 6, 8, 10, and 12 on day 28 to compare treatment difference (ie, Oxy 0.5% QD versus vehicle QD, Oxy 1.0% QD versus vehicle QD, and Oxy 1.5% QD versus vehicle QD, separately). The model included fixed effects of treatment group and timepoints. If there was no responder in the vehicle arm at all timepoints that could have caused inconvergence, imputations were made for 1 vehicle patient to be a responder at hour 2 to perform the analysis.

Similar analyses were performed to compare each oxymetazoline twice-daily treatment group to the vehicle twice-daily group.

The analyses were performed on both the mITT and PP populations.

3.7.1.3 Secondary Efficacy Analysis

The secondary efficacy variables were defined as follows: the proportion of patients with at least a 2-grade decrease (improvement) on both CEA and SSA from baseline at hour 0.5 post-dose on day 28; and the proportion of patients with at least a 2-grade decrease (improvement) on both CEA and SSA from baseline at hour 1 post-dose on day 28.

A frequency distribution of patients with at least a 2-grade decrease (improvement) on both CEA and SSA by timepoint (hours 0.5 and 1) on day 28 and treatment group was tabulated. A 2-sided 90% confidence interval (CI) for the treatment difference (ie, each active treatment minus vehicle) by timepoint was provided using a normal approximation method. A Pearson's chi-square test was used to test the treatment difference. If 25% or more of the cells had expected counts less than 5, a Fisher's exact test was used. The same analyses were performed for days 1 and 14.

In addition, a frequency distribution of primary variable by treatment group was tabulated. A 2-sided 90% CI for the treatment difference (ie, Oxy 0.5% QD minus vehicle QD, Oxy 1.0% QD minus vehicle QD, Oxy 1.5% QD minus vehicle QD, separately) of primary variable was provided using a normal approximation method.

The same statistical method used in the primary efficacy analysis was used to analyze the primary variable between 2 active treatment groups (eg, Oxy 1.5% QD versus Oxy 0.5% QD).

The same analyses were performed for the difference between 2 active twice-daily treatment groups and for the difference between one once-daily and one twice-daily treatment group (eg, Oxy 0.5% BID and Oxy 1.0% QD).

3.7.1.4 Other Efficacy Analyses

Other efficacy variables were defined as follows:
proportion of patients with at least a 2-grade decrease (improvement) on both CEA and SSA from baseline at hours 2, 4, 6, 8, 10, and 12 on day 14
proportion of patients with at least a 2-grade decrease (improvement) on both CEA and SSA from baseline at hours 2, 4, 6, 8, 10, and 12 on day 1
proportion of patients with at least a 1-grade decrease (improvement) on both CEA and SSA from baseline at hours 2, 4, 6, 8, 10, and 12 on day 1. The same definition was used for days 14 and 28
proportion of patients with at least a 1-grade decrease (improvement) on CEA from baseline at hours 2, 4, 6, 8, 10, and 12 on day 1. The same definition was used for days 14 and 28.
proportion of patients with at least a 1-grade decrease (improvement) on SSA from baseline at hours 2, 4, 6, 8, 10, and 12 on day 1. The same definition was used for days 14 and 28.
proportion of patients with at least a 1-grade improvement on each question of the PRO from baseline on day 28. The PRO measures were:
Symptom Assessment for Rosacea Facial Redness
Impact Assessment for Rosacea Facial Redness
Satisfaction Assessment for Rosacea Facial Redness The same statistical method used for the primary variable was used for all other efficacy variables, except for PRO variables. For the PRO variables, frequency distributions of the PRO variables were tabulated by visit. A 2-sided 90% CI for the treatment difference (ie, each active treatment group minus vehicle group) was provided using a normal approximation method. A Pearson's chi-square test was used to test the treatment difference. If 25% or more of the cells have expected counts less than 5, a Fisher's exact test was used. Raw PRO data was summarized using a frequency distribution by treatment group and visit. The number of patients with at least a 1-grade improvement in each PRO question and number of patients who reported "very satisfied/satisfied" versus "neither satisfied nor dissatisfied/dissatisfied/very dissatisfied" was analyzed in the same manner.

Raw data and change from baseline in CEA, SSA, and PRO questions were summarized using descriptive statistics by timepoint and treatment group. Frequency distributions were used to summarize raw CEA, SSA, and PRO data by treatment group.

3.7.1.5 Pharmacokinetic Analysis 3.7.1.5.1 Treatment of Below the Lower Limit of Quantitation Data For descriptive statistics of oxymetazoline plasma concentrations, the below the lower limit of quantitation (BLQ) values were set to zero and calculation of mean concentrations in the presence of BLQ value(s) were performed according to SOP DSEPK-002.

3.7.1.5.2 Pharmacokinetic Parameters

The calculation of pharmacokinetic parameters and graphing was performed using Phoenix WinNonlin 6.3 (Moutain View, Calif.). Data cleaning, management, and summary statistics were performed using SAS for Windows Version 9.2 (Cary, N.C.). The following pharmacokinetic parameters were calculated using a non-compartmental analysis, whenever possible:

$C_{max}$=maximum observed plasma concentration
$T_{max}$=time corresponding to maximum observed plasma concentration
$AUC_{0-t}$=Area under the plasma concentration-time curve from time 0 to time t
$R_O$=accumulation ratio calculated as $$\frac{AUC_{0-\tau(DAY\,28)}}{AUC_{0-\tau(DAY\,1)}}$$

where $\tau$ represents the dosing interval
$T_{eff}$=effective half-life calculated as $$\frac{\ln 0.5 \times \tau}{\ln\left(1-\frac{1}{R_0}\right)}$$

where $\tau$ represents the dosing interval 3.7.1.5.3 Statistical Analysis

Descriptive statistics (mean, standard deviation, etc.) were calculated for plasma oxymetazoline concentrations and for the calculated pharmacokinetic parameters.

3.7.1.6 Other Measures Analyses 3.7.1.6.1 Subject Self-Assessment for Rosacea Facial Redness Subject self-assessment for rosacea facial redness (SSA-2) was administered at the same timepoints as the SSA and CEA. All analyses performed for the SSA were performed for the SSA-2.

In addition, a paired t-test was used to compare change from baseline in SSA and SSA-2 by timepoint and treatment group. Analysis of the correlation was performed based on pooled treatment groups at each timepoint and all timepoints combined using a Spearman correlation coefficient and its 90% CI. The analyses included raw data between CEA and SSA, between CEA and SSA-2, and between SSA and SSA-2. The same analyses were performed for change from baseline data.

3.7.1.6.2 Clinician Telangiectasia Assessment

Clinician Telangiectasia Assessment (CTA) was performed by the investigator per the timepoints specified in Table 3-2. A frequency distribution of the CTA was performed by treatment group, and timepoint. A shift table of each category at baseline was compared to those at each scheduled timepoint/visit. Baseline was defined as the pre-dose measurement on day 1. If the day-1 data were not available, the screening data were used as baseline.

3.7.1.6.3 Lesion Count

Lesion count of the face was performed by the investigator at screening, days 1, 14, 28, 35, and 56. Analysis of change from baseline on the lesion count was performed using descriptive statistics. Baseline was defined as the predose measurement on day 1. If the day −1 data were not available, the screening data were used as baseline. Raw data were summarized by descriptive statistics by treatment group.

3.7.1.6.4 Aesthetic Questionnaire

All questions of the AQ were assessed on day 14 and the questionnaire about the characteristics of the study medication was assessed again on day 28. Frequency distributions were used for all questions in the AQ. Questions 6a and 6c on day 14, and questions on day 28 were dichotomized by pooling scale from 1 to 4 as one group (such as "not important" or "less favorable") and 5 to 9 as a separate group (such as "more important" or "more favorable") and these were summarized by frequency distribution.

3.7.1.6.5 Digital Image Analysis

Facial photographs of patients in treatment groups 1, 2, 3, and 4 (once-daily dosing) were taken at predose, 6, and 12 hours postdose on days 1, 14, 28, and 35. An average of data from the 3 views of photographs (ie, right view, frontal view, and left view) were taken to represent the measurement at that timepoint. A separate exploratory analysis plan was provided by Canfield Scientific, Inc. for the exploratory analyses of DIA data (see Analysis Plan—Canfield Exploratory Analysis).

The following 6 measurements were performed using Canfield proprietary algorithms, with the analysis variables defined accordingly:
Fractional Area: defined as the percentage of the masked area occupied by redness. The masked area was defined as the area within which the analysis took place in pixels, which was then converted to millimeter square.
Erythema Severity: defined as the mean normalized fractional area and erythema contrast
Erythema Redness: defined as the percent of erythema redness within the mask redness in the RBX-Red image ([Mean Erythema Redness/Mean Mask Redness]*100°%)
Erythema Contrast: defined as (Mean Erythema Redness/Mean Background Redness in the RBX-Red image)
Intensity of Erythema: defined as percent intensity of erythema within the mask Intensity (Mean Intensity of Erythema/Mean Mask Intensity in a cross-polarized image)*100%)
Erythema Visibility: defined as (Mean Intensity of Erythema/Mean Background Intensity in a cross-polarized image)

3.7.1.6.6 Subgroup Analyses of Efficacy Variables

The primary efficacy variable was analyzed by age group (<45, 45 to 64, and ≥65 years old) and sex (male versus female) to compare each oxymetazoline group to its vehicle using the same statistical methods described in Section 3.5.1.1.

3.7.1.7 Safety Analysis

3.7.1.7.1 Treatment Exposure

Patient exposure to the study medication was characterized by study duration, treatment duration, and weight of study medication applied to patients. Study duration was defined as number of days from the date of first dosing to study exit; if the date of exit was missing, the date of the last visit was used (ie, date of study visit minus date of first dosing plus 1). Treatment duration was defined as number of days from the date of first dosing to last dose (ie, date of last dose minus date of first dose plus 1). Weight of study medication was calculated based on tube weight at postdose (after evening dose for twice-daily patients) minus tube weight at predose on each days 1, 2, 14, and 28. Study duration and treatment duration were summarized using descriptive statistics by treatment group, by total for each dosing regimen, and by overall total. Weight of study medication was summarized using study medication by treatment group and by total for each dosing regimen.

3.7.1.7.2 Adverse Events

Adverse events were coded using preferred terms and primary System Organ Class (SOC) from the Medical Dictionary for Regulatory Activities (MedDRA), version 15.1. Adverse events were collected both for the screening/baseline period (which were referred to as pretreatment adverse events [PTAEs]) and for the study period after treatment was initiated (which were referred to as postbaseline adverse events; ie, adverse events with start date from study day 1 through study exit). A treatment emergent adverse event (TEAE) was defined a postbaseline adverse event where there was no PTAE of the same MedDRA preferred term or the maximum severity during the postbaseline period was more severe than the maximal severity of any PTAE of the same MedDRA preferred term.

For each preferred term, the incidence of TEAEs was presented and summarized on a per-patient basis as follows:
  by preferred term in descending order of incidence rate
  by primary SOC in alphabetical order, and preferred term
  by primary SOC in alphabetical order, preferred term, and severity (maximum severity)

The maximum severity of a TEAE experienced by a patient was determined by the most severe rating recorded on the eCRF for the patient's given TEAE. The incidence of TEAEs was provided for all TEAEs regardless of causality and for treatment-related TEAEs.

Incidences of adverse events were summarized by treatment groups as well as by total of each regimen and by oxymetazoline versus vehicle.

TEAEs leading study discontinuation, and treatment-related TEAEs leading study discontinuation were summarized by preferred term within primary SOC.

A patient listing was generated for TEAEs, including patient age, sex, and race, sorted by primary SOC, preferred term, onset and stop date, onset day relative to the most recent dose, relationship, and severity.

Serious TEAEs, as well as pretreatment serious adverse events were summarized by preferred term within primary SOC. A listing of serious TEAEs and pretreatment serious adverse events was presented. In addition, treatment-related serious TEAEs were summarized by preferred term within primary SOC.

3.7.1.7.3 Facial Dermal Tolerability Assessment

Facial dermal tolerability assessment were evaluated by investigators and patients on days 1 (pre-dose, hours 1, 2, 4, 6, 8, 10, and 12), 2 (predose), 14 (predose, hours 1, 2, 4, 6, 8, 10, and 12), 28 (pre-dose, hours 1, 2, 4, 6, 8, 10, and 12), 35, and 56. Investigator's assessments included dryness and scaling and patient's assessment included stinging/burning, and pruritus; each had 4-point scales: 0=none, 1=mild, 2=moderate, 3=severe.

The number and percent of patients with at least a 1 severity increase (worsening) from baseline for 1 or more visits was generated by treatment group for day 1, day 14, day 28, and from day 1 through day 28. Raw values were summarized using shift tables and frequency distributions by treatment group. In addition, analyses of raw values and change from baseline at post-baseline timepoints and visits were performed using descriptive statistics. Baseline was the pre-dose assessment on day 1.

3.7.1.7.4 Clinical Laboratory Evaluations

Each applicable laboratory variable (hematology, blood serum chemistry, urinalysis), except those that had only a few categories of response, was summarized for each measurement day for the change from baseline. Laboratory values were categorized as low, normal, and high according to the reference normal range. For each variable, a shift table of low/normal/high values at baseline was compared to those at each scheduled visit for laboratory tests after baseline visit. A listing by patient of all abnormal (low or high as described above) laboratory values was provided.

responder rates for vehicle were assumed to be 10.0%, 4.0%, 4.0%, 4.0%, 4.0%, and 4.0% for hours 2, 4, 6, 8, 10, and 12, respectively, as the actual responder rate was 0.0% across all timepoints in Study 199201-001 a generalized linear model with a logit link function using GEE was performed 1000 times

TABLE 3-3

Power Calculations to Compare Oxymetazoline 1.5%, 1.0%, and 0.5% to Vehicle

| | Responder Rates from Study 199201-001 | | | | | | |
|---|---|---|---|---|---|---|---|
| | Hour 2 | Hour 4 | Hour 6 | Hour 8 | Hour 10 | Hour 12 | Power |
| Oxymetazoline 1.5% | 31.3% | 37.5% | 28.1% | 9.4% | 12.5% | 6.3% | 99.9% |
| Oxymetazoline 1.0% | 31.3% | 34.4% | 21.9% | 9.4% | 6.3% | 3.1% | 99.8% |
| Oxymetazoline 0.5% | 12.5% | 18.8% | 15.6% | 9.4% | 9.4% | 6.3% | 79.7% |
| Vehicle | 10.0% | 4.0% | 4.0% | 4.0% | 4.0% | 4.0% | |

3.7.1.7.5 Vital Signs

Data for systolic and diastolic blood pressure (mm Hg), pulse rate (beats/minute), respiratory rate (breaths/minute) and body temperature (° C.) were summarized by treatment groups. Change from baseline was summarized using descriptive statistics. Baseline values were defined as the last non-missing measurement prior to the first application of study medication on day 1.

3.7.1.7.6 Physical Examination

Physical examination values for each body system were categorized as normal or abnormal, and were summarized. A listing by patient of all abnormal physical examination values was provided.

3.7.1.7.7 Electrocardiogram

ECG variables included heart rate, QRS duration, QT interval, QTcB (QT corrected using the Bazett's correction), QTcF (QT corrected using the Fridericia's correction), RR interval, and PR interval. The raw values and change from baseline values for ECG variables were summarized by treatment group. All ECG assessment results from the central reading center (ERT) were presented in the data listings. Baseline was defined as the last non-missing measurement prior to the first dosing of study medication.

3.7.1.7.8 Pregnancy Test Results

Pregnancy test results for female patients of childbearing potential were provided in a data listing.

3.7.1.7.9 Subgroup Analyses for Safety Variables

There was no subgroup analysis for safety variables.

3.7.2 Determination of Sample Size

Sample size was determined empirically and power analyses were performed based on the day 1 results from Study 199201-001 using simulations. The assumptions for simulations were:

a sample size of 40 patients per treatment arm (taking 10% attrition rate of 45 enrolled patients)

2-sided alpha of 0.05 a responder was defined as a patient with at least a 2-grade improvement from baseline on both CEA and SSA scales analysis timepoints were hours 2, 4, 6, 8, 10, and 12 assumed responder rates:
    responder rates obtained after a single application of oxymetazoline 1.5%, 1.0%, and 0.5% on day 1 in Study 199201-001 as shown in Table 3-3

3.8 Changes in the Conduct of the Study or Planned Analyses

The study database was locked and the study unblinded on 12 Jul. 2013. No individual patients were unblinded during the study.

Note, there were 2 intended analyses that were described incorrectly in the statistical analysis plan, but were performed as intended:

The intended analysis of the proportion of patients with at least a 2-grade decrease (improvement) on both CEA and SSA-2 from baseline at hours 2, 4, 6, 8, 10, and 12 on days 1, 14, and 28 was described incorrectly in the statistical analysis plan as the proportion of patients with at least a 2-grade decrease (improvement) on both CEA and SSA from baseline.

The intended analysis of the proportion of patients with at least a 1-grade decrease (improvement) on both CEA and SSA from baseline at hours 2, 4, 6, 8, 10, and 12 on days 1, 14, and 28) was described incorrectly in the statistical analysis plan as the proportion of patients with at least a 2-grade decrease (improvement) on both SSA from baseline.

3.8.1 Changes in the Conduct of the Study

The protocol was approved on 29 Oct. 2012. There were no amendments to the protocol.

The study was conducted as planned.

3.8.2 Changes to Analyses Prior to Database Lock

Prior to database lock, there were no changes made to the analyses in the statistical analysis plan versus those in the approved protocol.

3.8.3 Changes to Analyses Following Database Lock

No changes were made to the statistical analysis plan following database lock. The following post hoc analyses were performed and summarized in the clinical study report:

proportion of patients with at least a 2-grade decrease (improvement) on both CEA and SSA from baseline during posttreatment period (days 29 to 56)

proportion of patients with rebound/worsening of erythema on both CEA and SSA during posttreatment period subgroup efficacy analyses by CEA and SSA score at baseline analysis of TEAEs that occurred during the treatment period and posttreatment period Additional post hoc exploratory analyses were made.

4. Results—Study Patients 4.1 Disposition of Patients

The first patient entered the study on 20 Dec. 2012 and the last patient exited the study on 3 Jun. 2013.

A total of 357 patients were enrolled and randomized into the study. One patient was randomized by error; this patient did not receive study treatment and was not included in the analysis populations. Therefore, 356 patients were included in the mITT and safety populations.

The treatment groups were evenly distributed, with 179 patients randomized to the twice-daily treatment group (135 Total Oxy and 44 vehicle), and 177 patients randomized to the once-daily treatment group (133 Total Oxy and 44 vehicle). Patient allocation to each treatment group and their subsequent disposition is summarized in Table 4-1.

A majority of patients (95.2% [339/356]) completed the study. In the twice-daily treatment group, 6.7% (9/135) of the Oxy patients and 4.5% (2/44) of the vehicle patients discontinued the study. In the once-daily treatment group, 3.0% (4/133) of the Oxy patients and 4.5% (2/44) of the vehicle patients discontinued the study. The primary reason for discontinuation from the study was adverse events in 2.8% (10/356) of all patients: 4.4% (6/135) in the Total Oxy twice-daily group versus 2.3% (1/44) in the vehicle BID group, and 1.5% (2/133) in the Total Oxy once-daily group versus 2.3% (1/44) in the vehicle once-daily group. These adverse events are further discussed in Section 6.3.3. Other reasons for study discontinuation are summarized in Table 4-1.

TABLE 4-1

Patient Disposition and Exit Status (mITT Population)

| Disposition | Oxy 1.5% BID | Oxy 1.0% BID | Oxy 0.5% BID | Total Oxy BID | Vehicle BID | Total BID | Oxy 1.5% QD |
|---|---|---|---|---|---|---|---|
| Enrolled | 45 | 45 | 45 | 135 | 44 | 179 | 44 |
| Completed | 42 (93.3) | 40 (88.9) | 44 (97.8) | 126 (93.3) | 42 (95.5) | 168 (93.9) | 44 (100.0) |
| Discontinued | 3 (6.7) | 5 (11.1) | 1 (2.2) | 9 (6.7) | 2 (4.5) | 11 (6.1) | 0 (0.0) |
| Adverse Event | 2 (4.4) | 3 (6.7) | 1 (2.2) | 6 (4.4) | 1 (2.3) | 7 (3.9) | 0 (0.0) |
| Lack of Efficacy | 0 (0.0) | 0 (0.0) | 0 (0.0) | 0 (0.0) | 0 (0.0) | 0 (0.0) | 0 (0.0) |
| Pregnancy | 0 (0.0) | 0 (0.0) | 0 (0.0) | 0 (0.0) | 0 (0.0) | 0 (0.0) | 0 (0.0) |
| Lost to Follow-up | 0 (0.0) | 0 (0.0) | 0 (0.0) | 0 (0.0) | 0 (0.0) | 0 (0.0) | 0 (0.0) |
| Personal Reasons | 0 (0.0) | 0 (0.0) | 0 (0.0) | 0 (0.0) | 0 (0.0) | 0 (0.0) | 0 (0.0) |
| Protocol Violation | 0 (0.0) | 0 (0.0) | 0 (0.0) | 0 (0.0) | 0 (0.0) | 0 (0.0) | 0 (0.0) |
| Other[a] | 1 (2.2) | 2 (4.4) | 0 (0.0) | 3 (2.2) | 1 (2.3) | 4 (2.2) | 0 (0.0) |

| Disposition | Oxy 1.0% QD | Oxy 0.5% QD | Total Oxy QD | Vehicle QD | Total QD | Overall Total |
|---|---|---|---|---|---|---|
| Enrolled | 44 | 45 | 133 | 44 | 177 | 356 |
| Completed | 43 (97.7) | 42 (93.3) | 129 (97.0) | 42 (95.5) | 171 (96.6) | 339 (95.2) |
| Discontinued | 1 (2.3) | 3 (6.7) | 4 (3.0) | 2 (4.5) | 6 (3.4) | 17 (4.8) |
| Adverse Event | 1 (2.3) | 1 (2.2) | 2 (1.5) | 1 (2.3) | 3 (1.7) | 10 (2.8) |
| Lack of Efficacy | 0 (0.0) | 0 (0.0) | 0 (0.0) | 0 (0.0) | 0 (0.0) | 0 (0.0) |
| Pregnancy | 0 (0.0) | 0 (0.0) | 0 (0.0) | 0 (0.0) | 0 (0.0) | 0 (0.0) |
| Lost to Follow-up | 0 (0.0) | 0 (0.0) | 0 (0.0) | 0 (0.0) | 0 (0.0) | 0 (0.0) |
| Personal Reasons | 0 (0.0) | 1 (2.2) | 1 (0.8) | 0 (0.0) | 1 (0.6) | 1 (0.3) |
| Protocol Violation | 0 (0.0) | 1 (2.2) | 1 (0.8) | 0 (0.0) | 1 (0.6) | 1 (0.3) |
| Other[a] | 0 (0.0) | 0 (0.0) | 0 (0.0) | 1 (2.3) | 1 (0.6) | 5 (1.4) |

BID = twice daily;
mITT = modified intent-to-treat;
Oxy = oxymetazoline hydrochloride;
QD = once daily 4.2 Protocol Deviations The master protocol deviation list contains all deviations from the study protocol for all study sites in all geographic regions. The master list was compiled prior to database lock based on data review and study monitoring activities. The complete list is included in the trial master file and is available upon request. Most deviations were minor and did not affect the study conduct or interpretation of the study results.

Using prespecified criteria developed during blinded data review and prior to data base lock, each deviation in the master list was classified as "non-significant" or "significant." Significant deviations were related to collection of study data, source documentation, treatment visit compliance, informed consent/privacy, study procedures, use of prohibited concomitant medication or procedure, administration of study drug, and SSA assessment or compliance. Non-significant deviations were related to items that were likely not to substantially affect the conduct and assessment of patient data in the study, eg, study visits or procedures not occurring on time.

A total of 55 patients had significant protocol deviations that were identified prior to database lock; these are listed below. There could have been more than one type of significant protocol deviation for a patient (ie, 7 patients had more than one type of significant protocol deviation).

incorrect version of informed consent form (ICF) signed by patient prior to study; ICF or patient privacy authorization not completed appropriately; study procedures were completed prior to patient signing the ICF (15 patients)

source documentation was missing, incomplete, incorrect, or not reviewed appropriately (14 patients)

pharmacokinetic laboratory sample was not collected (14 patients)

visit compliance (10 patients)

study procedure was not performed, not performed as specified, or performed by staff without appropriate delegation, authorization, or training (3 patients)

use of prohibited medication or procedure (2 patients)

patient missing at least 4 consecutive days of study drug (2 patients)

SSA assessment not "more redness than I prefer" or "completely unacceptable redness" by the patient (1 patient)

SSA and SSA-2 compliance (1 patient)

There were 18 patients excluded from analyses of the PP population. The primary reason for exclusion was due to patients missing at least 25% (7 days) of any study treatment days out of 28 days (14 patients). Other reasons included patients missing at least 4 consecutive days of study drug (2 patients), use of prohibited medication or procedure confounding study evaluation (1 patient), and SSA assessment not "more redness than I prefer" or "completely unacceptable redness" by the patient (1 patient).

One patient (10013-1189) in the Oxy 0.5% QD group discontinued the study due to a protocol violation of not complying with the visit schedule.

4.3 Datasets Analyzed

The mITT population, which consisted of all randomized patients who applied study medication during the study, and had both CEA and SSA measurements at baseline (ie, predose on day 1) and at least one postbaseline measurement for both CEA and SSA, included 356 patients (179 in the twice-daily treatment groups and 177 in the once-daily treatment groups) (Table 4-1).

The PP population, which consisted of randomized patients with no major protocol violation(s) during the study, included 338 patients (167 in the twice-daily treatment groups and 171 in the once-daily treatment groups).

The safety population, which consisted of patients who applied at least 1 dose of study medication in the study, was identical to the mITT population.

4.4 Demographics and Other Baseline Characteristics 4.4.1 Demographics

Demographics overview is presented in Table 4-2. The demographic variables were similar across all treatment groups. The mean age of the patients was 50.0 years (range 19 to 79 years). The largest proportion of patients (60.4%) was aged between 45 and 64 years of age, with 29.5% being <45 years of age, and 10.1% being ≥65 years of age.

There were more females than males (80.1% versus 19.9%), and the majority of the population was Caucasian (91.3%). The mean weight was 87.3 kg (range 46 to 162 kg), and the mean height was 166.4 cm (range 135 to 191 cm).

Per the inclusion criteria, all patients had CEA and SSA grades of 3 or higher at baseline, demonstrating moderate to severe facial erythema, with the exception of 1 patient. Patient 10001-1342 in the Oxy 0.5% BID group had an SSA grade of 2, which was considered to be a major protocol deviation (see Section 4.2). A total of 82.00% (292/356) of patients had CEA grade 3 and 18.0% (64/356) of patients had CEA grade 4 at baseline, while 70.8% (252/356) of patients had SSA grade 3 and 28.9% (103/356) of patients had SSA grade 4 at baseline.

The demographics of the PP population were similar to those of the mITT population, and the safety population was identical to the mITT population. The mITT population was used for the pharmacokinetic analysis.

TABLE 4-2

| | | Baseline Demographics (mITT Population) | | | | | | |
|---|---|---|---|---|---|---|---|---|
| Characteristic | Attribute | Oxy 1.5% BID (N = 45) | Oxy 1.0% BID (N = 45) | Oxy 0.5% BID (N = 45) | Vehicle BID (N = 44) | Oxy 1.5% QD (N = 44) | Oxy 1.0% QD (N = 44) | Oxy 0.5% QD (N = 45) |
| Age (yrs) | N | 45 | 45 | 45 | 44 | 44 | 44 | 45 |
| | Mean | 45.9 | 51.0 | 48.1 | 53.0 | 51.2 | 51.3 | 49.6 |
| | SD | 12.80 | 10.77 | 10.64 | 13.34 | 11.05 | 12.09 | 10.36 |
| | Median | 48.0 | 50.0 | 48.0 | 54.0 | 50.5 | 50.5 | 53.0 |
| | Min | 19 | 23 | 23 | 21 | 23 | 27 | 21 |
| | Max | 69 | 71 | 69 | 79 | 76 | 74 | 65 |
| (n [%]) | <45 | 16 (35.6) | 11 (24.4) | 16 (35.6) | 9 (20.5) | 10 (22.7) | 15 (34.1) | 14 (31.1) |
| | 45 to 64 | 27 (60.0) | 29 (64.4) | 26 (57.8) | 28 (63.6) | 28 (63.6) | 23 (52.3) | 30 (66.7) |
| | ≥65 | 2 (4.4) | 5 (11.1) | 3 (6.7) | 7 (15.9) | 6 (13.6) | 6 (13.6) | 1 (2.2) |
| Sex | N | 45 | 45 | 45 | 44 | 44 | 44 | 45 |
| (n [%]) | Male | 9 (20.0) | 11 (24.4) | 4 (8.9) | 11 (25.0) | 11 (25.0) | 9 (20.5) | 10 (22.2) |
| | Female | 36 (80.0) | 34 (75.6) | 41 (91.1) | 33 (75.0) | 33 (75.0) | 35 (79.5) | 35 (77.8) |
| Race | N | 45 | 45 | 45 | 44 | 44 | 44 | 45 |
| (n [%]) | Caucasian | 39 (86.7) | 42 (93.3) | 42 (93.3) | 40 (90.9) | 38 (86.4) | 40 (90.9) | 43 (95.6) |
| | Black | 0 (0.0) | 0 (0.0) | 0 (0.0) | 0 (0.0) | 1 (2.3) | 0 (0.0) | 0 (0.0) |
| | Hispanic | 6 (13.3) | 3 (6.7) | 3 (6.7) | 4 (9.1) | 5 (11.4) | 4 (9.1) | 2 (4.4) |
| | Other | 0 (0.0) | 0 (0.0) | 0 (0.0) | 0 (0.0) | 0 (0.0) | 0 (0.0) | 0 (0.0) |
| | Caucasian | 39 (86.7) | 42 (93.3) | 42 (93.3) | 40 (90.9) | 38 (86.4) | 40 (90.9) | 43 (95.6) |
| | Non-Caucasian | 6 (13.3) | 3 (6.7) | 3 (6.7) | 4 (9.1) | 6 (13.6) | 4 (9.1) | 2 (4.4) |

TABLE 4-2-continued

Baseline Demographics (mITT Population)

| | | | | | | | | |
|---|---|---|---|---|---|---|---|---|
| CEA[a] (n [%]) | N | 45 | 45 | 45 | 44 | 44 | 44 | 45 |
| | Grade 0 | 0 (0.0) | 0 (0.0) | 0 (0.0) | 0 (0.0) | 0 (0.0) | 0 (0.0) | 0 (0.0) |
| | Grade 1 | 0 (0.0) | 0 (0.0) | 0 (0.0) | 0 (0.0) | 0 (0.0) | 0 (0.0) | 0 (0.0) |
| | Grade 2 | 0 (0.0) | 0 (0.0) | 0 (0.0) | 0 (0.0) | 0 (0.0) | 0 (0.0) | 0 (0.0) |
| | Grade 3 | 33 (73.3) | 37 (82.2) | 38 (84.4) | 40 (90.9) | 38 (86.4) | 34 (77.3) | 37 (82.2) |
| | Grade 4 | 12 (26.7) | 8 (17.8) | 7 (15.6) | 4 (9.1) | 6 (13.6) | 10 (22.7) | 8 (17.8) |
| SSA[a] (n [%]) | N | 45 | 45 | 45 | 44 | 44 | 44 | 45 |
| | Grade 0 | 0 (0.0) | 0 (0.0) | 0 (0.0) | 0 (0.0) | 0 (0.0) | 0 (0.0) | 0 (0.0) |
| | Grade 1 | 0 (0.0) | 0 (0.0) | 0 (0.0) | 0 (0.0) | 0 (0.0) | 0 (0.0) | 0 (0.0) |
| | Grade 2 | 0 (0.0) | 0 (0.0) | 1 (2.2)[b] | 0 (0.0) | 0 (0.0) | 0 (0.0) | 0 (0.0) |
| | Grade 3 | 34 (75.6) | 32 (71.1) | 31 (68.9) | 28 (63.6) | 30 (68.2) | 36 (81.8) | 28 (62.2) |
| | Grade 4 | 11 (24.4) | 13 (28.9) | 13 (28.9) | 16 (36.4) | 14 (31.8) | 8 (18.2) | 17 (37.8) |
| Weight (kg) | N | 44 | 45 | 45 | 44 | 44 | 44 | 45 |
| | Mean | 87.7 | 90.5 | 82.6 | 84.3 | 91.6 | 88.6 | 86.3 |
| | SD | 17.39 | 19.20 | 22.12 | 18.83 | 19.64 | 24.79 | 16.82 |
| | Median | 85.0 | 88.0 | 77.0 | 83.0 | 89.0 | 84.0 | 84.0 |
| | Min | 57 | 50 | 52 | 52 | 53 | 46 | 52 |
| | Max | 136 | 135 | 151 | 123 | 135 | 162 | 120 |
| Height (cm) | N | 44 | 45 | 45 | 44 | 44 | 44 | 45 |
| | Mean | 165.1 | 167.8 | 165.5 | 167.1 | 168.5 | 165.8 | 166.9 |
| | SD | 8.38 | 11.20 | 8.10 | 9.79 | 8.42 | 10.30 | 9.78 |
| | Median | 165.0 | 166.0 | 164.0 | 165.0 | 167.5 | 168.0 | 165.0 |
| | Min | 140 | 135 | 152 | 147 | 152 | 142 | 140 |
| | Max | 183 | 191 | 185 | 191 | 191 | 191 | 189 |

| Characteristic | Attribute | Vehicle QD (N = 44) | Total Oxy BID (N = 135) | Total Oxy QD (N = 133) | Total Oxy (N = 268) | Total Vehicle (N = 88) | Overall Total (N = 356) |
|---|---|---|---|---|---|---|---|
| Age (yrs) | N | 44 | 135 | 133 | 268 | 88 | 356 |
| | Mean | 50.2 | 48.3 | 50.7 | 49.5 | 51.6 | 50.0 |
| | SD | 11.26 | 11.55 | 11.13 | 11.38 | 12.36 | 11.65 |
| | Median | 48.5 | 49.0 | 51.0 | 50.0 | 50.0 | 50.0 |
| | Min | 22 | 19 | 21 | 19 | 21 | 19 |
| | Max | 75 | 71 | 76 | 76 | 79 | 79 |
| (n [%]) | <45 | 14 (31.8) | 43 (31.9) | 39 (29.3) | 82 (30.6) | 23 (26.1) | 105 (29.5) |
| | 45 to 64 | 24 (54.5) | 82 (60.7) | 81 (60.9) | 163 (60.8) | 52 (59.1) | 215 (60.4) |
| | ≥65 | 6 (13.6) | 10 (7.4) | 13 (9.8) | 23 (8.6) | 13 (14.8) | 36 (10.1) |
| Sex (n [%]) | N | 44 | 135 | 133 | 268 | 88 | 356 |
| | Male | 6 (13.6) | 24 (17.8) | 30 (22.6) | 54 (20.1) | 17 (19.3) | 71 (19.9) |
| | Female | 38 (86.4) | 111 (82.2) | 103 (77.4) | 214 (79.9) | 71 (80.7) | 285 (80.1) |
| Race (n [%]) | N | 44 | 135 | 133 | 268 | 88 | 356 |
| | Caucasian | 41 (93.2) | 123 (91.1) | 121 (91.0) | 244 (91.0) | 81 (92.0) | 325 (91.3) |
| | Black | 0 (0.0) | 0 (0.0) | 1 (0.8) | 1 (0.4) | 0 (0.0) | 1 (0.3) |
| | Hispanic | 3 (6.8) | 12 (8.9) | 11 (8.3) | 23 (8.6) | 7 (8.0) | 30 (8.4) |
| | Other | 0 (0.0) | 0 (0.0) | 0 (0.0) | 0 (0.0) | 0 (0.0) | 0 (0.0) |
| | Caucasian | 41 (93.2) | 123 (91.1) | 121 (91.0) | 244 (91.0) | 81 (92.0) | 325 (91.3) |
| | Non-Caucasian | 3 (6.8) | 12 (8.9) | 12 (9.0) | 24 (9.0) | 7 (8.0) | 31 (8.7) |
| CEA[a] (n [%]) | N | 44 | 135 | 133 | 268 | 88 | 356 |
| | Grade 0 | 0 (0.0) | 0 (0.0) | 0 (0.0) | 0 (0.0) | 0 (0.0) | 0 (0.0) |
| | Grade 1 | 0 (0.0) | 0 (0.0) | 0 (0.0) | 0 (0.0) | 0 (0.0) | 0 (0.0) |
| | Grade 2 | 0 (0.0) | 0 (0.0) | 0 (0.0) | 0 (0.0) | 0 (0.0) | 0 (0.0) |
| | Grade 3 | 35 (79.5) | 108 (80.0) | 109 (82.0) | 217 (81.0) | 75 (85.2) | 292 (82.0) |
| | Grade 4 | 9 (20.5) | 27 (20.0) | 24 (18.0) | 51 (19.0) | 13 (14.8) | 64 (18.0) |
| SSA[a] (n [%]) | N | 44 | 135 | 133 | 268 | 88 | 356 |
| | Grade 0 | 0 (0.0) | 0 (0.0) | 0 (0.0) | 0 (0.0) | 0 (0.0) | 0 (0.0) |
| | Grade 1 | 0 (0.0) | 0 (0.0) | 0 (0.0) | 0 (0.0) | 0 (0.0) | 0 (0.0) |
| | Grade 2 | 0 (0.0) | 1 (0.7) | 0 (0.0) | 1 (0.4) | 0 (0.0) | 1 (0.3) |
| | Grade 3 | 33 (75.0) | 97 (71.9) | 94 (70.7) | 191 (71.3) | 61 (69.3) | 252 (70.8) |
| | Grade 4 | 11 (25.0) | 37 (27.4) | 39 (29.3) | 76 (28.4) | 27 (30.7) | 103 (28.9) |
| Weight (kg) | N | 44 | 134 | 133 | 267 | 88 | 355 |
| | Mean | 86.8 | 87.0 | 88.8 | 87.9 | 85.5 | 87.3 |
| | SD | 17.90 | 19.81 | 20.61 | 20.20 | 18.31 | 19.75 |
| | Median | 87.5 | 84.0 | 87.0 | 85.0 | 86.0 | 86.0 |
| | Min | 48 | 50 | 46 | 46 | 48 | 46 |
| | Max | 131 | 151 | 162 | 162 | 131 | 162 |
| Height (cm) | N | 44 | 134 | 133 | 267 | 88 | 355 |
| | Mean | 164.8 | 166.2 | 167.0 | 166.6 | 166.0 | 166.4 |
| | SD | 7.64 | 9.35 | 9.53 | 9.43 | 8.81 | 9.27 |
| | Median | 164.0 | 165.0 | 166.0 | 165.0 | 165.0 | 165.0 |

TABLE 4-2-continued

| | Baseline Demographics (mITT Population) | | | | | |
|---|---|---|---|---|---|---|
| Min | 152 | 135 | 140 | 135 | 147 | 135 |
| Max | 185 | 191 | 191 | 191 | 191 | 191 |

BID = twice daily;
CEA = Clinician's Erythema Assessment scale;
Oxy = oxymetazoline hydrochloride;
QD = once daily;
SSA = Subject Self-Assessment of Erythema
[a]CEA and SSA were measured predose on day 1.
[b]Patient 10001-1342 had an SSA grade of 2, which was considered to be a major protocol deviation (see Section 4.2).

4.4.2 Medical History

The most common patient medical histories (occurring in >20% of all patients), other than those coding to the MedDRA SOC of Skin and Subcutaneous Tissue Disorders, mapped to the MedDRA SOCs of Immune System Disorders (33.1% [118/356]), Vascular Disorders (27.5% [98/356]), Metabolism and Nutrition Disorders (25.0% [89/356]), Social Circumstances (24.2% [86/356]), and Musculoskeletal and Connective Tissue Disorders (22.2% [79/356]). There were no clinically meaningful differences among the treatment groups for any medical history term.

4.4.3 Prior and Concomitant Medications

A total of 80.3% (286/356) of all patients used medications prior to study entry. The most frequently used prior medications (in >10% of all patients) were used for surgical and medical procedures (44.1% [157/356]); of these, the most commonly used was plain multivitamins (11.2% [40/356]). The only other medications that were taken by >10% of all patients were intravaginal contraceptives (11.0% [39/356]); all other prior medications were used in <10% of patients overall.

Details of medications that were prohibited for the duration of the study are provided in Section 3.4.7.

The most commonly used concomitant medications (in >10% of all patients) during the study were intravaginal contraceptives (11.0% [39/356]) and plain multivitamins (10.7% [38/356]). All other concomitant medications were used in <10% of patients overall.

4.5 Treatment Compliance

As described in Section 3.4.8, the investigator was instructed to keep an accurate accounting of the number of investigational units received from Allergan, dispensed to the patients, the number of units returned to the investigator by the patient, and the number of units returned to Allergan during and at the completion of the study.

Additionally, the study medication tubes were weighed predose and postdose at each in-clinic treatment visit. Per the study protocol, the patient was instructed to apply approximately a pea size amount of oxymetazoline cream 0.5%, 1.0%, 1.5%, or vehicle to the face once or twice a day, based on the randomization assignment, for 28 consecutive days. A pea size amount of the study medication represented approximately 0.5 grams of the product. At each visit, the weights of study medication were consistent across the twice-daily and once-daily treatment groups, with an overall weight of approximately 0.3 grams per application.

5. Efficacy, Health Outcomes, Pharmacokinetics, and Other Measures Evaluation 5.1 Analysis of Efficacy 5.1.1 Primary Efficacy Analysis: Composite of Clinicians Erythema Assessment and Subject Self Assessment of Erythema Scale Treatment Period On day 1, the proportions of patients with at least a 2-grade decrease (improvement) from baseline over a 12-hour period for both the CEA and SSA were significantly greater than vehicle in the Oxy 1.5%, 1.0%, and 0.5% BID treatment groups and the Oxy 1.5% and 1.0% QD treatment groups (Table 5-1). Statistically significant differences compared with vehicle were seen starting at hour 2 on day 1 for the Oxy 1.5% BID, Oxy 1.0% BID, and Oxy 1.5% QD treatment groups, and at hour 4 on day 1 for the Oxy 1.0% QD treatment group.

Treatment response was maintained through day 14 (Table 5-1). The proportions of patients with at least a 2-grade improvement from baseline at hour 12 on day 14 for both the CEA and SSA scales following twice-daily dosing were 13.3%, 17.8% and 8.9% with Oxy 1.5%, 1.0%, and 0.5%, respectively, compared to 4.5% with vehicle. There was a statistically significant difference between Oxy 1.0% BID and vehicle over the 12-hour period (p=0.015). Following once-daily dosing, the proportions of patients with at least a 2-grade improvement from baseline at hour 12 on day 14 were 6.8%, 4.5% and 6.7% with Oxy 1.5%, 1.0%, and 0.5%, respectively, compared to 6.8% with vehicle. There were no statistically significant between-group differences in any Oxy treatments compared to vehicle treatments over the 12-hour period.

On day 28 following twice-daily dosing in the mITT population, the Oxy 1.5% and 1.0% treatment groups showed a statistically significant reduction in facial erythema, as defined by the proportion of responders, i.e., patients with at least a 2-grade decrease (improvement) from baseline over a 12-hour period on both the CEA and SSA scales compared with vehicle (Table 5-1; Table 5-2). There was no statistically significant difference between Oxy 0.5% and vehicle.

Statistically significant differences compared with the vehicle group were observed starting at hour 4 in the Oxy 1.5% BID group and at hour 8 in the Oxy 1.0% BID group. Significant between-group differences were not observed at individual timepoints for Oxy 0.5% versus vehicle given twice-daily. The proportions of responders in the twice-daily treatment groups at hour 4 (peak timepoint) on day 28 were 22.2%, 20.0% and 11.1% with Oxy 1.5%, 1.0%, and 0.5%, respectively, compared to 6.8% with vehicle. The proportions of responders in the twice-daily treatment groups were maintained at hour 12 on day 28, with 15.6%, 11.1% and 13.3% in the Oxy 1.5%, 1.0%, and 0.5% groups, respectively, compared to 4.5% in the vehicle group.

Following once-daily dosing in the mITT population, all 3 Oxy treatment groups of 1.5%, 1.0%, and 0.5% demonstrated a statistically significant reduction in facial erythema over a 12-hour period on day 28 compared with vehicle (Table 5-1; Table 5-2).

Statistically significant differences compared with the vehicle group were observed starting at hour 2 in the Oxy 1.5% QD group and at hour 4 in the Oxy 1.0% QD group. Significant between-group differences were not observed at individual timepoints for Oxy 0.5% QD versus vehicle QD. The proportions of responders in the once-daily treatment groups at hour 4 (peak timepoint) on day 28 were 27.3%, 31.8% and 17.8% with Oxy 1.5%, 1.0%, and 0.5%, respectively, compared to 4.5% with vehicle. The proportions of responders in the once-daily treatment groups were maintained at hour 12 on day 28, with 13.6%, 13.6%, and 13.3% in the Oxy 1.5%, 1.0%, and 0.5% groups, respectively, compared to 2.3% in the vehicle group.

Similar results were observed in the PP population, whereby the Oxy 1.5% and 1.0% BID treatment groups and the Oxy 1.5%, 1.0%, and 0.5% QD treatment groups demonstrated a statistically significant reduction in facial erythema compared to the vehicle group over a 12-hour period on day 28.

The pair-wise comparison showed no statistically significant differences in response rates over a 12-hour time period on day 28 between any of the Oxy twice-daily or once-daily treatment groups. However, a numerically higher response rate was observed for the Oxy 1.0% QD group versus the Oxy 0.5% QD group at hours 2, 4, 6, 8, and 10. The treatment response rate on day 28 was similar between the Oxy 1.5% QD and Oxy 1.0% QD treatment groups. When comparing each dose following twice-daily or once-daily dosing (ie, Oxy 1.5% BID versus Oxy 1.5% QD, Oxy 1.0% BID versus Oxy 1.0% QD, and Oxy 0.5% BID versus Oxy 0.5% QD), response rates were similar in each treatment group at each timepoint.

TABLE 5-1

Primary Efficacy Variable: Treatment Responder Rate of at Least 2-grade Improvement on CEA and SSA from Baseline by Treatment Group, Visit and Timepoint (mITT Population)

Twice-daily Dosing

| Timepoint (Hour)[a] | Oxy 1.5% BID | | | Oxy 1.0% BID | | | Oxy 0.5% BID | | | Vehicle BID | | |
|---|---|---|---|---|---|---|---|---|---|---|---|---|
| | Day 1 % (x/n) | Day 14 % (x/n) | Day 28 % (x/n) | Day 1 % (x/n) | Day 14 % (x/n) | Day 28 % (x/n) | Day 1 % (x/n) | Day 14 % (x/n) | Day 28 % (x/n) | Day 1 % (x/n) | Day 14 % (x/n) | Day 28 % (x/n) |
| 0.5 | 2.2 (1/45) | 6.7 (3/45) | 6.7 (3/45) | 2.2 (1/45) | 2.2 (1/45) | 6.7 (3/45) | 0.0 (0/45) | 0.0 (0/45) | 6.7 (3/45) | 0.0 (0/44) | 9.1 (4/44) | 2.3 (1/44) |
| 1 | 2.2 (1/45) | 11.1 (5/45) | 8.9 (4/45) | 8.9 (4/45) | 6.7 (3/45) | 11.1 (5/45) | 0.0 (0/45) | 0.0 (0/45) | 6.7 (3/45) | 4.5 (2/44) | 4.5 (2/44) | 2.3 (1/44) |
| 2 | 17.8 (8/45) | 13.3 (6/45) | 15.6 (7/45) | 20.0 (9/45) | 11.1 (5/45) | 17.8 (8/45) | 0.0 (0/45) | 4.4 (2/45) | 8.9 (4/45) | 2.3 (1/44) | 2.3 (1/44) | 6.8 (3/44) |
| 4 | 17.8 (8/45) | 13.3 (6/45) | 22.2 (10/45) | 17.8 (8/45) | 22.2 (10/45) | 20.0 (9/45) | 11.1 (5/45) | 6.7 (3/45) | 11.1 (5/45) | 0.0 (0/44) | 2.3 (1/44) | 6.8 (3/44) |
| 6 | 17.8 (8/45) | 2.2 (1/45) | 24.4 (11/45) | 17.8 (8/45) | 17.8 (8/45) | 13.3 (6/45) | 4.4 (2/45) | 6.7 (3/45) | 11.1 (5/45) | 4.5 (2/44) | 6.8 (3/44) | 4.5 (2/44) |
| 8 | 15.6 (7/45) | 11.1 (5/45) | 20.0 (9/45) | 20.0 (9/45) | 20.0 (9/45) | 20.0 (9/45) | 6.7 (3/45) | 11.1 (5/45) | 8.9 (4/45) | 0.0 (0/44) | 6.8 (3/44) | 2.3 (1/44) |
| 10 | 24.4 (11/45) | 15.6 (7/45) | 26.7 (12/45) | 13.3 (6/45) | 17.8 (8/45) | 15.6 (7/45) | 11.1 (5/45) | 13.3 (6/45) | 13.3 (6/45) | 0.0 (0/44) | 4.5 (2/44) | 2.3 (1/44) |
| 12 | 8.9 (4/45) | 13.3 (6/45) | 15.6 (7/45) | 13.3 (6/45) | 17.8 (8/45) | 11.1 (5/45) | 4.4 (2/45) | 8.9 (4/45) | 13.3 (6/45) | 0.0 (0/44) | 4.5 (2/44) | 4.5 (2/44) |
| P-value[b] | <0.001 | 0.121 | 0.006 | <0.001 | 0.015 | 0.021 | 0.020 | 0.290 | 0.143 | | | |

Once-daily Dosing

| Timepoint (Hour)[a] | Oxy 1.5% QD | | | Oxy 1.0% QD | | | Oxy 0.5% QD | | | Vehicle QD | | |
|---|---|---|---|---|---|---|---|---|---|---|---|---|
| | Day 1 % (x/n) | Day 14 % (x/n) | Day 28 % (x/n) | Day 1 % (x/n) | Day 14 % (x/n) | Day 28 % (x/n) | Day 1 % (x/n) | Day 14 % (x/n) | Day 28 % (x/n) | Day 1 % (x/n) | Day 14 % (x/n) | Day 28 % (x/n) |
| 0.5 | 0.0 (0/44) | 4.5 (2/44) | 6.8 (3/44) | 0.0 (0/44) | 2.3 (1/44) | 11.4 (5/44) | 0.0 (0/45) | 2.2 (1/45) | 6.7 (3/45) | 0.0 (0/44) | 2.3 (1/44) | 4.5 (2/44) |
| 1 | 6.8 (3/44) | 13.6 (6/44) | 18.2 (8/44) | 4.5 (2/44) | 6.8 (3/44) | 13.6 (6/44) | 4.4 (2/45) | 4.4 (2/45) | 11.1 (5/45) | 0.0 (0/44) | 4.5 (2/44) | 2.3 (1/44) |
| 2 | 22.7 (10/44) | 18.2 (8/44) | 22.7 (10/44) | 11.4 (5/44) | 13.6 (6/44) | 20.5 (9/44) | 11.1 (5/45) | 11.1 (5/45) | 13.3 (6/45) | 0.0 (0/44) | 6.8 (3/44) | 6.8 (3/44) |
| 4 | 34.1 (15/44) | 15.9 (7/44) | 27.3 (12/44) | 20.5 (9/44) | 15.9 (7/44) | 31.8 (14/44) | 11.1 (5/45) | 13.3 (6/45) | 17.8 (8/45) | 4.5 (2/44) | 6.8 (3/44) | 4.5 (2/44) |
| 6 | 22.7 (10/44) | 18.2 (8/44) | 13.6 (6/44) | 18.2 (8/44) | 15.9 (7/44) | 22.7 (10/44) | 8.9 (4/45) | 8.9 (4/45) | 17.8 (8/45) | 4.5 (2/44) | 4.5 (2/44) | 4.5 (2/44) |
| 8 | 22.7 (10/44) | 13.6 (6/44) | 20.5 (9/44) | 18.2 (8/44) | 13.6 (6/44) | 20.5 (9/44) | 6.7 (3/45) | 8.9 (4/45) | 15.6 (7/45) | 2.3 (1/44) | 4.5 (2/44) | 4.5 (2/44) |
| 10 | 15.9 (7/44) | 6.8 (3/44) | 13.6 (6/44) | 11.4 (5/44) | 6.8 (3/44) | 20.5 (9/44) | 6.7 (3/45) | 4.4 (2/45) | 17.8 (8/45) | 6.8 (3/44) | 2.3 (1/44) | 4.5 (2/44) |

TABLE 5-1-continued

Primary Efficacy Variable: Treatment Responder Rate of at Least 2-grade Improvement on CEA and SSA from Baseline by Treatment Group, Visit and Timepoint (mITT Population)

| 12 | 4.5 | 6.8 | 13.6 | 2.3 | 4.5 | 13.6 | 11.1 | 6.7 | 13.3 | 2.3 | 6.8 | 2.3 |
|---|---|---|---|---|---|---|---|---|---|---|---|---|
|  | (2/44) | (3/44) | (6/44) | (1/44) | (2/44) | (6/44) | (5/45) | (3/45) | (6/45) | (1/44) | (3/44) | (1/44) |
| P-value[b] | <0.001 | 0.111 | 0.012 | 0.022 | 0.133 | 0.006 | 0.086 | 0.423 | 0.049 |  |  |  |

BID = twice-daily;
CEA = Clinician's Erythema Assessment scale;
mITT = modified intent-to-treat;
Oxy = oxymetazoline hydrochloride;
QD = once daily,
SSA = Subject Self-Assessment of Erythema Note:
Bold values indicate statistical significance versus vehicle for that timepoint with Pearson's chi-square test.

[a]The timepoint was based on eCRF vsit and time.

[b]P-value for between-treatment comparisons over a 12-hour period (including hours 2, 4, 6, 8, 10, and 12) were based on a generalized linear model with a logit link function and exchangeable covariance structure using generalized estimation equations. The model included fixed effects of treatment group and timepoints. The comparisons were made for active versus vehicle on the same visit day.

TABLE 5-2

Primary Efficacy Endpoint: Treatment Responder Rate of at Least 2-grade Improvement on CEA and SSA from Baseline Over 12 Hours on Day 28 (mITT Population)

| | | Twice-daily Dosing | | | |
|---|---|---|---|---|---|
| Timepoint (Hour)[a] | Description | Oxy 1.5% BID (N = 45) | Oxy 1.0% BID (N = 45) | Oxy 0.5% BID (N = 45) | Vehicle BID (N = 44) |
| 2 | Responder (n [%]) | 7 (15.6) | 8 (17.8) | 4 (8.9) | 3 (6.8) |
|  | Difference[b] | 8.7 | 11.0 | 2.1 | |
|  | Difference, 90% CI | −2.10, 19.57 | −0.27, 22.19 | −7.27, 11.41 | |
|  | P-value[c] | 0.315 | 0.116 | >0.999 | |
| 4 | Responder (n [%]) | 10 (22.2) | 9 (20.0) | 5 (11.1) | 3 (6.8) |
|  | Difference[b] | 15.4 | 13.2 | 4.3 | |
|  | Difference, 90% CI | 3.48, 27.33 | 1.59, 24.78 | −5.60, 14.19 | |
|  | P-value[c] | 0.040 | 0.069 | 0.714 | |
| 6 | Responder (n [%]) | 11 (24.4) | 6 (13.3) | 5 (11.1) | 2 (4.5) |
|  | Difference[b] | 19.9 | 8.8 | 6.6 | |
|  | Difference, 90% CI | 8.20, 31.60 | −0.99, 18.56 | −2.68, 15.82 | |
|  | P-value[c] | 0.008 | 0.266 | 0.434 | |
| 8 | Responder (n [%]) | 9 (20.0) | 9 (20.0) | 4 (8.9) | 1 (2.3) |
|  | Difference[b] | 17.7 | 17.7 | 6.6 | |
|  | Difference, 90% CI | 7.28, 28.18 | 7.28, 28.18 | −1.26, 14.49 | |
|  | P-value[c] | 0.015 | 0.015 | 0.361 | |
| 10 | Responder (n [%]) | 12 (26.7) | 7 (15.6) | 6 (13.3) | 1 (2.3) |
|  | Difference[b] | 24.4 | 13.3 | 11.1 | |
|  | Difference, 90% CI | 12.97, 35.82 | 3.69, 22.88 | 1.97, 20.15 | |
|  | P-value[c] | 0.001 | 0.058 | 0.110 | |
| 12 | Responder (n [%]) | 7 (15.6) | 5 (11.1) | 6 (13.3) | 2 (4.5) |
|  | Difference[b] | 11.0 | 6.6 | 8.8 | |
|  | Difference, 90% CI | 0.76, 21.26 | −2.68, 15.82 | −0.99, 18.56 | |
|  | P-value[c] | 0.157 | 0.434 | 0.266 | |
| P-value[d] | | 0.006 | 0.021 | 0.143 | |

BID = twice daily;
CEA = Clinician's Erythema Assessment;
CI = confidence interval;
mITT = modified intent-to-treat;
Oxy = oxymetazoline hydrochloride;
SSA = Subject Self-Assessment of Erythema Note:
A responder was defined at least a 2-grade improvement from baseline on both CEA and SSA. The baseline value was the value collected on day 1 predose (baseline). If day 1 predose data were missing, screening visit data were used. The last observation carried forward method was used for missing data at postbaseline visits.

[a]The timepoint was based on eCRF visit and time.

[b]The treatment difference was calculated for active treatment group minus its vehicle of the same dose regimen.

[c]P-values for between-treatment comparisons at a single timepoint were based on a Pearson's chi-square test or Fisher's exact test.

[d]P-values for between-treatment comparisons over a 12-hour period (ie, hours 2, 4, 6, 8, 10, and 12) were based on a generalized linear model with a logit link function and exchangeable convariance structure using generalized estimation equations. The model included fixed effects of treatment group and timepoints.

TABLE 5-2-continued

Primary Efficacy Endpoint: Treatment Responder Rate of at Least 2-grade Improvement on CEA and SSA from Baseline Over 12 Hours on Day 28 (mITT Population)

| | | Once-daily Dosing | | | |
|---|---|---|---|---|---|
| Timepoint (Hour)[a] | Description | Oxy 1.5% QD (N = 44) | Oxy 1.0% QD (N = 44) | Oxy 0.5% QD (N = 45) | Vehicle QD (N = 44) |
| 2 | Responder (n [%]) | 10 (22.7) | 9 (20.5) | 6 (13.3) | 3 (6.8) |
| | Difference[b] | 15.9 | 13.6 | 6.5 | |
| | Difference, 90% CI | 3.82, 28.00 | 1.88, 25.40 | −3.87, 16.90 | |
| | P-value[c] | 0.035 | 0.062 | 0.485 | |
| 4 | Responder (n [%]) | 12 (27.3) | 14 (31.8) | 8 (17.8) | 2 (4.5) |
| | Difference[b] | 22.7 | 27.3 | 13.2 | |
| | Difference, 90% CI | 10.57, 34.88 | 14.66, 39.89 | 2.56, 23.90 | |
| | P-value[c] | 0.004 | <0.001 | 0.090 | |
| 6 | Responder (n [%]) | 6 (13.6) | 10 (22.7) | 8 (17.8) | 2 (4.5) |
| | Difference[b] | 9.1 | 18.2 | 13.2 | |
| | Difference, 90% CI | −0.83, 19.02 | 6.61, 29.75 | 2.56, 23.90 | |
| | P-value[c] | 0.266 | 0.013 | 0.090 | |
| 8 | Responder (n [%]) | 9 (20.5) | 9 (20.5) | 7 (15.6) | 2 (4.5) |
| | Difference[b] | 15.9 | 15.9 | 11.0 | |
| | Difference, 90% CI | 4.68, 27.13 | 4.68, 27.13 | 0.76, 21.26 | |
| | P-value[c] | 0.024 | 0.024 | 0.157 | |
| 10 | Responder (n [%]) | 6 (13.6) | 9 (20.5) | 8 (17.8) | 2 (4.5) |
| | Difference[b] | 9.1 | 15.9 | 13.2 | |
| | Difference, 90% CI | −0.83, 19.02 | 4.68, 27.13 | 2.56, 23.90 | |
| | P-value[c] | 0.266 | 0.024 | 0.090 | |
| 12 | Responder (n [%]) | 6 (13.6) | 6 (13.6) | 6 (13.3) | 1 (2.3) |
| | Difference[b] | 11.4 | 11.4 | 11.1 | |
| | Difference, 90% CI | 2.11, 20.61 | 2.11, 20.61 | 1.97, 20.15 | |
| | P-value[c] | 0.110 | 0.110 | 0.110 | |
| P-value[d] | | 0.012 | 0.006 | 0.049 | |

CEA = Clinician's Erythema Assessment;
CI = confidence interval;
mITT = modified intent-to-treat;
Oxy = oxymetazoline hydrochloride;
QD = once daily;
SSA = Subject Self-Assessment of Erythema
Note:
A responder was defined at least a 2-grade improvement from baseline on both CEA and SSA. The baseline value was the value collected on day 1 predose (baseline). If day 1 predose data were missing, screening visit data were used. The last observation carried forward method was used for missing data at postbaseline visits.
[a]The timepoint was based on eCRF visit and time.
[b]The treatment difference was calculated for active treatment group minus its vehicle of the same dose regimen.
[c]P-values for between-treatment comparisons at a single timepoint were based on a Pearson's chi-square test or Fisher's exact test.
[d]P-values for between-treatment comparisons over a 12-hour period (ie, hours 2, 4, 6, 8, 10, and 12) were based on a generalized linear model with a logit link function and exchangeable convariance structure using generalized estimation equations. The model included fixed effects of treatment group and timepoints.

Post Treatment Period

Additional post hoc analyses were conducted to evaluate the composite endpoint during posttreatment period (days 29 to 56), as well as the proportion of patients with rebound/worsening of erythema on both CEA and SSA during posttreatment period. These analyses demonstrated that the proportions of patients with at least a 2-grade improvement from baseline on both the CEA and SSA were greater than vehicle in the Oxy 1.5%, 1.0%, and 0.5% twice-daily treatment groups at the majority of timepoints during the post-treatment period. Treatment response was similar for all 3 Oxy once-daily groups compared with vehicle at all timepoints. There were no statistically significant between-group differences at any timepoint in the twice-daily and once-daily treatment groups.

No patients had rebound or worsening of erythema, as defined by a 1-grade worsening on both the CEA and SSA scales from baseline during the posttreatment period.

5.1.2 Secondary Efficacy Analysis

The secondary efficacy variables were defined as the proportions of patients with at least a 2-grade decrease (improvement) on both CEA and SSA from baseline at hour 0.5 and hour 1.0 after application of the first dose on day 28.

The proportions of responders following twice-daily dosing at hour 0.5 on day 28 were 6.7% for all 3 Oxy treatment groups compared to 2.3% with vehicle (Table 5-3). The proportions of responders following twice-daily dosing at hour 1.0 on day 28 were 8.9%, 11.1%, and 6.7% for Oxy 1.5%, 1.0%, and 0.5%, respectively, compared to 2.3% with vehicle. There were no statistically significant differences between the Oxy and vehicle treatment groups with twice-daily dosing at hours 0.5 and 1.0.

The proportions of responders following once-daily dosing at hour 0.5 on day 28 were 6.8%, 11.4%, and 6.7% for Oxy 1.5%, 1.0%, and 0.5%, respectively, compared to 4.5% with vehicle. The proportions of responders following once-daily dosing at hour 1.0 on day 28 were 18.2%, 13.6%, and 11.1% for Oxy 1.5%, 1.0%, and 0.5%, respectively, compared to 2.3% with vehicle. There was a statistically significant difference between the Oxy 1.5% QD and vehicle treatment groups with once-daily dosing at hour 1.0.

5.1.3 Other Efficacy Analyses 5.1.3.1 Other Analyses of Primary Efficacy Variable At Least 1-Grade Improvement on Both CEA and SSA The proportions of patients with at least a 1-grade decrease (improvement) from baseline over a 12-hour period for both the CEA and SSA were significantly greater than vehicle in the Oxy 1.5%, 1.0%, and 0.5% BID treatment groups and the Oxy 1.5%, 1.0%, and 0.5% QD treatment groups on day 1, and in the Oxy 1.5% and 0.5% QD treatment groups on day 14 (Table 5-4). Statistically significant differences compared with vehicle were seen starting at hour 2 on day 1 for all Oxy treatment groups.

On the day 28 primary timepoint, the proportions of patients with at least a 1-grade improvement from baseline over a 12-hour period for both the CEA and SSA were significantly greater than vehicle in the Oxy 1.5%, 1.0%, and 0.5% QD treatment groups (Table 5-4). Statistically significant between-group differences were seen starting at hour 2 on day 28 for the Oxy 1.5% and 1.0% QD groups, and at hour 4 in the Oxy 0.5% QD group. There were few statistically significant between-group differences following twice-daily dosing on day 28 at any timepoint.

TABLE 5-3

Number (%) of Patients with at Least 2-grade Improvement on CEA and SSA from Baseline at 0.5 Hour and 1 Hour Postdose on Day 28 (mITT Population)

| | | Twice-daily Dosing | | | |
|---|---|---|---|---|---|
| Timepoint (Hour)$^a$ | Description | Oxy 1.5% BID (N = 45) | Oxy 1.0% BID (N = 45) | Oxy 0.5% BID (N = 45) | Vehicle BID (N = 44) |
| 0.5 | Responder (n [%]) | 3 (6.7) | 3 (6.7) | 3 (6.7) | 1 (2.3) |
| | Difference$^b$ | 4.4 | 4.4 | 4.4 | |
| | Difference, 90% CI | −2.73, 11.52 | −2.73, 11.52 | −2.73, 11.52 | |
| | P-value$^c$ | 0.616 | 0.616 | 0.616 | |
| 1 | Responder (n [%]) | 4 (8.9) | 5 (11.1) | 3 (6.7) | 1 (2.3) |
| | Difference$^b$ | 6.6 | 8.8 | 4.4 | |
| | Difference, 90% CI | −1.26, 14.49 | 0.32, 17.36 | −2.73, 11.52 | |
| | P-value$^c$ | 0.361 | 0.203 | 0.616 | |
| | | Once-daily Dosing | | | |
| Timepoint (Hour)$^a$ | Description | Oxy 1.5% QD (N = 44) | Oxy 1.0% QD (N = 44) | Oxy 0.5% QD (N = 45) | Vehicle QD (N = 44) |
| 0.5 | Responder (n [%]) | 3 (6.8) | 5 (11.4) | 3 (6.7) | 2 (4.5) |
| | Difference$^b$ | 2.3 | 6.8 | 2.1 | |
| | Difference, 90% CI | −5.81, 10.36 | −2.57, 16.20 | −5.86, 10.10 | |
| | P-value$^c$ | >0.999 | 0.434 | >0.999 | |
| 1 | Responder (n [%]) | 8 (18.2) | 6 (13.6) | 5 (11.1) | 1 (2.3) |
| | Difference$^b$ | 15.9 | 11.4 | 8.8 | |
| | Difference, 90% CI | 5.69, 26.13 | 2.11, 20.61 | 0.32, 17.36 | |
| | P-value$^c$ | 0.030 | 0.110 | 0.203 | |

BID = twice daily;
CEA = Clinician's Erythema Assessment;
CI = confidence interval;
mITT = modified intent-to-treat;
Oxy = oxymetazoline hydrochloride;
QD = once daily;
SSA = Subject Self-Assessment of Rrythema
Note:
The baseline value was the value collected on day 1 predose (baseline). If day 1 predose data were missing, screening visit data were used. The last observation carried forward method was used for missing data at postbaseline visits.
$^a$The timepoint was based on eCRF visit and time.
$^b$The treatment difference was calculated for active treatment group minus its vehicle of the same dose regimen.
$^c$P-values for between-treatment comparisons at a single timepoint were based on a Pearson's chi-square test or Fisher's exact test.

TABLE 5-4

Number (%) of Patients with at Least 1-grade Improvement on CEA and SSA from Baseline at 12 Hours Postdose on Days 1, 14, and 28 (mITT Population)

| | | Twice-daily Dosing | | | |
|---|---|---|---|---|---|
| Timepoint (Hour)$^a$ | Description | Oxy 1.5% BID (N = 45) | Oxy 1.0% BID (N = 45) | Oxy 0.5% BID (N = 45) | Vehicle BID (N = 44) |
| Day 1 Hour 12 | Responder (n [%]) | 23 (51.1) | 22 (48.9) | 22 (48.9) | 8 (18.2) |
| | Difference$^b$ | 32.9 | 30.7 | 30.7 | |
| | Difference, 90% CI | 17.43, 48.43 | 15.21, 46.21 | 15.21, 46.21 | |
| | P-value$^c$ | 0.001 | 0.002 | 0.002 | |
| P-value$^d$ | | <0.001 | <0.001 | <0.001 | |
| Day 14 Hour 12 | Responder (n [%]) | 21 (46.7) | 20 (44.4) | 19 (42.2) | 19 (43.2) |
| | Difference$^b$ | 3.5 | 1.3 | −1.0 | |
| | Difference, 90% CI | −13.80, 20.77 | −15.99, 18.51 | −18.16, 16.24 | |
| | P-value$^c$ | 0.741 | 0.904 | 0.927 | |
| P-value$^d$ | | 0.456 | 0.883 | 0.890 | |
| Day 28 | Responder (n [%]) | 28 (62.2) | 23 (51.1) | 18 (40.0) | 16 (36.4) |

TABLE 5-4-continued

Number (%) of Patients with at Least 1-grade Improvement on CEA and SSA from
Baseline at 12 Hours Postdose on Days 1, 14, and 28 (mITT Population)

| | | | | |
|---|---|---|---|---|
| Hour 12 | Difference[b] | 25.9 | 14.7 | 3.6 |
| | Difference, 90% CI | 9.07, 42.65 | −2.31, 31.80 | −13.24, 20.52 |
| | P-value[c] | 0.015 | 0.161 | 0.724 |
| P-value[d] | | 0.106 | 0.197 | 0.529 |

Once-daily Dosing

| Timepoint (Hour)[a] | Description | Oxy 1.5% QD (N = 44) | Oxy 1.0% QD (N = 44) | Oxy 0.5% QD (N = 45) | Vehicle QD (N = 44) |
|---|---|---|---|---|---|
| Day 1 | Responder (n [%]) | 19 (43.2) | 21 (47.7) | 18 (40.0) | 9 (20.5) |
| Hour 12 | Difference[b] | 22.7 | 27.3 | 19.5 | |
| | Difference, 90% CI | 6.93, 38.52 | 11.40, 43.15 | 3.96, 35.13 | |
| | P-value[c] | 0.022 | 0.007 | 0.045 | |
| P-value[d] | | <0.001 | <0.001 | 0.001 | |
| Day 14 | Responder (n [%]) | 19 (43.2) | 13 (29.5) | 14 (31.1) | 11 (25.0) |
| Hour 12 | Difference[b] | 18.2 | 4.5 | 6.1 | |
| | Difference, 90% CI | 1.92, 34.45 | −11.01, 20.10 | −9.47, 21.69 | |
| | P-value[c] | 0.072 | 0.632 | 0.521 | |
| P-value[d] | | 0.002 | 0.081 | 0.035 | |
| Day 28 | Responder (n [%]) | 22 (50.0) | 22 (50.0) | 17 (37.8) | 10 (22.7) |
| Hour 12 | Difference[b] | 27.3 | 27.3 | 15.1 | |
| | Difference, 90% CI | 11.14, 43.40 | 11.14, 43.40 | −0.69, 30.79 | |
| | P-value[c] | 0.008 | 0.008 | 0.123 | |
| P-value[d] | | 0.001 | 0.005 | 0.021 | |

BID = twice daily;
CEA = Clinician's Erythema Assessment;
CI = confidence interval;
mITT = modified intent-to-treat;
Oxy = oxymetazoline hydrochloride;
QD = once daily;
SSA = Subject Self-Assessment of Erythema
Note:
The baseline value was the value collected on day 1 predose (baseline). If day 1 predose data were missing, screening visit data were used. The last observation carried forward method was used for missing data at postbaseline visits.
[a]The timepoint was based on eCRF visit and time.
[b]The treatment difference was calculated for active treatment group minus its vehicle of the same dose regimen.
[c]P-values for between-treatment comparisons at a single timepoint were based on a Pearson's chi-square test or Fisher's exact test.
[d]P-values for between-treatment comparisons over a 12-hour period (ie, hours 2, 4, 6, 8, 10, and 12) were based on a generalized linear model with a logit link function and exchangeable convariance structure using generalized estimation equations. The model included fixed effects of treatment group and timepoints.

5.1.3.2 Clinician Erythema Assessment

Summary statistics of baseline and change from baseline on days 1, 14, 28, 29, 35, and 56/exit for the CEA were taken. Frequency distributions of CEA raw scores at screening and days 1, 14, 28, 29, 35, and 56/exit were calculated, and summary statistics of CEA raw scores were done.

At Least 1-Grade Improvement

The proportions of patients with at least a 1-grade decrease (improvement) from baseline over a 12-hour period for the CEA were significantly greater than vehicle for all Oxy treatment groups on day 1, for the Oxy 1.0% QD treatment group on day 14, and for the Oxy 1.5%, 1.0%, and 0.5% QD treatment groups on day 28. Statistically significant differences compared with vehicle were seen starting at hour 2 on day 1 for all Oxy treatment groups.

At Least 2-Grade Improvement

The proportions of patients with at least a 2-grade decrease (improvement) from baseline over a 12-hour period for the CEA were significantly greater than vehicle for all Oxy treatment groups on day 1, for none of the Oxy treatment groups on day 14, and for the Oxy 1.0% and 0.5% QD treatment groups on day 28. Statistically significant differences compared with vehicle were seen starting at hour 2 or 4 on day 1 for all Oxy treatment groups.

5.1.3.3 Subject Self-Assessment of Erythema

Summary statistics of baseline and change from baseline on days 1, 14, 28, 29, 35, and 56/exit for the SSA were conducted. Frequency distributions of SSA raw scores at screening and days 1, 14, 28, 29, 35, and 56/exit were calculated and summary statistics of SSA raw scores were carried out.

At Least 1-Grade Improvement

The proportions of patients with at least a 1-grade decrease (improvement) from baseline over a 12-hour period for the SSA were significantly greater than vehicle for all Oxy twice-daily treatment groups and the Oxy 1.5% and 0.5% QD treatment groups on day 1, for the Oxy 1.5% and 0.5% QD treatment groups on day 14, and for the Oxy 1.5%, 1.0%, and 0.5% QD treatment groups on day 28. Statistically significant differences compared with vehicle were seen starting at hour 2 on day 1 for a majority of the Oxy treatment groups.

At Least 2-Grade Improvement

The proportions of patients with at least a 2-grade decrease (improvement) from baseline over a 12-hour period for the SSA were significantly greater than vehicle for a majority of the Oxy twice-daily and once-daily treatment groups on day 1, for a few of the Oxy treatment groups on day 14, and for the Oxy 1.5%, 1.0% and 0.5% QD treatment groups on day 28. Statistically significant differences compared with vehicle were seen starting at hour 2 on day 1 for all of the Oxy once-daily treatment groups (Table 5-5).

TABLE 5-5

Number (%) of Patients with at Least 2-grade Improvement on SSA from
Baseline at 12 Hours Postdose on Days 1, 14 and 28 (mITT Population)

Twice-daily Dosing

| Timepoint (Hour)[a] | Description | Oxy 1.5% BID (N = 45) | Oxy 1.0% BID (N = 45) | Oxy 0.5% BID (N = 45) | Vehicle BID (N = 44) |
|---|---|---|---|---|---|
| Day 1 Hour 12 | Responder (n [%]) | 16 (35.6) | 14 (31.1) | 7 (15.6) | 5 (11.4) |
| | Difference[b] | 24.2 | 19.7 | 4.2 | |
| | Difference, 90% CI | 10.10, 38.28 | 5.98, 33.52 | −7.64, 16.03 | |
| | P-value[c] | 0.007 | 0.023 | 0.563 | |
| P-value[d] | | 0.012 | 0.015 | 0.723 | |
| Day 14 Hour 12 | Responder (n [%]) | 11 (24.4) | 18 (40.0) | 11 (24.4) | 6 (13.6) |
| | Difference[b] | 10.8 | 26.4 | 10.8 | |
| | Difference, 90% CI | −2.70, 24.31 | 11.69, 41.04 | −2.70, 24.31 | |
| | P-value[c] | 0.195 | 0.005 | 0.195 | |
| P-value[d] | | 0.356 | 0.011 | 0.821 | |
| Day 28 Hour 12 | Responder (n [%]) | 19 (42.2) | 18 (40.0) | 12 (26.7) | 10 (22.7) |
| | Difference[b] | 19.5 | 17.3 | 3.9 | |
| | Difference, 90% CI | 3.58, 35.41 | 1.44, 33.11 | −11.04, 18.91 | |
| | P-value[c] | 0.050 | 0.079 | 0.667 | |
| P-value[d] | | 0.057 | 0.056 | 0.751 | |

Once-daily Dosing

| Timepoint[a] | Description | Oxy 1.5% QD (N = 44) | Oxy 1.0% QD (N = 44) | Oxy 0.5% QD (N = 45) | Vehicle QD (N = 44) |
|---|---|---|---|---|---|
| Day 1 Hour 12 | Responder (n [%]) | 13 (29.5) | 9 (20.5) | 12 (26.7) | 3 (6.8) |
| | Difference[b] | 22.7 | 13.6 | 19.8 | |
| | Difference, 90% CI | 9.84, 35.61 | 1.88, 25.40 | 7.37, 32.33 | |
| | P-value[c] | 0.006 | 0.062 | 0.012 | |
| P-value[d] | | <0.001 | 0.003 | 0.001 | |
| Day 14 Hour 12 | Responder (n [%]) | 14 (31.8) | 8 (18.2) | 7 (15.6) | 6 (13.6) |
| | Difference[b] | 18.2 | 4.5 | 1.9 | |
| | Difference, 90% CI | 3.88, 32.49 | −8.22, 17.31 | −10.35, 14.19 | |
| | P-value[c] | 0.042 | 0.560 | 0.798 | |
| P-value[d] | | <0.001 | 0.025 | 0.143 | |
| Day 28 Hour 12 | Responder (n [%]) | 15 (34.1) | 13 (29.5) | 11 (24.4) | 5 (11.4) |
| | Difference[b] | 22.7 | 18.2 | 13.1 | |
| | Difference, 90% CI | 8.62, 36.83 | 4.44, 31.92 | −0.03, 26.19 | |
| | P-value[c] | 0.011 | 0.034 | 0.108 | |
| P-value[d] | | <0.001 | 0.004 | 0.009 | |

BID = twice daily;
CI = confidence interval;
mITT = modified intent-to-treat;
Oxy = oxymetazoline hydrochloride;
QD = once daily;
SSA = Subject Self-Assessment of Erythema
Note:
The baseline value was the value collected on day 1 predose (baseline). If day 1 predose data were missing, screening visit data were used. The last observation carried forward method was used for missing data at postbaseline visits.
[a]The timepoint was based on eCRF visit and time.
[b]The treatment difference was calculated for active treatment group minus its vehicle of the same dose regimen.
[c]P-values for between-treatment comparisons at a single timepoint were based on a Pearson's chi-square test or Fisher's exact test.
[d]P-values for between-treatment comparisons over a 12-hour period (ie, hours 2, 4, 6, 8, 10, and 12) were based on a generalized linear model with a logit link function and exchangeable convariance structure using generalized estimation equations. The model included fixed effects of treatment group and timepoints.

5.1.3.4 Subgroup Analyses of Primary Efficacy Variable

The primary efficacy variable (ie, the proportion of patients with at least a 2-grade improvement from baseline over a 12-hour period on day 28 for both the CEA and SSA) was analyzed by age group (<45, 45 to 64, and ≥65 years of age), sex (male versus female), CEA score at baseline (3 versus 4), and SSA score at baseline (3 versus 4) to compare each oxymetazoline treatment group to its vehicle.

Due to the small numbers of patients in the subgroup of males, patients aged <45 and ≥65 years, and patients with CEA or SSA scores of 4, between-treatment comparisons are not reliable due to the limited sample size.

In the subgroup of patients aged 45 to 64, female patients, and patients with a CEA or SSA score of 3, a statistically significant reduction in facial erythema was demonstrated over a 12-hour period on day 28 for a majority of the Oxy twice-daily and once-daily treatment groups compared to the vehicle groups.

In the subgroups of patients aged <45 and ≥65 years, male patients, and patients with CEA or SSA score of 4, there were no statistically significant between-group differences for any of the Oxy treatment groups versus vehicle.

Additional subgroup analyses were conducted to evaluate the proportion of patients with at least a 2-grade improvement from baseline over a 12-hour period on day 28 for the CEA by CEA score at baseline (3 versus 4), and the proportion of patients with at least a 2-grade improvement from baseline over a 12-hour period on day 28 for the SSA by SSA score at baseline (3 versus 4) to compare each oxymetazoline treatment group to its vehicle.

In the subgroup of patients with CEA score of 3, the proportion of patients with at least a 2-grade improvement from baseline for the CEA was significantly greater in the Oxy 1.0% QD treatment group compared to the vehicle groups. In the subgroup of patients with SSA score of 3, the proportion of patients with at least a 2-grade improvement from baseline for the SSA was significantly greater in the Oxy 1.5% BID and Oxy 1.0% BID treatment groups and all 3 Oxy once-daily treatment groups compared to the vehicle groups.

In the subgroups of patients with CEA or SSA scores of 4, there were no statistically significant between-group differences for any of the Oxy treatment groups versus vehicle possibly due to the limited sample size in each treatment group.

Other Measures Analyses 5.1.4 Subject Self-Assessment of Rosacea Facial Redness 5.1.4.1 at Least 1-Grade Improvement on Both CEA and SSA-2

The proportions of patients with at least a 1-grade decrease (improvement) from baseline over a 12-hour period for both the CEA and SSA-2 were significantly greater than vehicle in all Oxy treatment groups on day 1 and for the Oxy 1.5% and 1.0% QD treatment groups on day 14. Statistically significant differences compared with vehicle were seen starting at hour 2 on day 1 for all Oxy treatment groups.

On day 28, the proportions of patients with at least a 1-grade improvement from baseline over a 12-hour period for both the CEA and SSA-2 were significantly greater than vehicle in the Oxy 1.5%, 1.0%, and 0.5% QD treatment groups and the Oxy 1.0% BID group. Statistically significant differences compared with vehicle were seen starting at hour 2 on day 28 for the Oxy 1.5% and 1.0% QD groups. There were few statistically significant between-group differences following twice-daily dosing on day 28 at any timepoint.

5.1.4.2 at Least 2-Grade Improvement on Both CEA and SSA-2

On day 1, the proportions of patients with at least a 2-grade decrease (improvement) from baseline over a 12-hour period for both the CEA and SSA-2 were significantly greater than vehicle in the Oxy 1.5%, 1.0%, and 0.5% BID treatment groups and the Oxy 1.5% and 1.0% QD treatment groups, with statistically significant differences starting at hour 2 or 4 for these Oxy treatment groups compared with vehicle.

On day 14, the proportions of patients with at least a 2-grade improvement from baseline for both the CEA and SSA-2 were significantly greater than vehicle in the Oxy 1.0% BID treatment group only, with statistically significant differences compared with vehicle starting at hour 4.

On day 28 in the mITT population, a statistically significant reduction in rosacea facial redness was demonstrated in the Oxy 1.5% and 1.0% BID treatment groups and the Oxy 1.5% and 1.0% QD treatment groups compared with vehicle. Statistically significant differences compared with vehicle were seen starting at hour 4 for the Oxy 1.5% and 1.0% BID treatment groups, and at hour 1 or 2 for the Oxy 1.5% and 1.0% QD treatment groups. Similar results were observed in the PP population, whereby Oxy 1.5% and 1.0% given twice-daily or once-daily demonstrated a statistically significant reduction in rosacea facial redness compared to vehicle over a 12-hour period on day 28.

TABLE 5-6

Number (%) of Patients with at Least 2-grade Improvement on CEA and SSA-2 from Baseline at 12 Hours Postdose on Days 1, 14, and 28 (mITT Population)

| | | Twice-daily Dosing | | | |
|---|---|---|---|---|---|
| Timepoint[a] | Description | Oxy 1.5% BID (N = 45) | Oxy 1.0% BID (N = 45) | Oxy 0.5% BID (N = 45) | Vehicle BID (N = 44) |
| Day 1 | Responder (n [%]) | 4 (8.9) | 6 (11.1) | 2 (4.4) | 0 (0.0) |
| Hour 12 | Difference[b] | 8.9 | 11.1 | 4.4 | |
| | Difference, 90% CI | 1.93, 15.85 | 3.43, 18.79 | −0.59, 9.48 | |
| | P-value[c] | 0.117 | 0.056 | 0.494 | |
| | P-value[d] | <0.001 | 0.004 | 0.027 | |
| Day 14 | Responder (n [%]) | 5 (11.1) | 7 (15.6) | 3 (6.7) | 1 (2.3) |
| Hour 12 | Difference[b] | 8.8 | 13.3 | 4.4 | |
| | Difference, 90% CI | 0.32, 17.36 | 3.69, 22.88 | −2.73, 11.52 | |
| | P-value[c] | 0.203 | 0.058 | 0.616 | |
| | P-value[d] | 0.115 | 0.009 | 0.244 | |
| Day 28 | Responder (n [%]) | 7 (15.6) | 4 (8.9) | 4 (8.9) | 2 (4.5) |
| Hour 12 | Difference[b] | 11.0 | 4.3 | 4.3 | |
| | Difference, 90% CI | 0.76, 21.26 | −4.31, 13.00 | −4.31, 13.00 | |
| | P-value[c] | 0.157 | 0.677 | 0.677 | |
| | P-value[d] | 0.018 | 0.019 | 0.400 | |

| | | Once-daily Dosing | | | |
|---|---|---|---|---|---|
| Timepoint[a] | Description | Oxy 1.5% QD (N = 44) | Oxy 1.0% QD (N = 44) | Oxy 0.5% QD (N = 45) | Vehicle QD (N = 44) |
| Day 1 | Responder (n [%]) | 2 (4.5) | 2 (4.5) | 4 (8.9) | 0 (0.0) |
| Hour 12 | Difference[b] | 2.3 | 4.5 | 8.9 | |
| | Difference, 90% CI | −4.06, 8.61 | −0.60, 9.70 | 1.93, 15.85 | |
| | P-value[c] | >0.999 | 0.494 | 0.117 | |
| | P-value[d] | <0.001 | 0.023 | 0.175 | |
| Day 14 | Responder (n [%]) | 3 (6.8) | 2 (4.5) | 2 (4.4) | 2 (4.5) |
| Hour 12 | Difference[b] | 2.3 | 0.0 | −0.1 | |
| | Difference, 90% CI | −5.81, 10.36 | −7.28, 7.28 | −7.31, 7.10 | |
| | P-value[c] | >0.999 | >0.999 | >0.999 | |
| | P-value[d] | 0.161 | 0.214 | 0.823 | |
| Day 28 | Responder (n [%]) | 6 (13.6) | 5 (11.4) | 5 (11.1) | 1 (2.3) |

TABLE 5-6-continued

Number (%) of Patients with at Least 2-grade Improvement on CEA and SSA-2
from Baseline at 12 Hours Postdose on Days 1, 14, and 28 (mITT Population)

| Hour 12 | Difference[b]        | 11.4        | 9.1         | 8.8         |
|---------|----------------------|-------------|-------------|-------------|
|         | Difference, 90% CI   | 2.11, 20.61 | 0.42, 17.76 | 0.32, 17.36 |
|         | P-value[c]           | 0.110       | 0.202       | 0.203       |
| P-value[d] |                   | 0.017       | 0.013       | 0.097       |

BID = twice daily;
CEA = Clinician's Erythema Assessment;
CI = confidence interval;
mITT = modified intent-to-treat;
Oxy = oxymetazoline hydrochloride;
QD = once daily;
SSA-2 = Subject Self-Assessment of Rosacea Facial Redness
Note:
A responder was defined at least a 2-grade improvement from baseline on both CEA and SSA-2. The baseline value was the value collected on day 1 predose (baseline). If day 1 predose data were missing, screening visit data were used. The last observation carried forward method was used for missing data at postbaseline visits.
[a]The timepoint was based on eCRF visit and time.
[b]The treatment difference was calculated for active treatment group minus its vehicle of the same dose regimen.
[c]P-values for between-treatment comparisons at a single timepoint were based on a Pearson's chi-square test or Fisher's exact test.
[d]P-values for between-treatment comparisons over a 12-hour period (ie, hours 2, 4, 6, 8, 10, and 12) were based on a generalized linear model with a logit link function and exchangeable convariance structure using generalized estimation equations. The model included fixed effects of treatment group and timepoints.

5.1.4.3 Posttreatment Period

During the posttreatment period, there were no statistically significant between-group differences at any timepoint in the twice-daily and once-daily treatment groups compared with the vehicle groups for the proportions of patients with at least a 2-grade improvement from baseline on both the CEA and SSA-2.

No patients had rebound or worsening of rosacea facial redness, as defined by a 1-grade worsening on both the CEA and SSA-2 scales from baseline during the posttreatment period.

5.1.4.4 SSA-2 by Treatment Group

Summary statistics of baseline and change from baseline on days 1, 14, 28, 29, 35, and 56/exit for the SSA-2 were taken. Frequency distributions of SSA-2 raw scores at screening and days 1, 14, 28, 29, 35, and 56/exit were carried out and summary statistics of SSA-2 raw scores were carried out.

At Least 1-Grade Improvement

The proportions of patients with at least a 1-grade decrease (improvement) from baseline over a 12-hour period for the SSA-2 were significantly greater than vehicle for all Oxy twice-daily and once-daily treatment groups on day 1, for the Oxy 1.5% and 0.5% QD treatment groups on day 14, and for the Oxy 1.5%, 1.0%, and 0.5% QD treatment groups on day 28. Statistically significant differences compared with vehicle were seen starting at hour 2 on day 1 for all Oxy treatment groups.

At Least 2-Grade Improvement

The proportions of patients with at least a 2-grade decrease (improvement) from baseline over a 12-hour period for the SSA were significantly greater than vehicle for the Oxy 1.5% BID and Oxy 1.5%, 1.0%, and 0.5% QD treatment groups on day 1, for the Oxy 1.0% BID, Oxy 1.5% QD, and Oxy 1.0% QD treatment groups on day 14, and for the Oxy 1.5%, 1.0% and 0.5% QD treatment groups on day 28. Statistically significant differences compared with vehicle were seen starting at hour 2 on day 1 for all of the Oxy QD treatment groups and the Oxy 1.0% BID treatment group.

5.1.4.5 Subgroup Analyses of SSA-2

The proportions of patients with at least a 2-grade improvement from baseline over a 12-hour period on day 28 for both the CEA and SSA-2, as well for the SSA-2 alone, were analyzed by SSA-2 score at baseline (3 versus 4) to compare each oxymetazoline treatment group to its vehicle.

In the subgroup of patients with SSA-2 score of 3 at baseline, the proportion of patients with at least a 2-grade improvement from baseline for both the CEA and SSA-2 was significantly greater in the Oxy 1.5% and 1.0% BID and all 3 Oxy once-daily treatment groups compared to the vehicle groups. In this subgroup, the proportion of patients with at least a 2-grade improvement from baseline for the SSA-2 alone was significantly greater in all 3 Oxy once-daily treatment groups compared to the vehicle groups, but not for the Oxy twice-daily treatment groups.

In the subgroups of patients with SSA-2 score of 4 at baseline, there were no statistically significant between-group differences for any of the Oxy treatment groups versus vehicle.

5.1.5 Correlation Analyses

The correlation analyses included raw data and change from baseline data between the CEA and SSA, the CEA and SSA-2, and the SSA and SSA-2. These analyses demonstrated that there was a high correlation between the SSA and SSA-2 with a Spearman correlation coefficient of 0.85 (90% CI [0.842, 0.851]). The correlations between the CEA and SSA and between the CEA and SSA-2 were similar, with Spearman correlation coefficients of 0.40 (90% CI [0.390, 0.416]) and 0.43 (90% CI [0.420, 0.446]), respectively.

5.1.6 Aesthetic Questionnaire

The AQ was administered to patients on days 14 and 28 and assessed patient's facial skin type, other medication used to treat rosacea, ease of application, smell, speed of drying, greasiness/stickiness, moisturizing effect, glossy/shiny appearance, residue, and any effect of treatment on routine application of makeup or sunscreen.

The largest proportion of patients in all treatment groups had combination skin.

Other medications used to treat rosacea were taken into consideration.

The largest proportion of patients in all treatment groups stated that it took more than 15 minutes for the study medication to dry, but that it was not bothersome to wait for the study medication to dry. A majority of all patients (48.3%) preferred a cream product rather than other types of products that were not used in this study, ie, lotion (18.5%), pad (8.7%), gel (7.9%), spray/mist (6.7%), foam (2.8%), and ointment (2.2%).

On days 14 and 28, the largest proportion of patients in all treatment groups stated that the study medication was easy to apply, was fragrance-free, was absorbed and dried quickly, was not greasy or sticky, was moisturizing/hydrating, did not interfere with their facial make-up routine, moisturizer or sunscreen application, and did not leave a residue on their face after it dried.

5.1.7 Digital Image Analyses

The results of the exploratory DIA data (for once-daily dosing only) were analyzed by Canfield Scientific, Inc.

In summary, among the 6 measures evaluated from the DIA (ie, Fractional Area, Erythema Severity, Erythema Redness, Erythema Contrast, Intensity of Erythema, and Erythema Visibility), Fractional Area had the best correlation with the CEA scale, with a Spearman correlation coefficient of 0.47 (95% CI [0.436, 0.498]. In general, there was a good differentiation on the improvement from baseline in Fractional Area between the Oxy once-daily groups and the vehicle once-daily group.

5.2 Health Outcomes Analyses

A summary of the proportion of patients with at least a 1-grade improvement on each question of the PRO measures from baseline on day 28 is provided below. Note that all PRO measures were administered at predose for validation purposes, which may have resulted in lower scores.

5.2.1 Symptom Assessment for Rosacea Facial Redness

Patients were asked to assess their symptoms in the present moment ("right now") on visit days 1, 14, and 28. At the day 28 assessment, the proportions of patients with at least a 1-grade improvement on each question of the Symptom Assessment were similar for all treatment arms. The proportions ranged from 35.6% to 68.9% for the active treatment groups compared to 31.8% to 72.7% for the vehicle groups.

On day 28, the mean changes from baseline in the score for most Symptom Assessment questions were not significantly different for the treatment groups.

The frequency distributions of responses for each Symptom Assessment question are shown by treatment group and visit. These frequency distributions were generally similar for the treatment groups regardless of the dosing regimen.

The results of the treatment group are not substantially different from the vehicle groups because the PRO was administered predose.

5.2.2 Impact Assessment for Rosacea Facial Redness

Patients were asked to assess the impacts related to erythema associated rosacea over the past 7 days on visit days 1, 14, and 28. The proportions of patients with at least a 1-grade improvement at the day 28 assessment on each question of the Impact Assessment were similar for all treatment arms. The proportions ranged from 21.4% to 77.8% for the active treatment groups compared to 23.3% to 77.3% for the vehicle groups.

On day 28, the mean changes from baseline in the score for most Impact Assessment questions were not significantly different for the treatment groups.

The frequency distributions of responses for each Impact Assessment question are shown by treatment group and visit. These frequency distributions were generally similar for all the treatment groups regardless of the dosing regimen.

The similarity in the results between the treatment and vehicle groups may be due to the fact that oxymetazoline has a transient effect on erythema. Although the recall period was 7 days, the variable nature of the condition may have impacted patients' responses.

5.2.3 Satisfaction Assessment for Rosacea Facial Redness

Patients were asked to assess their satisfaction in the present moment ("right now") on visit days 1, 14, and 28. At the day 28 assessment, the proportions of patients with at least a 1 grade improvement on each question of the Satisfaction Assessment were similar for all treatment arms. The reported proportions were up to 43.2% for the active treatment groups and up to 45.2% for the vehicle groups respectively.

On day 28, the mean changes from baseline in the score for each Satisfaction Assessment question were not significantly different for the treatment groups.

The frequency distribution of responses for each Satisfaction Assessment question by treatment group were similar at each follow up visit.

The results of the treatment group are not substantially different from the vehicle groups because the PRO was administered predose.

5.3 Pharmacokinetic Results 5.3.1 Anomalous Concentration Values

The following patients had timepoints that were considered as outlier values according to SOP DSEPK-001: 1100 (day 14, 12 hour), 1138 (day 28, 2 hour), 1180 (day 1, 8 hour), 1188 (day 28, 8 hour), 1222 (day 28, 8 hour), 1236 (day 1, 2 hour), 1247 (day 14, predose), 1281 (day 1, all timepoints), 1274 (day 1, 4, and 8 hours), 1286 (day 1, all timepoints and day 28, 12 hour), 1289 (day 1, all timepoints), 1316 (day 28, all timepoints), 1349 (day 1, all timepoints), 1350 (day 1, 12 hour), and 1458 (day 28, predose). In addition, the following patients had measurable predose values on day 1 which were excluded from the analysis: 1155, 1097, 1283, 1316, 1356, and 1249. Pharmacokinetic parameters for these patients were calculated without these outlier values.

5.3.2 Missing Patient Data

A total of 238 samples from 36 patients on active treatment were not included in the data analysis. These included 0.11%, 3.64%, and 4.89% of samples from the Oxy 1.5%, 1.0%, and 0.5% QD groups, respectively, and 6.33%, 7.00%, and 4.56% of samples from the Oxy 1.5%, 1.0%, and 0.5% BID groups, respectively.

- 138 samples from 24 patients were not collected due to a missed visit or difficulties in drawing blood
- 86 samples from 7 patients were not collected due to early exit from the study
- 9 samples from 4 patients were collected, however, were not able to be located at the time of analysis, therefore, were considered missing
- 1 sample from 1 patient was not able to be analyzed due to insufficient volume
- 4 samples from 2 patients were analyzed, however, their data was not reportable due to re-assay failure No adjustment or imputation was utilized for missing values. Missing samples did not impact the overall objective of the study.

Pharmacokinetic Evaluation

Pharmacokinetic parameters, where applicable, were calculated for each patient following dermal administration of oxymetazoline cream and are summarized in Table 5-7. The maximum concentrations in the once-daily and twice-daily dose groups were observed between 6 to 12 hours (median $T_{max}$) and 4 to 6 hours (median $T_{max}$) postdose, respectively. A short $T_{max}$ for the twice-daily dosing regimens was observed because the second dose on each day was administered 6 hours after the first dose, and the first dose on the next day was administered 18 hours after the second dose on the previous day. Following once-daily dosing, the mean Ca, in the 1.5% dose group on day 28 was 98.0 pg/mL which was similar to the 115 pg/mL mean $C_{max}$ observed in the Oxy 1.5% BID treatment group on day 28. The highest mean $AUC_{0-24}$ following administration of 1.5% once-daily or BID was 1680 and 2660 pg·hr/mL, respectively. With an increase in dosing frequency (twice-daily), there did not appear to be an equal increase in systemic exposure when compared to once-daily dosing. Across all treatment groups, the mean $C_{max}$ and $AUC_{0-24}$ were generally lower than that observed following a single administration of Afrin® nasal spray (0.05% oxymetazoline), where the mean $C_{max}$ was 245 pg/mL and the mean $AUC_{0-12}$ was 1741 pg·hr/mL (oxymetazoline clinical study). A plot of the trough concentrations indicates that steady state may have been reached by the second dose for the once-daily groups and after the third dose for the twice-daily groups. Steady state systemic exposure to oxymetazoline appeared to increase approximately dose proportionally following once-daily or twice-daily dermal administration of 0.5%, 1.0%, and 1.5% oxymetazoline cream. Following 28 days of dosing, a mean accumulation ratio of approximately 2 was observed across all once-daily treatment groups. Increased accumulation was observed in the twice-daily treatment groups, with a mean accumulation ratio between 4.86 and 6.48 when comparing AUC after the first dose on days 1 and 28. A prolonged effective half-life was observed following dermal administration of oxymetazoline cream (mean 18-28 hours) when compared to the terminal half-life for Afrin® nasal spray (mean 5 hours, oxymetazoline clinical study), probably attributable to the different routes of administration.

respectively), and with all 3 doses of oxymetazoline cream (1.5%, 1.0%, and 0.5%) following once-daily dosing (p=0.012, p=0.006, and p=0.049, respectively).

The proportions of responders in the twice-daily treatment groups at hour 4 (peak timepoint) on day 28 were 22.2%, 20.0% and 11.1% with Oxy 1.5%, 1.0%, and 0.5%, respectively, compared to 6.8% with vehicle. The proportions of responders in the twice-daily treatment groups were maintained at hour 12 on day 28, with 15.6%, 11.1% and 13.3% in the Oxy 1.5%, 1.0%, and 0.5% groups, respectively, compared to only 4.5% in the vehicle group.

The proportions of responders in the once-daily treatment groups at hour 4 (peak timepoint) on day 28 were 27.3%, 31.8% and 17.8% with Oxy 1.5%, 1.0%, and 0.5%, respectively, compared to 4.5% with vehicle. The proportions of responders in the once-daily treatment groups were maintained at hour 12 on day 28, with 13.6%, 13.6%, and 13.3% in the Oxy 1.5%, 10%, and 0.5% groups, respectively, compared to only 2.3% in the vehicle group.

A statistically significant difference based on the composite 2-grade improvement was observed as early as 2 hours after the first application on day 1 for a majority of the Oxy treatment groups compared with vehicle.

The pair-wise comparison showed no statistically significant differences in response rates over a 12-hour time period on day 28 between any of the Oxy twice-daily or once-daily treatment groups, demonstrating that twice-daily dosing did not provide any significant

TABLE 5-7

Mean Pharmacokinetic Parameters Following Dermal Administration of Oxymetazoline Cream to Patients with Erythema Associated with Rosacea

| Treatment Group | Day | $T_{max}$ (hr) | $C_{max}$ (pg/mL) | $AUC_{0-24}$[a] (pg·hr/mL) | $AUC_{0-6}$[b] (pg·hr/mL) | $R_0$[c] | $T_{eff}$[d] (hr) |
|---|---|---|---|---|---|---|---|
| Oxy 0.5% QD | 1 | 12 (4, 24) | 35.0 ± 56.7 | 467 ± 558 | NA | 2.13 ± 0.82 | 25.9 ± 14.2 |
| | 28 | 6 (0, 24) | 41.5 ± 30.0 | 590 ± 518 | NA | | |
| Oxy 1.0% QD | 1 | 12 (2, 24) | 60.5 ± 53.9 | 895 ± 798 | NA | 1.75 ± 0.83 | 18.8 ± 14.9 |
| | 28 | 10 (0, 24) | 66.4 ± 67.1 | 1050 ± 992 | NA | | |
| Oxy 1.5% QD | 1 | 10 (4, 24) | 68.5 ± 54.6 | 1090 ± 794 | NA | 2.26 ± 1.42 | 28.0 ± 24.3 |
| | 28 | 8 (0, 24) | 98.0 ± 79.5 | 1680 ± 1430 | NA | | |
| Oxy 0.5% BID | 1 | 6 (2, 6) | 20.6 ± 11.1 | 563 ± 357 | 49.9 ± 40.8 | 4.99 ± 5.18 | 18.5 ± 21.6 |
| | 28 | 6 (0, 6) | 39.0 ± 29.7 | 752 ± 581 | 168 ± 129 | | |
| Oxy 1.0% BID | 1 | 6 (4, 6) | 56.9 ± 68.9 | 1400 ± 1220 | 155 ± 154 | 6.48 ± 6.05 | 24.7 ± 25.3 |
| | 28 | 4 (0, 6) | 68.8 ± 61.1 | 1530 ± 922 | 311 ± 252 | | |
| Oxy 1.5% BID | 1 | 6 (4, 6) | 62.6 ± 65.7 | 1740 ± 942 | 183 ± 152 | 4.86 ± 3.45 | 18.0 ± 14.4 |
| | 28 | 6 (0, 6) | 115 ± 111 | 2660 ± 2170 | 563 ± 609 | | |

$C_{max}$ = maximum observed plasma concentration;
BID = twice daily,
NA = not available,
QD = once daily;
$T_{max}$ = time corresponding to maximum observed plasma concentration
Note,
all data were reported as mean ± standard deviation, except for $T_{max}$ which was reported as median (min, max).
[a] $AUC_{0-24}$ for twice-daily groups calculated as the sum of $AUC_{0-6}$ and $AUC_{0-24}$
[b] $AUC_{0-6}$ calculated for twice-daily groups only; represents AUC after morning dose on day 1 and day 28
[c] $R_0$ = accumulation ratio = $AUC_{Day\ 28}/AUC_{Day\ 1}$
[d] $T_{eff}$ = effective half-life = $(\tau \times \ln 0.5)/\ln(1 - 1/R_0)$
Source: Table 16.1.13.1-1

5.4 Efficacy Conclusions

A statistically significant reduction in facial erythema as measured by the composite assessment, ie, the proportions of patients with at least a 2-grade decrease (improvement) from baseline over a 12-hour period for both the CEA and SSA on day 28, was demonstrated with the 1.5% and 1.0% doses of oxymetazoline cream following twice-daily dosing (p=0.006 and p=0.021, improvement over once-daily dosing for any of the Oxy treatment groups. A numerically higher response rate was observed for Oxy 1.0% QD versus Oxy 0.5% QD at most timepoints. When comparing the Oxy 1.5% QD and the 1.0% QD doses, the response rates were similar.

For the secondary efficacy variables (defined as the proportions of patients with at least a 2-grade improvement on both the CEA and SSA from baseline at hour 0.5 and hour 1.0 after application of the first dose on day 28), only the Oxy 1.5% QD treatment group showed statistically significant differences compared with vehicle at hour 1.0.

The response rates on day 28 were higher compared with response rates on day 1 for all Oxy treatment groups, demonstrating that no tachyphylaxis was observed during the study.

A statistically significant reduction in rosacea facial redness, as demonstrated by the proportions of patients with at least a 2-grade decrease (improvement) from baseline over a 12-hour period for both the CEA and SSA-2, was observed with Oxy 1.5% and 1.0% given twice-daily and once-daily compared with vehicle on day 28, with responses observed as early as day 1.

Correlation analyses demonstrated that there was a high correlation between the SSA and SSA-2 with a Spearman correlation coefficient of 0.85 (90% CI [0.842, 0.851]).

There were no statistically significant between-group differences in the proportions of responders at any timepoint during the 4-week posttreatment period. During this follow-up phase, During this follow-up phase, no patients had rebound or worsening of erythema, as defined by a 1-grade worsening from baseline on both of the CEA and SSA scales, as well as both of the CEA and SSA-2 scales.

Subgroup analyses of the primary efficacy variable demonstrated that treatment with oxymetazoline was efficacious in the reduction of erythema regardless of sex, age, CEA score at baseline, or SSA score at baseline.

6. Safety Evaluation 6.1 Extent of Exposure

A total of 357 patients were enrolled into the study, of which 356 patients received at least 1 dose of study medication and were included in the safety population. One patient was randomized by error; this patient did not receive study treatment and was not included in the safety population. A total of 179 patients received twice-daily treatment (135 Total Oxy and 44 vehicle), and 177 patients received once-daily treatment (133 Total Oxy and 44 vehicle).

The mean total study duration was 55.1 days and the mean total treatment duration was 27.8 days. Mean exposure times were similar across all treatment groups.

6.2 Adverse Events 6.2.1 Brief Summary of Adverse Events

Treatment-emergent adverse events (TEAEs), regardless of causality, that occurred during the study period were reported in 33.1% (118/356) of all patients, and treatment-related TEAEs were reported in 9.8% (35/356) of all patients (Table 6-1).

Following twice-daily dosing, 32.6% (44/135) of the Oxy-treated patients and 43.2% (19/44) of the vehicle-treated patients had TEAEs, and 12.6% (17/135) of the Oxy-treated patients and 11.4% (5/44) of the vehicle-treated patients had treatment-related TEAEs. The proportions of patients reporting TEAEs and treatment-related TEAEs were similar across the 3 Oxy twice-daily treatment groups.

Following once-daily dosing, 33.8% (45/133) of the Oxy-treated patients and 22.7% (10/44) of the vehicle-treated patients had TEAEs, and 9.8% (13/133) of the Oxy-treated patients and 0% (0/44) of the vehicle-treated patients had treatment-related TEAEs. The proportions of patients reporting TEAEs and treatment-related TEAEs were slightly higher in the Oxy 1.5% QD group than the Oxy 1.0% and 0.5% QD groups.

Across all treatment groups, the most commonly reported TEAEs (occurring in ≥2% patients overall) included headache, contact dermatitis, upper respiratory tract infection, application site papules, application site erythema, and application site acne.

There were no deaths reported during the study. There were 5 serious adverse events reported in 3 patients (1 Oxy 1.0% BID, 1 Oxy 1.00% QD, and 1 vehicle); none of these was considered to be related to study treatment. One patient (in the vehicle group) discontinued the study due to serious adverse events.

A total of 2.8% (10/356) of patients discontinued the study due to TEAEs: 8 patients treated with oxymetazoline (2 Oxy 1.5% BID, 3 Oxy 1.0% BID, and 1 each in the Oxy 0.5% BID, Oxy 1.0% QD, and Oxy 0.5% QD treatment groups) and 2 patients treated with vehicle. The most frequently reported adverse events leading to study discontinuation were application site adverse events; all of these events occurred in Oxy-treated patients and were considered by the investigator to be treatment-related.

Treatment-related application site adverse events were reported in 28 oxymetazoline-treated patients (7 Oxy 1.5% BID, 4 Oxy 1.0% BID, 5 Oxy 0.5% BID, 6 Oxy 1.5% QD, 3 Oxy 1.0% QD, and 3 Oxy 0.5% QD) and 5 vehicle-treated patients (Table 6-4). A majority of the events were mild or moderate in severity and resolved without sequelae. Seven patients (all treated with oxymetazoline) discontinued from the study due to treatment-related application site adverse events.

TABLE 6-1

Overall Rates of Treatment-emergent Adverse Events (Safety Population)

| | Number (%) of Patients | | | | | | |
|---|---|---|---|---|---|---|---|
| Adverse Event Category | Oxy 1.5% BID (N = 45) | Oxy 1.0% BID (N = 45) | Oxy 0.5% BID (N = 45) | Vehicle BID (N = 44) | Oxy 1.5% QD (N = 44) | Oxy 1.0% QD (N = 44) | Oxy 0.5% QD (N = 45) |
| All adverse events | 16 (35.6) | 12 (26.7) | 16 (35.6) | 19 (43.2) | 20 (45.5) | 10 (22.7) | 15 (33.3) |
| Treatment-related adverse events | 7 (15.6) | 5 (11.1) | 5 (11.1) | 5 (11.4) | 6 (13.6) | 4 (9.1) | 3 (6.7) |
| Serious adverse events | 0 (0.0) | 1 (2.2) | 0 (0.0) | 0 (0.0) | 0 (0.0) | 1 (2.3) | 0 (0.0) |
| Discontinuations due to adverse events | 2 (4.4) | 3 (6.7) | 1 (2.2) | 1 (2.3) | 0 (0.0) | 1 (2.3) | 1 (2.2) |

TABLE 6-1-continued

Overall Rates of Treatment-emergent Adverse Events (Safety Population)

| Adverse Event Category | Number (%) of Patients | | | | | |
|---|---|---|---|---|---|---|
| | Vehicle QD (N = 44) | Total Oxy BID (N = 135) | Total Oxy QD (N = 133) | Total Oxy (N = 268) | Total Vehicle (N = 88) | Total (N = 356) |
| All adverse events | 10 (22.7) | 44 (32.6) | 45 (33.8) | 89 (33.2) | 29 (33.0) | 118 (33.1) |
| Treatment-related adverse events | 0 (0.0) | 17 (12.6) | 13 (9.8) | 30 (11.2) | 5 (5.7) | 35 (9.8) |
| Serious adverse events | 1 (2.3) | 1 (0.7) | 1 (0.8) | 2 (0.7) | 1 (1.1) | 3 (0.8) |
| Discontinuations due to adverse events | 1 (2.3) | 6 (4.4) | 2 (1.5) | 8 (3.0) | 2 (2.3) | 10 (2.8) |

BID = twice daily;
Oxy = oxymetazoline hydrochloride;
QD = once daily
Note:
Treatment-emergent adverse events include all reported events that began during the study or increased in severity compared with baseline. Treatment-related adverse events include those that in the investigator's opinion may have been caused by the study medication with reasonable possibility. Within each preferred term, a patient is counted at most once.

6.2.2 All Adverse Events

TEAEs were reported in 33.1% (118/356) of all patients during the study period. TEAEs that were reported in ≥2 patients in any treatment group are provided in Table 6-2.

Following twice-daily dosing, 32.6% (44/135) of the Oxy-treated patients and 43.2% (19/44) of the vehicle-treated patients had TEAEs. The proportions of patients were similar across the Oxy treatment groups, with 35.6%, 26.7%, and 35.6% of patients reporting TEAEs in the Oxy 1.5%, 1.0%, and 0.5% BID groups, respectively.

Following once-daily dosing, 33.8% (45/133) of the Oxy-treated patients and 22.7% (10/44) of the vehicle-treated patients had TEAEs. There was an higher proportion of patients reporting TEAEs with Oxy 1.5% QD (45.5%) than Oxy 1.0% and 0.5% QD (22.7% and 33.3%, respectively).

Across all treatment groups, the most commonly reported TEAE was headache in 4.8% (17/356) of patients. Headache occurred in a similar proportion of patients treated with oxymetazoline (4.9% [13/268]) and vehicle (4.5% [4/88]). Two patients (both in the Oxy 1.5% BID group) had headache that was considered by the investigator to be related to study treatment.

Other commonly reported TEAEs (occurring in ≥2% patients overall) included: application site dermatitis in 2.5% (9/356) of all patients, contact dermatitis in 2.2% (8/356) of all patients; upper respiratory tract infection in 2.5% (9/356) of patients; and application site papules, application site erythema, and application site acne, each occurring in 2.0% (7/356) of all patients. Contact dermatitis was reported in 2.6% (7/268) of Oxy-treated patients and 1.1% (1/88) of vehicle-treated patients. The incidence of upper respiratory tract infection was similar across all treatment groups. Application site dermatitis, application site papules, and application site erythema were reported only in the Oxy treatment groups. Application site acne occurred in 1.5% (4/268) of Oxy-treated patients and 3.4% (3/88) of vehicle-treated patients.

TABLE 6-2

Treatment-emergent Adverse Events Occurring in ≥2 Patients in Any Randomized Treatment Group (Safety Population)

| System Organ Class | Preferred Term | Number (%) of Patients | | | | | | |
|---|---|---|---|---|---|---|---|---|
| | | Oxy 1.5% BID (N = 45) | Oxy 1.0% BID (N = 45) | Oxy 0.5% BID (N = 45) | Vehicle BID (N = 44) | Oxy 1.5% QD (N = 44) | Oxy 1.0% QD (N = 44) | Oxy 0.5% QD (N = 45) |
| Overall | | 16 (35.6) | 12 (26.7) | 16 (35.6) | 19 (43.2) | 20 (45.5) | 10 (22.7) | 15 (33.3) |
| Gastrointestinal disorders | Overall | 1 (2.2) | 1 (2.2) | 3 (6.7) | 3 (6.8) | 1 (2.3) | 0 (0.0) | 1 (2.2) |
| | Vomiting | 0 (0.0) | 0 (0.0) | 0 (0.0) | 2 (4.5) | 0 (0.0) | 0 (0.0) | 0 (0.0) |
| General disorders and administration site conditions | Overall | 8 (17.8) | 4 (8.9) | 5 (11.1) | 7 (15.9) | 8 (18.2) | 6 (13.6) | 4 (8.9) |
| | Application site dermatitis | 2 (4.4) | 3 (6.7) | 1 (2.2) | 0 (0.0) | 0 (0.0) | 3 (6.8) | 0 (0.0) |
| | Application site papules | 2 (4.4) | 0 (0.0) | 2 (4.4) | 0 (0.0) | 2 (4.5) | 1 (2.3) | 0 (0.0) |
| | Application site erythema | 2 (4.4) | 0 (0.0) | 1 (2.2) | 0 (0.0) | 1 (2.3) | 1 (2.3) | 2 (4.4) |
| | Application site pruritus | 1 (2.2) | 1 (2.2) | 0 (0.0) | 0 (0.0) | 2 (4.5) | 1 (2.3) | 0 (0.0) |
| | Application site acne | 1 (2.2) | 0 (0.0) | 0 (0.0) | 3 (6.8) | 1 (2.3) | 1 (2.3) | 1 (2.2) |
| | Application site paraesthesia | 1 (2.2) | 0 (0.0) | 0 (0.0) | 0 (0.0) | 2 (4.5) | 0 (0.0) | 0 (0.0) |
| Infections and infestations | Overall | 4 (8.9) | 1 (2.2) | 2 (4.4) | 4 (9.1) | 4 (9.1) | 2 (4.5) | 4 (8.9) |
| | Upper respiratory tract infection | 2 (4.4) | 1 (2.2) | 1 (2.2) | 1 (2.3) | 1 (2.3) | 1 (2.3) | 1 (2.2) |

TABLE 6-2-continued

Treatment-emergent Adverse Events Occurring in ≥2 Patients in Any Randomized Treatment Group (Safety Population)

|  |  |  |  |  |  |  |  |  |
|---|---|---|---|---|---|---|---|---|
| Investigations | Nasopharyngitis | 2 (4.4) | 0 (0.0) | 0 (0.0) | 0 (0.0) | 0 (0.0) | 0 (0.0) | 0 (0.0) |
|  | Bronchitis | 0 (0.0) | 0 (0.0) | 0 (0.0) | 1 (2.3) | 0 (0.0) | 0 (0.0) | 2 (4.4) |
|  | Overall | 3 (6.7) | 1 (2.2) | 3 (6.7) | 3 (6.8) | 1 (2.3) | 1 (2.3) | 0 (0.0) |
|  | Electrocardiogram T wave inversion | 1 (2.2) | 0 (0.0) | 2 (4.4) | 0 (0.0) | 0 (0.0) | 1 (2.3) | 0 (0.0) |
| Musculoskeletal and connective tissue disorders | Overall | 0 (0.0) | 0 (0.0) | 0 (0.0) | 1 (2.3) | 2 (4.5) | 1 (2.3) | 1 (2.2) |
|  | Arthralgia | 0 (0.0) | 0 (0.0) | 0 (0.0) | 0 (0.0) | 2 (4.5) | 1 (2.3) | 0 (0.0) |
| Nervous system disorders | Overall | 5 (11.1) | 4 (8.9) | 1 (2.2) | 5 (11.4) | 1 (2.3) | 2 (4.5) | 5 (11.1) |
|  | Headache | 4 (8.9) | 3 (6.7) | 1 (2.2) | 3 (6.8) | 0 (0.0) | 1 (2.3) | 4 (8.9) |
|  | Migraine | 1 (2.2) | 0 (0.0) | 0 (0.0) | 0 (0.0) | 0 (0.0) | 2 (4.5) | 0 (0.0) |
|  | Dizziness | 0 (0.0) | 0 (0.0) | 0 (0.0) | 2 (4.5) | 0 (0.0) | 0 (0.0) | 0 (0.0) |
| Respiratory, thoracic and mediastinal disorders | Overall | 0 (0.0) | 2 (4.4) | 0 (0.0) | 0 (0.0) | 1 (2.3) | 0 (0.0) | 0 (0.0) |
|  | Rhinitis seasonal | 0 (0.0) | 0 (0.0) | 0 (0.0) | 0 (0.0) | 0 (0.0) | 0 (0.0) | 0 (0.0) |
| Skin and subcutaneous tissue disorders | Overall | 3 (6.7) | 0 (0.0) | 4 (8.9) | 0 (0.0) | 1 (2.3) | 1 (2.3) | 2 (4.4) |
|  | Dermatitis contact | 2 (4.4) | 0 (0.0) | 1 (2.2) | 0 (0.0) | 1 (2.3) | 1 (2.3) | 2 (4.4) |

| System Organ Class | Preferred Term | Number (%) of Patients | | | | | |
|---|---|---|---|---|---|---|---|
|  |  | Vehicle QD (N = 44) | Total Oxy BID (N = 135) | Total Oxy QD (N = 133) | Total Oxy (N = 268) | Total Vehicle (N = 88) | Total (N = 356) |
|  | Overall | 10 (22.7) | 44 (32.6) | 45 (33.8) | 89 (33.2) | 29 (33.0) | 118 (33.1) |
| Gastrointestinal disorders | Overall | 0 (0.0) | 5 (3.7) | 2 (1.5) | 7 (2.6) | 3 (3.4) | 10 (2.8) |
|  | Vomiting | 0 (0.0) | 0 (0.0) | 0 (0.0) | 0 (0.0) | 2 (2.3) | 2 (0.6) |
| General disorders and administration site conditions | Overall | 0 (0.0) | 17 (12.6) | 18 (13.5) | 35 (13.1) | 7 (8.0) | 42 (11.8) |
|  | Application site dermatitis | 0 (0.0) | 6 (4.4) | 3 (2.3) | 9 (3.4) | 0 (0.0) | 9 (2.5) |
|  | Application site papules | 0 (0.0) | 4 (3.0) | 3 (2.3) | 7 (2.6) | 0 (0.0) | 7 (2.0) |
|  | Application site erythema | 0 (0.0) | 3 (2.2) | 4 (3.0) | 7 (2.6) | 0 (0.0) | 7 (2.0) |
|  | Application site pruritus | 0 (0.0) | 2 (1.5) | 3 (2.3) | 5 (1.9) | 0 (0.0) | 5 (1.4) |
|  | Application site acne | 0 (0.0) | 1 (0.7) | 3 (2.3) | 4 (1.5) | 3 (3.4) | 7 (2.0) |
|  | Application site paraesthesia | 0 (0.0) | 1 (0.7) | 2 (1.5) | 3 (1.1) | 0 (0.0) | 3 (0.8) |
| Infections and infestations | Overall | 3 (6.8) | 7 (5.2) | 10 (7.5) | 17 (6.3) | 7 (8.0) | 24 (6.7) |
|  | Upper respiratory tract infection | 1 (2.3) | 4 (3.0) | 3 (2.3) | 7 (2.6) | 2 (2.3) | 9 (2.5) |
|  | Nasopharyngitis | 0 (0.0) | 2 (1.5) | 0 (0.0) | 2 (0.7) | 0 (0.0) | 2 (0.6) |
|  | Bronchitis | 0 (0.0) | 0 (0.0) | 2 (1.5) | 2 (0.7) | 1 (1.1) | 3 (0.8) |
| Investigations | Overall | 1 (2.3) | 7 (5.2) | 2 (1.5) | 9 (3.4) | 4 (4.5) | 13 (3.7) |
|  | Electrocardiogram T wave inversion | 1 (2.3) | 3 (2.2) | 1 (0.8) | 4 (1.5) | 1 (1.1) | 5 (1.4) |
| Musculoskeletal and connective tissue disorders | Overall | 1 (2.3) | 0 (0.0) | 4 (3.0) | 4 (1.5) | 2 (2.3) | 6 (1.7) |
|  | Arthralgia | 0 (0.0) | 0 (0.0) | 3 (2.3) | 3 (1.1) | 0 (0.0) | 3 (0.8) |
| Nervous system disorders | Overall | 2 (4.5) | 10 (7.4) | 8 (6.0) | 18 (6.7) | 7 (8.0) | 25 (7.0) |
|  | Headache | 1 (2.3) | 8 (5.9) | 5 (3.8) | 13 (4.9) | 4 (4.5) | 17 (4.8) |
|  | Migraine | 0 (0.0) | 1 (0.7) | 2 (1.5) | 3 (1.1) | 0 (0.0) | 3 (0.8) |
|  | Dizziness | 0 (0.0) | 0 (0.0) | 0 (0.0) | 0 (0.0) | 2 (2.3) | 2 (0.6) |
| Respiratory, thoracic and mediastinal disorders | Overall | 3 (6.8) | 2 (1.5) | 1 (0.8) | 3 (1.1) | 3 (3.4) | 6 (1.7) |
|  | Rhinitis seasonal | 2 (4.5) | 0 (0.0) | 0 (0.0) | 0 (0.0) | 2 (2.3) | 2 (0.6) |
| Skin and subcutaneous tissue disorders | Overall | 1 (2.3) | 7 (5.2) | 4 (3.0) | 11 (4.1) | 1 (1.1) | 12 (3.4) |
|  | Dermatitis contact | 1 (2.3) | 3 (2.2) | 4 (3.0) | 7 (2.6) | 1 (1.1) | 8 (2.2) |

BID = twice daily;
Oxy = oxymetazoline hydrochloride;
QD = once daily
Note:
Treatment-emergent adverse events include all reported events that began during the study or increased in severity compared with baseline, regardless of relationship to treatment. Within each combination of preferred term and system organ class, a patient was counted at most once.

Additional post hoc analyses were conducted to evaluate adverse events that occurred during treatment period and posttreatment period. Adverse events during the treatment period included all reported events that began during the study or increased in severity during the treatment period of the study compared with baseline, regardless of relationship to treatment. Adverse events during the posttreatment period included all reported events that began on day 29 or after, or increased in severity compared with the same adverse events reported prior to day 29, regardless of relationship to treatment.

Adverse events during the treatment period were reported in 27.2% (97/356) of all patients: 26.7% (36/135) of the Oxy-treated patients and 34.1% (15/44) of the vehicle-treated patients following twice-daily dosing, and 28.6% (38/133) of the Oxy-treated patients and 18.2% (8/44) of the vehicle-treated patients following once-daily dosing. A majority of the adverse events reported during the treatment period were considered to be of mild or moderate severity.

Adverse events were reported in 7.9% (28/356) of all patients during the posttreatment period: 7.4% (10/135) of the Oxy-treated patients and 11.4% (5/44) of the vehicle-treated patients following twice-daily dosing, and 8.3% (11/133) of the Oxy-treated patients and 4.5% (2/44) of the vehicle-treated patients following once-daily dosing. Application site events included 1 case of application site scab in the vehicle BID treatment group, and 1 case each of application site acne, application site papules, and application site dermatitis in the Oxy once-daily treatment group. All of the adverse events reported during the posttreatment period were considered to be of mild or moderate severity, with the exception of severe arthralgia and severe headache reported in the Oxy 1.0% QD group.

6.2.3 Treatment-related Adverse Events 6.2.3.1 all Treatment-Related Adverse Events Treatment-related TEAEs (ie, TEAEs that, in the investigator's opinion, may have been caused by the study medication) were reported in 9.8% (35/356) of all patients (Table 6-3).

Following twice-daily dosing, 12.6% (17/135) of the Oxy-treated patients and 11.4% (5/44) of the vehicle-treated patients had treatment-related TEAEs. The proportions of patients were similar across the Oxy treatment groups, with 15.6%, 11.1%, and 11.1% of patients reporting treatment-related TEAEs in the Oxy 1.5%, 1.0%, and 0.5% BID groups, respectively.

Following once-daily dosing, 9.8% (13/133) of the Oxy-treated patients and 0% (0/44) of the vehicle-treated patients had treatment-related TEAEs. There was an increased proportion of patients reporting treatment-related TEAEs with increasing Oxy doses: 13.6%, 9.1%, and 6.7% of patients in the Oxy 1.5%, 1.0%, and 0.5% QD groups, respectively.

The most frequently reported treatment-related TEAEs were application site events; these are discussed further in Section 6.2.3.2.

TABLE 6-3

All Treatment-related Treatment-emergent Adverse Events (Safety Population)

| System Organ Class | Preferred Term | Oxy 1.5% BID (N = 45) | Oxy 1.0% BID (N = 45) | Oxy 0.5% BID (N = 45) | Vehicle BID (N = 44) | Oxy 1.5% QD (N = 44) | Oxy 1.0% QD (N = 44) | Oxy 0.5% QD (N = 45) |
|---|---|---|---|---|---|---|---|---|
| Overall | | 7 (15.6) | 5 (11.1) | 5 (11.1) | 5 (11.4) | 6 (13.6) | 4 (9.1) | 3 (6.7) |
| Cardiac disorders | Overall | 0 (0.0) | 1 (2.2) | 0 (0.0) | 0 (0.0) | 0 (0.0) | 1 (2.3) | 1 (2.2) |
| | Supraventricular extrasystoles | 0 (0.0) | 1 (2.2) | 0 (0.0) | 0 (0.0) | 0 (0.0) | 0 (0.0) | 1 (2.2) |
| | Atrioventricular block first degree | 0 (0.0) | 0 (0.0) | 0 (0.0) | 0 (0.0) | 0 (0.0) | 1 (2.3) | 0 (0.0) |
| Eye disorders | Overall | 1 (2.2) | 0 (0.0) | 0 (0.0) | 0 (0.0) | 0 (0.0) | 0 (0.0) | 0 (0.0) |
| | Dry eye | 1 (2.2) | 0 (0.0) | 0 (0.0) | 0 (0.0) | 0 (0.0) | 0 (0.0) | 0 (0.0) |
| Gastrointestinal disorders | Overall | 1 (2.2) | 0 (0.0) | 0 (0.0) | 0 (0.0) | 0 (0.0) | 0 (0.0) | 0 (0.0) |
| | Nausea | 1 (2.2) | 0 (0.0) | 0 (0.0) | 0 (0.0) | 0 (0.0) | 0 (0.0) | 0 (0.0) |
| General disorders and administration site conditions | Overall | 7 (15.6) | 4 (8.9) | 4 (8.9) | 5 (11.4) | 6 (13.6) | 3 (6.8) | 3 (6.7) |
| | Application site dermatitis | 2 (4.4) | 3 (6.7) | 1 (2.2) | 0 (0.0) | 0 (0.0) | 1 (2.3) | 0 (0.0) |
| | Application site papules | 2 (4.4) | 0 (0.0) | 2 (4.4) | 0 (0.0) | 2 (4.5) | 0 (0.0) | 0 (0.0) |
| | Application site pruritus | 1 (2.2) | 1 (2.2) | 0 (0.0) | 0 (0.0) | 2 (4.5) | 1 (2.3) | 0 (0.0) |
| | Application site pain | 1 (2.2) | 0 (0.0) | 1 (2.2) | 1 (2.3) | 1 (2.3) | 1 (2.3) | 1 (2.2) |
| | Application site erythema | 1 (2.2) | 0 (0.0) | 1 (2.2) | 0 (0.0) | 0 (0.0) | 1 (2.3) | 2 (4.4) |
| | Application site acne | 1 (2.2) | 0 (0.0) | 0 (0.0) | 3 (6.8) | 0 (0.0) | 1 (2.3) | 1 (2.2) |
| | Application site paraesthesia | 1 (2.2) | 0 (0.0) | 0 (0.0) | 0 (0.0) | 2 (4.5) | 0 (0.0) | 0 (0.0) |
| | Application site dryness | 1 (2.2) | 0 (0.0) | 0 (0.0) | 0 (0.0) | 0 (0.0) | 0 (0.0) | 0 (0.0) |
| | Application site perspiration | 0 (0.0) | 0 (0.0) | 0 (0.0) | 1 (2.3) | 0 (0.0) | 0 (0.0) | 0 (0.0) |
| | Application site warmth | 0 (0.0) | 0 (0.0) | 0 (0.0) | 0 (0.0) | 1 (2.3) | 0 (0.0) | 0 (0.0) |
| | Application site irritation | 0 (0.0) | 0 (0.0) | 0 (0.0) | 0 (0.0) | 0 (0.0) | 0 (0.0) | 1 (2.2) |

TABLE 6-3-continued

All Treatment-related Treatment-emergent Adverse Events (Safety Population)

| System Organ Class | Preferred Term | | | | | | |
|---|---|---|---|---|---|---|---|
| Investigations | Overall | 1 (2.2) | 1 (2.2) | 1 (2.2) | 0 (0.0) | 0 (0.0) | 1 (2.3) | 0 (0.0) |
| | Electro-cardiogram T wave inversion | 1 (2.2) | 0 (0.0) | 1 (2.2) | 0 (0.0) | 0 (0.0) | 0 (0.0) | 0 (0.0) |
| | Electro-cardiogram T wave amplitude decreased | 0 (0.0) | 1 (2.2) | 0 (0.0) | 0 (0.0) | 0 (0.0) | 0 (0.0) | 0 (0.0) |
| | Electro-cardiogram T wave biphasic | 0 (0.0) | 0 (0.0) | 0 (0.0) | 0 (0.0) | 0 (0.0) | 1 (2.3) | 0 (0.0) |
| Nervous system disorders | Overall | 2 (4.4) | 0 (0.0) | 0 (0.0) | 0 (0.0) | 0 (0.0) | 0 (0.0) | 0 (0.0) |
| | Headache | 2 (4.4) | 0 (0.0) | 0 (0.0) | 0 (0.0) | 0 (0.0) | 0 (0.0) | 0 (0.0) |
| Skin and subcutaneous tissue disorders | Overall | 0 (0.0) | 0 (0.0) | 1 (2.2) | 0 (0.0) | 0 (0.0) | 0 (0.0) | 0 (0.0) |
| | Skin lesion | 0 (0.0) | 0 (0.0) | 1 (2.2) | 0 (0.0) | 0 (0.0) | 0 (0.0) | 0 (0.0) |
| Vascular disorders | Overall | 0 (0.0) | 1 (2.2) | 0 (0.0) | 0 (0.0) | 0 (0.0) | 0 (0.0) | 0 (0.0) |
| | Hypertension | 0 (0.0) | 1 (2.2) | 0 (0.0) | 0 (0.0) | 0 (0.0) | 0 (0.0) | 0 (0.0) |

| | | Number (%) of Patients | | | | | |
|---|---|---|---|---|---|---|---|
| System Organ Class | Preferred Term | Vehicle QD (N = 44) | Total Oxy BID (N = 135) | Total Oxy QD (N = 133) | Total Oxy (N = 268) | Total Vehicle (N = 88) | Total (N = 356) |
| Overall | | 0 (0.0) | 17 (12.6) | 13 (9.8) | 30 (11.2) | 5 (5.7) | 35 (9.8) |
| Cardiac disorders | Overall | 0 (0.0) | 1 (0.7) | 2 (1.5) | 3 (1.1) | 0 (0.0) | 3 (0.8) |
| | Supraventricular extrasystoles | 0 (0.0) | 1 (0.7) | 1 (0.8) | 2 (0.7) | 0 (0.0) | 2 (0.6) |
| | Atrioventricular block first degree | 0 (0.0) | 0 (0.0) | 1 (0.8) | 1 (0.4) | 0 (0.0) | 1 (0.3) |
| Eye disorders | Overall | 0 (0.0) | 1 (0.7) | 0 (0.0) | 1 (0.4) | 0 (0.0) | 1 (0.3) |
| | Dry eye | 0 (0.0) | 1 (0.7) | 0 (0.0) | 1 (0.4) | 0 (0.0) | 1 (0.3) |
| Gastrointestinal disorders | Overall | 0 (0.0) | 1 (0.7) | 0 (0.0) | 1 (0.4) | 0 (0.0) | 1 (0.3) |
| | Nausea | 0 (0.0) | 1 (0.7) | 0 (0.0) | 1 (0.4) | 0 (0.0) | 1 (0.3) |
| General disorders and administration site conditions | Overall | 0 (0.0) | 15 (11.1) | 12 (9.0) | 27 (10.1) | 5 (5.7) | 32 (9.0) |
| | Application site dermatitis | 0 (0.0) | 6 (4.4) | 1 (0.8) | 7 (2.6) | 0 (0.0) | 7 (2.0) |
| | Application site papules | 0 (0.0) | 4 (3.0) | 2 (1.5) | 6 (2.2) | 0 (0.0) | 6 (1.7) |
| | Application site pruritus | 0 (0.0) | 2 (1.5) | 3 (2.3) | 5 (1.9) | 0 (0.0) | 5 (1.4) |
| | Application site pain | 0 (0.0) | 2 (1.5) | 3 (2.3) | 5 (1.9) | 1 (1.1) | 6 (1.7) |
| | Application site erythema | 0 (0.0) | 2 (1.5) | 3 (2.3) | 5 (1.9) | 0 (0.0) | 5 (1.4) |
| | Application site acne | 0 (0.0) | 1 (0.7) | 2 (1.5) | 3 (1.1) | 3 (3.4) | 6 (1.7) |
| | Application site paraesthesia | 0 (0.0) | 1 (0.7) | 2 (1.5) | 3 (1.1) | 0 (0.0) | 3 (0.8) |
| | Application site dryness | 0 (0.0) | 1 (0.7) | 0 (0.0) | 1 (0.4) | 0 (0.0) | 1 (0.3) |
| | Application site perspiration | 0 (0.0) | 0 (0.0) | 0 (0.0) | 0 (0.0) | 1 (1.1) | 1 (0.3) |
| | Application site warmth | 0 (0.0) | 0 (0.0) | 1 (0.8) | 1 (0.4) | 0 (0.0) | 1 (0.3) |
| | Application site irritation | 0 (0.0) | 0 (0.0) | 1 (0.8) | 1 (0.4) | 0 (0.0) | 1 (0.3) |
| Investigations | Overall | 0 (0.0) | 3 (2.2) | 1 (0.8) | 4 (1.5) | 0 (0.0) | 4 (1.1) |
| | Electro-cardiogram T wave inversion | 0 (0.0) | 2 (1.5) | 0 (0.0) | 2 (0.7) | 0 (0.0) | 2 (0.6) |
| | Electro-cardiogram T wave amplitude decreased | 0 (0.0) | 1 (0.7) | 0 (0.0) | 1 (0.4) | 0 (0.0) | 1 (0.3) |
| | Electro-cardiogram T wave biphasic | 0 (0.0) | 0 (0.0) | 1 (0.8) | 1 (0.4) | 0 (0.0) | 1 (0.3) |
| Nervous system disorders | Overall | 0 (0.0) | 2 (1.5) | 0 (0.0) | 2 (0.7) | 0 (0.0) | 2 (0.6) |
| | Headache | 0 (0.0) | 2 (1.5) | 0 (0.0) | 2 (0.7) | 0 (0.0) | 2 (0.6) |
| Skin and subcutaneous tissue disorders | Overall | 0 (0.0) | 1 (0.7) | 0 (0.0) | 1 (0.4) | 0 (0.0) | 1 (0.3) |
| | Skin lesion | 0 (0.0) | 1 (0.7) | 0 (0.0) | 1 (0.4) | 0 (0.0) | 1 (0.3) |

TABLE 6-3-continued

| | All Treatment-related Treatment-emergent Adverse Events (Safety Population) | | | | | | | |
|---|---|---|---|---|---|---|---|---|
| Vascular | Overall | 0 (0.0) | 1 (0.7) | 0 (0.0) | 1 (0.4) | 0 (0.0) | 1 (0.3) |
| disorders | Hypertension | 0 (0.0) | 1 (0.7) | 0 (0.0) | 1 (0.4) | 0 (0.0) | 1 (0.3) |

BID = twice daily;
Oxy = oxymetazoline hydrochloride;
QD = once daily
Note:
Treatment-emergent adverse events include all reported events that began during the study or increased in severity compared with baseline. Treatment-related adverse events include those that in the investigator's opinion may have been caused by the study medication with reasonable possibility. Within each preferred term, a patient is counted at most once.

6.2.3.2 Treatment-Related Application Site Adverse Events

This section summarizes application site adverse events that, in the investigator's opinion, may have been caused by the study medication.

Treatment-related application site adverse events were reported in 28 oxymetazoline-treated patients (7 Oxy 1.5% BID, 4 Oxy 1.0% BID, 5 Oxy 0.5% BID, 6 Oxy 1.5% QD, 3 Oxy 1.0% QD, and 3 Oxy 0.5% QD) and 5 vehicle-treated patients. These events included application site dermatitis, application site erythema, application site pruritus, application site pain (burning), application site paresthesia, application site warmth, application site papules, application site irritation, application site acne, application site dryness, application site perspiration, and skin lesion. A tabular listing of these patients is provided in Table 6-4.

A majority of the events were mild or moderate in severity and resolved without sequelae; only 4 of these events were ongoing at study exit. A total of 7 severe events occurred in 3 Oxy-treated patients; these included severe dermatitis in 1 patient treated with Oxy 1.0% BID; severe pruritus, erythema, and pain (ie, burning) in 1 patient treated with Oxy 1.0% QD; and severe pain (ie, burning), irritation, and erythema in 1 patient treated with Oxy 0.5% QD (patient discontinued from the study).

Seven patients (all treated with oxymetazoline) discontinued from the study due to treatment-related application site adverse events (Table 6-4). All of these events resolved without sequelae upon discontinuation of study treatment.

TABLE 6-4

| Patients with Treatment-related Application Site Adverse Events (Safety Population) | | | | | | | |
|---|---|---|---|---|---|---|---|
| Patient Number | Age/ Sex/ Race[a] | Preferred Term (Investigator Term) | Onset Day/ Duration[b] | Severity Onset/ Maximum | Serious Adverse Event? | Resulted in Study/Treatment Discontinuation? | Outcome |
| Oxy 1.5% BID Treatment Group | | | | | | | |
| 10001-1003 | 53/F/C | Application site paraesthesia (Tingling at application site) | 2/20 | Mild/Mild | No | No | Resolved without sequelae |
| 10011-1236 | 54/F/C | Application site pain (Facial stinging at application site) | 2/3 | Mild/Mild | No | No | Resolved without sequelae |
| 10012-1078 | 36/F/H | Application site pruritus (Itching at application site) | 2/4 | Mild/Moderate | No | Yes | Resolved without sequelae |
| | | Application site erythema (Erythema [irritant reaction] in site of study drug) | 3/3 | Mild/Moderate | No | Yes | Resolved without sequelae after treatment with topical fluocinonide |
| | | Application site dermatitis (Sandpaper type rash = irritant dermatitis in the study medication application site of the face) | 3/3 | Mild/Moderate | No | Yes | Resolved without sequelae after treatment with topical fluocinonide |
| | | Application site acne (Closed comedones, white heads on study medication site of the face) | 3/3 | Mild/Moderate | No | Yes | Resolved without sequelae after treatment with topical fluocinonide |
| 10012-1508 | 36/F/H | Application site papules (Papules at application site) | 4/13 | Mild/Mild | No | No | Resolved without sequelae |
| 10013-1168 | 48/F/C | Application site dermatitis (Contact dermatitis face application site) | 7/8 | Mild/Moderate | No | Yes | Resolved with sequelae after treatment with topical hydrocortisone |
| 10016-1296 | 48/F/C | Application site dryness (Facial dryness at application site) | 20/16 | Mild/Mild | No | No | Resolved without sequelae |
| 10016-1401 | 50/F/C | Application site papules (Worsening of facial papules at application site) | 3/35 | Mild/Mild | No | No | Resolved without sequelae |
| Oxy 1.0% BID Treatment Group | | | | | | | |
| 10012-1440 | 54/M/C | Application site pruritus (Itching on forehead after application of study product) | 6/8 | Mild/Mild | No | No | Resolved without sequelae |
| 10014-1200 | 38/F/C | Application site dermatitis (Contact dermatitis - face treatment area) | 3/8 | Moderate/ Severe | No | Yes | Resolved without sequelae after treatment with oral diphenhydramine and topical triamcinolone |

TABLE 6-4-continued

Patients with Treatment-related Application Site Adverse Events (Safety Population)

| Patient Number | Age/ Sex/ Race[a] | Preferred Term (Investigator Term) | Onset Day/ Duration[b] | Severity Onset/ Maximum | Serious Adverse Event? | Resulted in Study/Treatment Discontinuation? | Outcome |
|---|---|---|---|---|---|---|---|
| 10017-1193 | 51/F/C | Application site dermatitis (Contact dermatitis to the application site) | 3/3 | Moderate/ Moderate | No | Yes | Resolved without sequelae after treatment with oral diphenhydramine |
| 10017-1305 | 44/F/C | Application site dermatitis (Contact dermatitis at application site) | 7/23 | Moderate/ Moderate | No | Yes | Resolved without sequelae after treatment with topical hydrocortisone |
| Oxy 0.5% BID Treatment Group | | | | | | | |
| 10002-1012 | 38/F/C | Skin lesion (Increased number of inflammatory lesions on the face [in the application area]) | 1/2 | Mild/Mild | No | No | Resolved without sequelae |
| 10012-1079 | 60/F/H | Application site papules (Papules on drug application site) | 8/23 | Mild/Mild | No | No | Resolved without sequelae |
| 10012-1158 | 27/F/H | Application site papules (Papular dermatitis on forehead - drug application site) | 2/18 | Mild/Mild | No | No | Resolved without sequelae |
| 10013-1353 | 23/F/C | Application site dermatitis (Contact dermatitis - face application site) | 6/10 | Mild/Mild | No | No | Resolved without sequelae |
| 10016-1391 | 50/F/C | Application site erythema (Worsening of facial erythema at application site) | 4/29 | Mild/Mild | No | No | Resolved without sequelae |
| | | Application site pain (Burning when applying IP [treatment area]) | 4/26 | Mild/Mild | No | No | Resolved without sequelae |
| Oxy 1.5% QD Treatment Group | | | | | | | |
| 10001-1332 | 76/M/C | Application site paraesthesia (Tingling, face [cheeks] at application site) | 2/13 | Mild/Mild | No | No | Resolved without sequelae |
| 10012-1146 | 23/F/H | Application site papules (Worsening of papules - on study drug application site of face) | 43/NA | Moderate/ Moderate | No | No | Ongoing at study exit |
| 10002-1188 | 42/F/C | Application site pruritus (Pruritus on face [on the treatment area]) | 5/16 | Moderate/ Moderate | No | No | Resolved without sequelae |
| 10013-1184 | 41/F/C | Application site pruritus (Itching at application site) | 14/1 | Moderate/ Moderate | No | No | Resolved without sequelae |
| | | Application site pain (Burning at application site) | 14/1 | Mild/Mild | No | No | Resolved without sequelae |
| | | Application site warmth (Warm sensation to face at application site) | 15/1 | Mild/Mild | No | No | Resolved without sequelae |
| 10013-1250 | 53/F/C | Application site paraesthesia (Tingling sensation to face application site) | 3/12 | Mild/Mild | No | No | Resolved without sequelae |
| 10017-1427 | 53/F/C | Application site papules (Increased papules to face at application site) | 15/15 | Mild/Mild | No | No | Resolved without sequelae |
| Oxy 1.0% QD Treatment Group | | | | | | | |
| 10011-1249 | 52/F/C | Application site acne (Acne at application site) | 9/9 | Mild/Mild | No | No | Resolved without sequelae |
| 10012-1167 | 63/M/C | Application site pruritus (Pruritus at application site) | 2/3 | Mild/Severe | No | No | Resolved without sequelae |
| | | Application site erythema (Erythema at application site) | 2/3 | Mild/Severe | No | No | Resolved without sequelae |
| | | Application site pain (Burning at application site) | 2/3 | Mild/Severe | No | No | Resolved without sequelae |
| 10013-1237 | 60/F/C | Application site dermatitis (Contact dermatitis face application site) | 4/7 | Mild/Mild | No | Yes | Resolved without sequelae |
| Oxy 0.5% QD Treatment Group | | | | | | | |
| 10001-1048 | 38/F/C | Application site acne (Facial acne - at application site) | 8/NA | Mild/Moderate | No | No | Ongoing at study exit |
| 10012-1073 | 56/M/C | Application site pain (Burning sensation in application site of study drug) | 6/3 | Severe/Severe | No | Yes | Resolved without sequelae |
| | | Application site irritation (Irritation in application site of study drug) | 6/3 | Severe/Severe | No | Yes | Resolved without sequelae |
| | | Application site erythema (Erythema in application site of study drug) | 6/3 | Severe/Severe | No | Yes | Resolved without sequelae |

TABLE 6-4-continued

Patients with Treatment-related Application Site Adverse Events (Safety Population)

| Patient Number | Age/ Sex/ Race[a] | Preferred Term (Investigator Term) | Onset Day/ Duration[b] | Severity Onset/ Maximum | Serious Adverse Event? | Resulted in Study/Treatment Discontinuation? | Outcome |
|---|---|---|---|---|---|---|---|
| 10012-1345 | 52/F/C | Application site erythema (Rebound redness at application site 10 hours postdose) | 8/25 | Moderate/ Moderate | No | No | Resolved without sequelae |
| Vehicle Treatment | | | | | | | |
| 10001-1310 | 56/F/C | Application site pain (Stinging/burning, face at application site) | 3/1 | Moderate/ Moderate | No | No | Resolved without sequelae |
| 10004-1240 | 53/F/C | Application site perspiration (Facial sweating [at application site]) | 15/15 | Mild/Mild | No | No | Resolved without sequelae |
| 10005-1308 | 23/F/C | Application site acne (Acne involving site/area of medication application) | 15/NA | Mild/Mild | No | No | Ongoing at study exit |
| 10008-1364 | 63/M/C | Application site acne (Acne - forehead; treatment area) | 15/NA | Moderate/ Moderate | No | No | Ongoing at study exit |
| 10012-1147 | 48/F/H | Application site acne (Acne - inflammatory lesions at application site) | 1/29 | Mild/Mild | No | No | Resolved without sequelae |

BID = twice daily;
C = Caucasian;
F = female;
H = Hispanic;
M = male;
NA = not applicable;
Oxy = oxymetazoline hydrochloride;
QD = once daily
[a] Age in years
[b] Onset Day = Number of days since the first dose of study medication. Duration = Number of days the adverse event lasted.

6.2.4 Subgroup Analyses of Adverse Events

The incidence of TEAEs was analyzed by age group (<45, 45 to 64, and ≥65 years of age) and sex (male versus female).

The overall incidence of TEAEs was similar across the Oxy and vehicle treatment groups following twice-daily and once-daily dosing for the age groups of <45 years and 45 to 64 years.

There were too few patients in the age group of ≥65 years to provide any meaningful conclusions.

The overall incidence of TEAEs was similar across the Oxy and vehicle treatment groups following twice-daily and once-daily dosing for both males and females.

6.3 Deaths, Other Serious Adverse Events, and Other Significant Adverse Events 6.3.1 Deaths There were no deaths reported in this study.

6.3.2 Other Serious Adverse Events

There were 5 serious adverse events reported in 3 patients during the study: 1 event in 1 patient in the Oxy 1.0% BID group, 1 event in 1 patient in the Oxy 1.0% QD group, and 3 events in 1 patient in the vehicle QD group. None of these was considered to be related to study treatment. Serious adverse events that occurred in 1 patient in the vehicle group led to study discontinuation. Brief summaries of these cases are provided below.

Patient 10015-1270, a 50-year-old Caucasian female randomized to the Oxy 1.0% BID treatment group, experienced a serious adverse event of cerebrovascular accident on day 29 of study drug administration. The patient had slurred speech and memory fuzziness starting on day 29. Her symptoms improved in 24 hours however, she didn't feel right during the following week. On day 39, the patient was hospitalized with a diagnosis of cerebrovascular accident. She was treated the next day with acetylsalicylic acid and simvastatin. The patient was discharged the same day with resolution of the cerebrovascular accident with sequelae of memory changes. The adverse event was considered to be mild in severity, not considered to be related to study medication, and did not result in study discontinuation.

Patient 10012-1167, a 63-year-old Caucasian male with a medical history of left anterior cruciate ligament (ACL) injury and ACL surgery, was randomized to the Oxy 1.0% QD group. The patient experienced a serious adverse event of chondrocalcinosis pyrophosphate (pseudogout) in the left knee on posttreatment day 42. The subject had surgery on his left knee 2 days later, and was administered methylprednisolone sodium succinate for swelling, and further treatment with oral prednisone. The patient was discharged the next day with resolution without sequelae of the chondrocalcinosis pyrophosphate. The adverse event was considered to be mild to moderate in severity, not considered to be related to study medication, and did not result in study discontinuation.

Patient 10001-1052, a 66-year-old Caucasian female with a medical history of right rotator cuff pain, was randomized to the vehicle QD group. She experienced the serious adverse events of rotator cuff syndrome on day 19 and hypertension and congestive heart failure on day 23. The patient was hospitalized on day 22 for surgical repair of the worsening right rotator cuff pain. After surgery, her blood pressure increased to 140/70 mm Hg, and she was tachypneic and hypoxic. She was immediately admitted to the heart failure service and was placed on positive pressure ventilator. She was diagnosed with hypertension and congestive heart failure believed to be due to fluid overload during the surgery. The hypertension improved during her admission and she was normotensive at discharge. All 3 events were not considered to be related to study medication, resulted in study discontinuation, and resolved without sequelae within 6 days.

6.3.3 Discontinuations Due to Adverse Events

A total of 10 of the 356 enrolled patients (2.8%) discontinued the treatment and study due to adverse events: 8 patients treated with oxymetazoline (2 Oxy 1.5% BID, 3 Oxy 1.0% BID, and 1 each in the Oxy 0.5% BID, Oxy 1.0% QD, and Oxy 0.5% QD treatment groups) and 2 patients treated with vehicle.

The most frequently reported adverse events leading to treatment/study discontinuation were application site adverse events; all of these events occurred in 7 Oxy-treated patients and were considered by the investigator to be treatment-related. These events included application site dermatitis, application site acne, application site erythema, application site pruritus, application site irritation, and application site pain; see Section 6.2.3.2 for further details.

Non-application site adverse events leading to treatment/study discontinuation were reported in 5 patients (3 Oxy-treated and 2 vehicle-treated patients [some of these patients also reported application site events leading to discontinuation]). These events included cardiac failure congestive, dry eye, nausea, irritable bowel syndrome, weight decreased, blood pressure increased, rotator cuff syndrome, headache, and hypertension.

One patient (10001-1052 [in the vehicle group]) had serious adverse events that led to study discontinuation; this patient is summarized in Section 6.3.2.

6.4 Clinical Laboratory Evaluation

Laboratory data for each patient were collected, along with the normal ranges for each laboratory test. These listings also identify patients with laboratory values that were abnormal. An abnormal laboratory value was defined as one that was higher or lower than the normal range.

For each laboratory test, individual patient changes were evaluated using shift tables. These tables include the number of patients whose test values changed from normal, low, or high (relative to the normal range) at baseline to normal, low, or high at each follow-up assessment. Laboratory evaluations are presented in the sections below.

A total of 7 patients had adverse events that were considered to be related to laboratory variables. These included: increased alanine aminotransferase in 2 patients in the Oxy 1.5% BID group; anemia in 2 patients in the Oxy 1.0% BID group; hyperkalemia in 1 patient in the Oxy 1.0% BID group; hyperglycemia in 1 patient in the Oxy 1.5% QD group; and hematuria in 1 patient in the Oxy 1.0% QD group. All of these events were mild in severity, not considered to be treatment-related, and did not result in study discontinuation.

6.4.1 Hematology 6.4.1.1 Laboratory Values Over Time

Mean laboratory values for hematology variables at baseline were similar among the treatment groups. Mean changes from baseline at days 29 and 56/exit were small and not considered to be clinically relevant.

6.4.1.2 Individual Patient Changes

Most patients had normal hematology values at baseline and days 29 and 56/exit. Shift tables of hematology variables were made. A few individual patients had values that shifted from normal to abnormal (out of reference range values) in most treatment groups at days 29 and 56/exit, but no clinically relevant trends were noted for these shifts.

6.4.1.3 Individual Clinically Significant Abnormalities

A by-patient listing of abnormal hematology values, defined as any values outside the reference range, was made.

6.4.2 Chemistry 6.4.2.1 Laboratory Values Over Time

Mean laboratory values for chemistry variables at baseline were similar among the treatment groups. Mean changes from baseline at days 29 and 56/exit were small and not considered to be clinically relevant.

6.4.2.2 Individual Patient Changes

Most patients had normal chemistry values at baseline and days 29 and 56/exit. Shift tables of chemistry variables were made. A few individual patients had values that shifted from normal to abnormal (out of reference range values) in most treatment groups at days 29 and 56/exit, but no clinically relevant trends were noted for these shifts.

6.4.2.3 Individual Clinically Significant Abnormalities

A by-patient listing of abnormal chemistry values, defined as any values outside the reference range, was made.

6.4.3 Urinalysis 6.4.3.1 Laboratory Values Over Time

Mean laboratory values for urinalysis variables at baseline were similar among the treatment groups. Mean changes from baseline at days 29 and 56/exit were small and not considered to be clinically relevant.

6.4.3.2 Individual Patient Changes

Most patients had normal urinalysis values at baseline and days 29 and 56/exit. Shift tables of urinalysis variables were made. A few individual patients had values that shifted from normal to abnormal (out of reference range values) in most treatment groups at days 29 and 56/exit, but no clinically relevant trends were noted for these shifts.

6.4.3.3 Individual Clinically Significant Abnormalities

A by-patient listing of abnormal urinalysis values, defined as any values outside the reference range, was made.

6.5 Vital Signs, Physical Findings, and Other Observations Related to Safety 6.5.1 Vital Signs Mean systolic blood pressure, diastolic blood pressure, respiratory rate, pulse rate, and body temperature at screening were similar among the treatment groups. There were no clinically relevant differences between the treatment groups in the mean change from study baseline for any of the vital signs variables. Although there were some minor differences in mean values between treatment groups at some visits, there were no signs of any consistent trend from visit to visit and the majority of the observed differences were not considered to be clinically relevant.

6.5.2 Physical Examination

The number of patients with abnormal physical examination findings at screening and study exit were generally similar between the treatment groups for each body system. As expected, a majority of the findings in all treatment groups were coded to SOC of Skin and Subcutaneous Tissue Disorders and included rosacea. No safety concerns were evident from physical examination findings.

6.5.3 Facial Dermal Tolerability

The proportion of patients with at least a 1-grade increase (worsening) in severity for facial dermal tolerability (ie, dryness, scaling, stinging/burning, and pruritus at the application area) from baseline on days 1, 14, and 28 is provided in Table 6-5.

All oxymetazoline doses and vehicle treatments given twice-daily or once-daily were well-tolerated. The proportions of patients with worsening in severity for all 4 tolerability assessments were similar between the Total Oxy groups and the Total Vehicle groups following twice-daily or once-daily dosing on days 1, 14, and 28.

Following twice-daily or once-daily dosing on day 1, the highest proportions of patients in the Total Oxy treatment groups reported a worsening of stinging/burning at the application site (10.4% in the Total Oxy twice-daily group and 12.8% in the Total Oxy once-daily group). Over time on days 14 and 28, the proportions of patients with worsening of stinging/burning decreased to 8.9% and 1.5% in the Total Oxy twice-daily group on days 14 and 28, respectively, and 12.0% and 6.00% in the Total Oxy once-daily group on days 14 and 28, respectively.

TABLE 6-5

Number (%) of Patients with at Least 1-grade Increase (Worsening) in Severity for Dermal Tolerability from Baseline on Days 1, 14, and 28 (Safety Population)

| | | Number (%) of Patients | | | | | | | | | |
|---|---|---|---|---|---|---|---|---|---|---|---|
| | | Twice-daily Dosing | | | | | Once-daily Dosing | | | | |
| Day | Dermal Tolerability | Oxy 1.5% BID (N = 45) | Oxy 1.0% BID (N = 45) | Oxy 0.5% BID (N = 45) | Total Oxy BID (N = 135) | Vehicle BID (N = 44) | Oxy 1.5% QD (N = 44) | Oxy 1.0% QD (N = 44) | Oxy 0.5% QD (N = 45) | Total Oxy QD (N = 133) | Vehicle QD (N = 44) |
| 1 | Dryness | 4 (8.9) | 5 (11.1) | 3 (6.7) | 12 (8.9) | 7 (15.9) | 5 (11.4) | 6 (13.6) | 3 (6.7) | 14 (10.5) | 4 (9.1) |
| | Scaling | 2 (4.4) | 2 (4.4) | 1 (2.2) | 5 (3.7) | 4 (9.1) | 2 (4.5) | 2 (4.5) | 2 (4.4) | 6 (4.5) | 1 (2.3) |
| | Stinging/Burning | 8 (17.8) | 3 (6.7) | 3 (6.7) | 14 (10.4) | 4 (9.1) | 4 (9.1) | 7 (15.9) | 6 (13.3) | 17 (12.8) | 1 (2.3) |
| | Itching (Pruritus) | 4 (8.9) | 5 (11.1) | 3 (6.7) | 12 (8.9) | 2 (4.5) | 4 (9.1) | 3 (6.8) | 7 (15.6) | 14 (10.5) | 3 (6.8) |
| 14 | Dryness | 12 (26.7) | 11 (24.4) | 8 (17.8) | 31 (23.0) | 11 (25.0) | 15 (34.1) | 10 (22.7) | 7 (15.6) | 32 (24.1) | 9 (20.5) |
| | Scaling | 8 (17.8) | 10 (22.2) | 9 (20.0) | 27 (20.0) | 8 (18.2) | 14 (31.8) | 9 (20.5) | 11 (24.4) | 34 (25.6) | 9 (20.5) |
| | Stinging/Burning | 5 (11.1) | 2 (4.4) | 5 (11.1) | 12 (8.9) | 9 (20.5) | 6 (13.6) | 5 (11.4) | 5 (11.1) | 16 (12.0) | 3 (6.8) |
| | Itching (Pruritus) | 8 (17.8) | 7 (15.6) | 9 (20.0) | 24 (17.8) | 6 (13.6) | 9 (20.5) | 9 (20.5) | 4 (8.9) | 22 (16.5) | 7 (15.9) |
| 28 | Dryness | 6 (13.3) | 7 (15.6) | 9 (20.0) | 22 (16.3) | 9 (20.5) | 10 (22.7) | 11 (25.0) | 6 (13.3) | 27 (20.3) | 6 (13.6) |
| | Scaling | 5 (11.1) | 6 (13.3) | 8 (17.8) | 19 (14.1) | 10 (22.7) | 11 (25.0) | 6 (13.6) | 4 (8.9) | 21 (15.8) | 5 (11.4) |
| | Stinging/Burning | 2 (4.4) | 0 (0.0) | 0 (0.0) | 2 (1.5) | 6 (13.6) | 3 (6.8) | 2 (4.5) | 3 (6.7) | 8 (6.0) | 3 (6.8) |
| | Itching (Pruritus) | 1 (2.2) | 4 (8.9) | 9 (20.0) | 14 (10.4) | 3 (6.8) | 5 (11.4) | 5 (11.4) | 1 (2.2) | 11 (8.3) | 8 (18.2) |

BID = twice daily;
Oxy = oxymetazoline hydrochloride;
QD = once daily
Note:
Severity scale: 0 = none, 1 = mild, 2 = moderate, 3 = severe. Timepoints used on day 1 were predose, hours 1, 2, 4, 6, 8, 10, and 12. Baseline was the predose measurement on day 1. At least a 1-grade increase at any timepoint was considered worsening in the tolerability response.

6.5.4 Clinician Telangiectasia Assessment

The CTA was the investigator's assessment of the average overall severity of telangiectasia on the application sites of the patient's face.

Frequency distributions of each CTA response category are provided for days 1, 28, and 56/study exit in Table 6-6, and for other specified timepoints on screening and days 1, 14, 28, 29, 35, and 56/study exit. Frequency distributions of each CTA category were similar across all treatment groups at all specified timepoints. The proportions of patients with moderate telangiectasia (CTA category 3) and severe telangiectasia (CTA category 4) were similar across all treatment groups on day 1 (predose), day 28 (hour 12 postdose), and day 56/exit (posttreatment period), and did not increase over time in any treatment group (Table 6-6). The proportions of patients with severe telangiectasia remained low in each treatment group (ie, <5 patients per group) at most specified timepoints.

TABLE 6-6

Number (%) of Patients in Each Clinical Telangiectasia Assessment Response Category on Days 1, 28, and 56 (Safety Population)

| | | Number (%) of Patients | | | | | | | |
|---|---|---|---|---|---|---|---|---|---|
| | | Twice-daily Dosing | | | | Once-daily Dosing | | | |
| Day | Response | Oxy 1.5% BID (N = 45) | Oxy 1.0% BID (N = 45) | Oxy 0.5% BID (N = 45) | Vehicle BID (N = 44) | Oxy 1.5% QD (N = 44) | Oxy 1.0% QD (N = 44) | Oxy 0.5% QD (N = 45) | Vehicle QD (N = 44) |
| 1 (Predose) | 0 | 7 (15.6) | 5 (11.1) | 4 (8.9) | 3 (6.8) | 5 (11.4) | 6 (13.6) | 1 (2.2) | 3 (6.8) |
| | 1 | 9 (20.0) | 17 (37.8) | 9 (20.0) | 11 (25.0) | 9 (20.5) | 10 (22.7) | 11 (24.4) | 8 (18.2) |
| | 2 | 13 (28.9) | 10 (22.2) | 11 (24.4) | 21 (47.7) | 14 (31.8) | 16 (36.4) | 16 (35.6) | 16 (36.4) |
| | 3 | 16 (35.6) | 9 (20.0) | 19 (42.2) | 7 (15.9) | 12 (27.3) | 11 (25.0) | 15 (33.3) | 11 (25.0) |
| | 4 | 0 (0.0) | 4 (8.9) | 2 (4.4) | 2 (4.5) | 4 (9.1) | 1 (2.3) | 2 (4.4) | 6 (13.6) |
| 28 (Hour 12) | 0 | 7 (15.6) | 7 (15.6) | 7 (15.6) | 8 (18.2) | 7 (15.9) | 6 (13.6) | 4 (8.9) | 5 (11.4) |
| | 1 | 10 (22.2) | 13 (28.9) | 8 (17.8) | 12 (27.3) | 10 (22.7) | 10 (22.7) | 10 (22.2) | 7 (15.9) |

TABLE 6-6-continued

Number (%) of Patients in Each Clinical Telangiectasia Assessment
Response Category on Days 1, 28, and 56 (Safety Population)

| | | Number (%) of Patients | | | | | | | |
|---|---|---|---|---|---|---|---|---|---|
| | | Twice-daily Dosing | | | | Once-daily Dosing | | | |
| Day | Response | Oxy 1.5% BID (N = 45) | Oxy 1.0% BID (N = 45) | Oxy 0.5% BID (N = 45) | Vehicle BID (N = 44) | Oxy 1.5% QD (N = 44) | Oxy 1.0% QD (N = 44) | Oxy 0.5% QD (N = 45) | Vehicle QD (N = 44) |
| | 2 | 15 (33.3) | 15 (33.3) | 15 (33.3) | 13 (29.5) | 17 (38.6) | 17 (38.6) | 19 (42.2) | 20 (45.5) |
| | 3 | 12 (26.7) | 8 (17.8) | 15 (33.3) | 10 (22.7) | 9 (20.5) | 9 (20.5) | 12 (26.7) | 8 (18.2) |
| | 4 | 1 (2.2) | 2 (4.4) | 0 (0.0) | 1 (2.3) | 1 (2.3) | 2 (4.5) | 0 (0.0) | 4 (9.1) |
| 56 (Study Exit) | 0 | 5 (11.1) | 8 (17.8) | 4 (8.9) | 4 (9.1) | 7 (15.9) | 6 (13.6) | 2 (4.4) | 3 (6.8) |
| | 1 | 14 (31.1) | 17 (37.8) | 9 (20.0) | 15 (34.1) | 10 (22.7) | 12 (27.3) | 14 (31.1) | 11 (25.0) |
| | 2 | 14 (31.1) | 12 (26.7) | 16 (35.6) | 19 (43.2) | 18 (40.9) | 15 (34.1) | 18 (40.0) | 14 (31.8) |
| | 3 | 11 (24.4) | 7 (15.6) | 15 (33.3) | 5 (11.4) | 7 (15.9) | 8 (18.2) | 8 (17.8) | 14 (31.8) |
| | 4 | 1 (2.2) | 1 (2.2) | 1 (2.2) | 1 (2.3) | 2 (4.5) | 3 (6.8) | 3 (6.7) | 2 (4.5) |

BID = twice daily;
Oxy = oxymetazoline hydrochloride;
QD = once daily
Note:
The Clinical Telangiectasia Assessment scale: 0 = clear skin with no signs of telangiectasia, 1 = almost clear, a few barely visible telangiectasia, 2 = mild, a few visible telangiectasia, 3 = moderate, with the presence of clearly visible telangiectasia, 4 = severe, with the presence of many visible telangiectasia.

6.5.5 Lesion Count

The mean number of facial lesions was similar across all treatment groups on screening and days 1 (baseline), 14, 28, 35 (posttreatment follow-up), and 56 (study exit). There was no clinically meaningful increase in mean lesion counts over time in any treatment group.

One patient treated with Oxy 1.5% BID experienced an adverse event of "skin lesion". The event was mild in severity and resolved without sequelae in 2 days with no change in study treatment (see Section 6.2.3.2 and Table 6-4).

6.5.6 12-lead Electrocardiogram Assessment

ECGs were performed at screening, day 1, and day 28 using standardized equipment and electrode placement. A qualified third party vendor (ERT) interpreted the ECG results and reported the findings as normal, abnormal, or unable to evaluate.

The analysis showed no ECG effect of 1.5%, 1.0% and 0.5% oxymetazoline topical creams, administered once or twice daily for 28 consecutive days, on ECG intervals and diagnostic abnormalities. Mean, minimum, and maximum values for heart rate, PR interval, QRS interval, and QTcF interval were within the normal physiologic range, and mean, minimum and maximum changes were clinically unremarkable at all timepoints for all treatments. Changes in heart rate and PR interval were consistent with the expected circadian variation. No consistent change was observed for QRS interval, QTcF interval, or diagnostic abnormalities. Given that the ECGs were obtained and analyzed using rigorous centralized ECG methods, it was reasonable to conclude that the doses of topical oxymetazoline used in this study did not cause clinically significant ECG effects.

6.5.7 Pregnancy

No patients became pregnant during the study.

6.6 Safety Conclusions

All 3 doses of oxymetazoline (1.5%, 1.0%, and 0.5%) were well-tolerated after once-daily or twice-daily application for up to 28 consecutive days, with TEAEs reported in 33.1% (118/356) of all patients and treatment-related adverse events reported in 9.8% (35/356) of patients.

- The overall incidences of TEAEs and treatment-related TEAEs were similar across the 3 Oxy twice-daily treatment groups, but slightly higher in the Oxy 1.5% QD group than the Oxy 1.0% and 0.5% QD groups. Most TEAEs were considered to be of mild or moderate severity.
- The most frequently reported TEAEs (in ≥2% of all patients) were headache, application site dermatitis, contact dermatitis, upper respiratory tract infection, application site papules, application site erythema, and application site acne.
- Treatment-related TEAEs were reported in 28 oxymetazoline-treated patients and 5 vehicle-treated patients. The most frequently reported treatment-related TEAEs (in ≥1% of all patients) were application site events, including dermatitis, papules, pain (ie, stinging, burning), erythema, pruritus, and acne. A majority of the events were mild or moderate in severity and resolved without sequelae. Most of these application site events (except 4 cases of acne and papules) were resolved in the 4-week posttreatment follow-up period.
- The most frequently reported non-application site TEAE was headache, which occurred similarly in oxymetazoline-treated patients and vehicle-treated patients (4.9% and 4.5%, respectively).
- A total of 2.8% (10/356) of patients discontinued the study due to TEAEs (8 oxymetazoline-treated patients and 2 vehicle-treated patients), the majority of which were due to application site adverse events, including application site dermatitis, application site acne, application site erythema, application site pruritus, application site irritation, and application site pain.
- There were no deaths reported during the study. There were 5 serious adverse events reported in 3 patients, none of which were considered to be related to study treatment.
- Subgroup analyses demonstrated that the incidence of TEAEs was similar across the age and sex subgroups.
- The proportions of patients with worsening in severity of facial tolerability were similar between oxymetazoline-treated and vehicle-treated patients following twice-daily or once-daily dosing on days 1, 14, and 28, demonstrating that all Oxy treatment groups had an acceptable local tolerability profile.

There were no clinically relevant changes from baseline or differences between treatment groups with respect to laboratory values, vital signs, and physical examination findings.

There was no increase in mean lesion counts or in the proportions of patients with moderate or severe telangiectasia in any of the treatment groups during the study or posttreatment period.

There were no clinically relevant ECG findings observed during the study.

7. Discussion and Overall Conclusions 7.1 Discussion

The primary objective of this multicenter, randomized, double-blind, vehicle-controlled, parallel-group study was to evaluate the safety, efficacy, facial dermal tolerability, and pharmacokinetic profile of oxymetazoline cream 0.5%, 1.0%, and 1.5% compared to vehicle applied topically twice-daily or once-daily in patients with moderate to severe facial erythema associated with rosacea. The primary efficacy endpoint was a composite measure defined as the proportion of patients with at least a 2-grade improvement on both the CEA and SSA from baseline over a 12-hour period measured at hours 2, 4, 6, 8, 10, and 12 on day 28. The secondary efficacy measures included improvements in the composite scores at hours 0.5 and 1.0 on day 28. Key safety data included adverse events, facial tolerability assessments, ECGs, laboratory variables, and vital signs.

A total of 356 patients were randomized into the study and included in the mITT and safety populations. The treatment groups were evenly distributed, with 179 patients receiving twice-daily dosing (135 Oxy and 44 vehicle), and 177 patients receiving once-daily dosing (133 Oxy and 44 vehicle). Patients were well matched between the 8 treatment groups for baseline demographic characteristics with no clinically relevant differences between treatment groups for age, sex, race, weight, and height. The mean age of patients was 50.0 years (range 19 to 79 years), and the majority of patients were female (80.1%) and Caucasian (91.3%).

The primary efficacy variable of the proportions of patients with at least a 2-grade decrease (improvement) from baseline over a 12-hour period for both the CEA and SSA on day 28 indicated that oxymetazoline was significantly more effective than vehicle in reducing the facial erythema associated with rosacea. A statistically significant reduction in facial erythema was demonstrated with the 1.5% and 1.0% doses of oxymetazoline cream following twice-daily dosing, and with the 1.5%, 1.0%, and 0.5% doses of oxymetazoline cream following once-daily dosing, compared with vehicle. The proportions of responders at hour 12 on day 28 following twice-daily dosing were 15.6%, 11.1% and 13.3% with oxymetazoline 1.5%, 1.0%, and 0.5%, respectively, compared to 4.5% with vehicle. The proportions of responders following once-daily dosing were 13.6%, 13.6%, and 13.3% with oxymetazoline 1.5%, 1.0%, and 0.5%, respectively, compared to 2.3% with vehicle.

Statistically significant differences were observed as early as hours 2 and 4 on day 1 for a majority of the oxymetazoline treatment groups compared with vehicle. The response rates observed on day 28 were higher than those observed on day 1 for all oxymetazoline treatment groups, with no tachyphylaxis observed during the study.

twice-daily dosing of oxymetazoline did not provide any significant improvement over once-daily dosing for any of the doses studied. However, a numerically higher response rate was observed for oxymetazoline 1.0% versus 0.5% given once-daily at most timepoints on day 28. The response rate was similar between the oxymetazoline 1.5% and 1.0% doses given once-daily.

Statistically significant erythema reduction (as assessed by the investigator using the CEA scale) was demonstrated by 1-grade and 2-grade improvements in the CEA from baseline on day 28 for the Oxy 1.0% and 0.5% QD treatment groups compared with vehicle. Patient perception of treatment benefit (as assessed by the SSA) was demonstrated by 1-grade and 2-grade improvements in the SSA from baseline on day 28 for the Oxy 1.5%, 1.0% and 0.5% QD treatment groups compared with vehicle.

Oxymetazoline 1.5% and 1.0% given twice-daily and once-daily were significantly more effective than vehicle in reducing the facial redness associated with rosacea, as demonstrated by the proportion of patients with at least a 2-grade improvement from baseline over a 12-hour period on day 28 for both the CEA and SSA-2.

During the 4-week posttreatment period, the proportions of patients with a treatment response in the Oxy treatment groups were greater than or similar to those in the vehicle treatment groups. There was no clinically meaningful aggravation of facial erythema. There were no patients with worsening in CEA, SSA, or SSA-2 during this follow-up period. No patients had rebound or worsening of erythema during the posttreatment period, as defined by a 1-grade worsening from baseline on both the CEA and SSA scales and both the CEA and SSA-2 scales.

Subgroup analyses of the primary efficacy variable demonstrated that treatment with oxymetazoline was efficacious in the reduction of erythema regardless of sex, age, CEA score, or SSA score.

The health outcomes analyses of Symptom Assessment, Impact Assessment, and Satisfaction Assessment suggest appropriate responsiveness to oxymetazoline treatment, with comparable results for the once-daily and twice-daily dosing regimens.

Data indicates that steady state may have been reached after the second and third doses for the once-daily and twice-daily groups, respectively. Steady state systemic exposure of oxymetazoline appeared to increase approximately dose proportionally following dermal administration of 0.5%, 1.0%, and 1.5% oxymetazoline cream. Since oxymetazoline cream was administered twice-daily or once-daily continuously for 28 days, the terminal half-life of oxymetazoline was not able to be assessed in this study. Instead, the mean effective half-life of oxymetazoline was estimated to be between 18 and 28 hours, regardless of once-daily or twice-daily dosing regimens. Drug accumulation was minimal following a once-daily dosing regimen. Increased accumulation was observed in the twice-daily treatment groups, however, the overall systemic exposure was less than 2-fold higher when compared to the once-daily treatment groups. In this study, the pharmacokinetics of oxymetazoline was studied under maximum use conditions with a high dose of 1.5% oxymetazoline, more frequent dosing regimen (twice-daily), and administration to the entire face, representing ~4% body surface area, which is the maximum surface area to be treated for the indication.

The safety and tolerability analysis of oxymetazoline demonstrated that all 3 doses were well tolerated when administered once or twice daily for up to 28 days. The proportions of patients reporting TEAEs and treatment-related TEAEs were similar between the oxymetazoline-treated patients and vehicle-treated patients. The overall incidences were similar across the 3 Oxy twice-daily treatment groups, but slightly higher in the Oxy 1.5% QD group than the Oxy 1.0%, and 0.5% QD groups. Across all treatment groups, the most commonly reported TEAEs (occurring in ≥2% patients overall) included headache, application site dermatitis, contact dermatitis, upper respiratory tract infection, application site papules, application site erythema, and application site acne. Most TEAEs were considered to be of mild or moderate severity, and to be related to study treatment.

The most frequently reported treatment-related TEAEs (reported in >1% of all patients) were application site events including dermatitis, papules, pain (ie, stinging, burning), erythema, pruritus, and acne. These occurred more frequently in oxymetazoline-treated patients. However, no clear dose-response was noted for individual preferred terms. A majority of these events were mild or moderate in severity and resolved without sequelae. There were no deaths reported, and 5 serious adverse events were reported in 3 patients, none of which were considered to be related to study treatment.

The proportions of patients with worsening in severity of facial tolerability were similar between oxymetazoline-treated and vehicle-treated patients following twice-daily or once-daily dosing. No aggravations in telangiectasia or facial lesions were observed in any of the oxymetazoline or vehicle treatment groups during the study or the posttreatment period. There were no clinically relevant differences between treatment groups with respect to laboratory values, vital signs, and physical examination findings. There were no clinically relevant ECG findings.

7.2 Conclusions

This multicenter, randomized, double-blind, vehicle-controlled, parallel-group study demonstrated that oxymetazoline hydrochloride cream at concentrations of 1.5%, 1.0%, and 0.5% given once daily significantly reduced the facial erythema associated with rosacea, as assessed by the investigator using the CEA and by the patient using the SSA. A statistically significant reduction in facial erythema was also demonstrated with the 1.5% and 1.0% doses of oxymetazoline cream following twice-daily dosing (with the second dose administered 6 hours after the first dose); however, no additional treatment benefit was observed with twice-daily dosing over once-daily dosing. All concentrations of oxymetazoline were well tolerated when administered once or twice daily, with the majority of adverse events limited to localized dermatological effects.

The following are non-limiting exemplary embodiments:
1. A method of treating facial erythema associated with rosacea in a patient in need of such treatment, comprising topically administering once daily to the site of erythema on the face of the patient a pharmaceutical composition comprising 0.5%, 1.0% or 1.5% oxymetazoline or a pharmaceutically acceptable salt thereof as the sole active ingredient.
2. The method of embodiment 1, wherein the pharmaceutical composition comprises oxymetazoline hydrochloride as the sole active ingredient.
3. The method of embodiment 1 or 2, wherein the pharmaceutical composition is in a form selected from the group consisting of solutions, gels, lotions, creams, ointments, foams, emulsions, microemulsions, milks, serums, aerosols, sprays, dispersions, microcapsules, vesicles and microparticles thereof.
4. The method of any one of embodiments 1-3, wherein the pharmaceutical composition is in the form of a cream.
5. The method of embodiment 4, wherein the pharmaceutical formulation further comprises methylparaben, propylparaben, phenoxyethanol, sodium citrate, citric acid, disodium edetate, butylated hydroxytoluene, lanolin, medium chain triglycerides, diisopropyl adipate, oleyl alcohol, polyethylene glycol PEG-300, polyethylene glycol PEG-6, polyethylene glycol PEG-32, glycol stearate, cetostearyl alcohol, ceteareth-6, stearyl alcohol, ceteareth-25, and purified water.
6. A method of treating facial erythema associated with rosacea in a patient in need of such treatment, comprising topically administering twice daily to the site of erythema on the face of the patient a pharmaceutical composition comprising 1.0% or 1.5% oxymetazoline or pharmaceutically acceptable salt thereof as the sole active ingredient.
7. The method of embodiment 6, wherein the pharmaceutical composition comprises oxymetazoline hydrochloride as the sole active ingredient.
8. The method of embodiment 6 or 7, wherein the pharmaceutical composition is in a form selected from the group consisting of solutions, gels, lotions, creams, ointments, foams, emulsions, microemulsions, milks, serums, aerosols, sprays, dispersions, microcapsules, vesicles and microparticles thereof.
9. The method of any one of embodiments 6-8, wherein the pharmaceutical composition is in the form of a cream.
10. The method of embodiment 9, wherein the pharmaceutical formulation further comprises methylparaben, propylparaben, phenoxyethanol, sodium citrate, citric acid, disodium edetate, butylated hydroxytoluene, lanolin, medium chain triglycerides, diisopropyl adipate, oleyl alcohol, polyethylene glycol PEG-300, polyethylene glycol PEG-6, polyethylene glycol PEG-32, glycol stearate, cetostearyl alcohol, ceteareth-6, stearyl alcohol, ceteareth-25, and purified water.
11. The method of any one of embodiments 6-10, wherein the second dose is administered about 6 to about 10 hours after the first dose.
12. The method of embodiment 11, wherein the second dose is administered about 6 hours after the first dose.
13. The method of any one of embodiments 1-12, wherein the patient experiences no rebound or worsening of erythema during any period post-treatment.
14. The method of any one of embodiments 1-13, wherein the topical administration is well tolerated by the patient and results in limited systemic exposure of the oxymetazoline or a pharmaceutically acceptable salt thereof.
15. The method of embodiment 14, wherein the limited systemic exposure after 28 days of topical administration is less than about 42 picograms/milliliter when 0.5% oxymetazoline or a pharmaceutically acceptable salt thereof is administered; less than about 66 picograms/milliliter when 1.5% oxymetazoline or a pharmaceutically acceptable salt thereof is administered; or less than about 115 picograms/milliliter when 1.5% oxymetazoline or a pharmaceutically acceptable salt thereof is administered.
16. The method of embodiment 5 or 10, wherein the citric acid is anhydrous.
17. The method of embodiment 5, 10 or 16, wherein the sodium citrate is sodium citrate dihydrate.
18. The method of embodiment 5, 10, 16 or 17, wherein the lanolin is anhydrous.
19. The method of embodiment 5, wherein the pharmaceutical formulation comprises about 0.5% w/w oxymetazoline HCl, about 0.2% w/w methylparaben, about 0.05% w/w propylparaben, about 0.8% w/w phenoxyethanol, about 0.3% w/w sodium citrate dihydrate, about 0.219% w/w anhydrous citric acid, about 0.01% w/w disodium edetate, about 0.05% w/w butylated hydroxytoluene, about 2% w/w anhydrous lanolin, about 7% w/w/ medium chain triglycerides, about 7% w/w diisopropyl adipate, about 7% w/w oleyl alcohol, about 4% w/w polyethylene glycol PEG-300, about 8% w/w polyethylene glycol PEG-6/polyethylene glycol PEG-32/glycol stearate (Tefose-63), about 8% w/w cetostearyl alcohol, about 2% w/w ceteareth-6/stearyl alcohol (Cremophor A6), about 2% w/w ceteareth-25, and purified water (q.s.).

20. The method of embodiment 5 or 10, wherein the pharmaceutical formulation comprises about 1.0% w/w oxymetazoline HCl, about 0.2% w/w methylparaben, about 0.05% w/w propylparaben, about 0.8% w/w phenoxyethanol, about 0.3% w/w sodium citrate dihydrate, about 0.219% w/w anhydrous citric acid, about 0.01% w/w disodium edetate, about 0.05% w/w butylated hydroxytoluene, about 2% w/w anhydrous lanolin, about 7% w/w/ medium chain triglycerides, about 7% w/w diisopropyl adipate, about 7% w/w oleyl alcohol, about 4% w/w polyethylene glycol PEG-300, about 8% w/w polyethylene glycol PEG-6/polyethylene glycol PEG-32/glycol stearate (Tefose-63), about 8% w/w cetostearyl alcohol, about 2% w/w ceteareth-6/stearyl alcohol (Cremophor A6), about 2% w/w ceteareth-25, and purified water (q.s.).

21. The method of embodiment 5 or 10, wherein the pharmaceutical formulation comprises about 1.5% w/w oxymetazoline HCl, about 0.2% w/w methylparaben, about 0.05% w/w propylparaben, about 0.8% w/w phenoxyethanol, about 0.3% w/w sodium citrate dihydrate, about 0.219% w/w anhydrous citric acid, about 0.01% w/w disodium edetate, about 0.05% w/w butylated hydroxytoluene, about 2% w/w anhydrous lanolin, about 7% w/w/ medium chain triglycerides, about 7% w/w diisopropyl adipate, about 7% w/w oleyl alcohol, about 4% w/w polyethylene glycol PEG-300, about 8% w/w polyethylene glycol PEG-6/polyethylene glycol PEG-32/glycol stearate (Tefose-63), about 8% w/w cetostearyl alcohol, about 2% w/w ceteareth-6/stearyl alcohol (Cremophor A6), about 2% w/w ceteareth-25, and purified water (q.s.).

22. A stabilized topical cream formulation comprising about 0.5% w/w oxymetazoline HCl, about 0.2% w/w methylparaben, about 0.05% w/w propylparaben, about 0.8% w/w phenoxyethanol, about 0.3% w/w sodium citrate dihydrate, about 0.219% w/w anhydrous citric acid, about 0.01% w/w disodium edetate, about 0.05% w/w butylated hydroxytoluene, about 2% w/w anhydrous lanolin, about 7% w/w/ medium chain triglycerides, about 7% w/w diisopropyl adipate, about 7% w/w oleyl alcohol, about 4% w/w polyethylene glycol PEG-300, about 8% w/w polyethylene glycol PEG-6/polyethylene glycol PEG-32/glycol stearate (Tefose-63), about 8% w/w cetostearyl alcohol, about 2% w/w ceteareth-6/stearyl alcohol (Cremophor A6), about 2% w/w ceteareth-25, and purified water (q.s.).

23. A stabilized topical cream formulation comprising about 1.0% w/w oxymetazoline HCl, about 0.2% w/w methylparaben, about 0.05% w/w propylparaben, about 0.8% w/w phenoxyethanol, about 0.3% w/w sodium citrate dihydrate, about 0.219% w/w anhydrous citric acid, about 0.01% w/w disodium edetate, about 0.05% w/w butylated hydroxytoluene, about 2% w/w anhydrous lanolin, about 7% w/w/ medium chain triglycerides, about 7% w/w diisopropyl adipate, about 7% w/w oleyl alcohol, about 4% w/w polyethylene glycol PEG-300, about 8% w/w polyethylene glycol PEG-6/polyethylene glycol PEG-32/glycol stearate (Tefose-63), about 8% w/w cetostearyl alcohol, about 2% w/w ceteareth-6/stearyl alcohol (Cremophor A6), about 2% w/w ceteareth-25, and purified water (q.s.).

24. A stabilized topical cream formulation comprising about 1.5% w/w oxymetazoline HCl, about 0.2% w/w methylparaben, about 0.05% w/w propylparaben, about 0.8% w/w phenoxyethanol, about 0.3% w/w sodium citrate dihydrate, about 0.219% w/w anhydrous citric acid, about 0.01% w/w disodium edetate, about 0.05% w/w butylated hydroxytoluene, about 2% w/w anhydrous lanolin, about 7% w/w/ medium chain triglycerides, about 7% w/w diisopropyl adipate, about 7% w/w oleyl alcohol, about 4% w/w polyethylene glycol PEG-300, about 8% w/w polyethylene glycol PEG-6/polyethylene glycol PEG-32/glycol stearate (Tefose-63), about 8% w/w cetostearyl alcohol, about 2% w/w ceteareth-6/stearyl alcohol (Cremophor A6), about 2% w/w ceteareth-25, and purified water (q.s.).

25. A stabilized topical cream formulation consisting essentially of about 0.5% w/w oxymetazoline HCl, about 0.2% w/w methylparaben, about 0.05% w/w propylparaben, about 0.8% w/w phenoxyethanol, about 0.3% w/w sodium citrate dihydrate, about 0.219% w/w anhydrous citric acid, about 0.01% w/w disodium edetate, about 0.05% w/w butylated hydroxytoluene, about 2% w/w anhydrous lanolin, about 7% w/w/ medium chain triglycerides, about 7% w/w diisopropyl adipate, about 7% w/w oleyl alcohol, about 4% w/w polyethylene glycol PEG-300, about 8% w/w polyethylene glycol PEG-6/polyethylene glycol PEG-32/glycol stearate (Tefose-63), about 8% w/w cetostearyl alcohol, about 2% w/w ceteareth-6/stearyl alcohol (Cremophor A6), about 2% w/w ceteareth-25, and purified water (q.s.).

26. A stabilized topical cream formulation consisting essentially of about 1.0% w/w oxymetazoline HCl, about 0.2% w/w methylparaben, about 0.05% w/w propylparaben, about 0.8% w/w phenoxyethanol, about 0.3% w/w sodium citrate dihydrate, about 0.219% w/w anhydrous citric acid, about 0.01% w/w disodium edetate, about 0.05% w/w butylated hydroxytoluene, about 2% w/w anhydrous lanolin, about 7% w/w/ medium chain triglycerides, about 7% w/w diisopropyl adipate, about 7% w/w oleyl alcohol, about 4% w/w polyethylene glycol PEG-300, about 8% w/w polyethylene glycol PEG-6/polyethylene glycol PEG-32/glycol stearate (Tefose-63), about 8% w/w cetostearyl alcohol, about 2% w/w ceteareth-6/stearyl alcohol (Cremophor A6), about 2% w/w ceteareth-25, and purified water (q.s.).

27. A stabilized topical cream formulation consisting essentially of about 1.5% w/w oxymetazoline HCl, about 0.2% w/w methylparaben, about 0.05% w/w propylparaben, about 0.8% w/w phenoxyethanol, about 0.3% w/w sodium citrate dihydrate, about 0.219% w/w anhydrous citric acid, about 0.01% w/w disodium edetate, about 0.05% w/w butylated hydroxytoluene, about 2% w/w anhydrous lanolin, about 7% ww/ medium chain triglycerides, about 7% w/w diisopropyl adipate, about 7% w/w oleyl alcohol, about 4% w/w polyethylene glycol PEG-300, about 8% w/w polyethylene glycol PEG-6/polyethylene glycol PEG-32/glycol stearate (Tefose-63), about 8% w/w cetostearyl alcohol, about 2% w/w ceteareth-6/stearyl alcohol (Cremophor A6), about 2% w/w ceteareth-25, and purified water (q.s.).

28. A stabilized topical cream formulation consisting of about 0.5% w/w oxymetazoline HCl, about 0.2% w/w methylparaben, about 0.05% w/w propylparaben, about 0.8% w/w phenoxyethanol, about 0.3% w/w sodium citrate dihydrate, about 0.219% w/w anhydrous citric acid, about 0.01% w/w disodium edetate, about 0.05% w/w butylated hydroxytoluene, about 2% w/w anhydrous lanolin, about 7% w/w/ medium chain triglycerides, about 7% w/w diisopropyl adipate, about 7% w/w oleyl alcohol, about 4% w/w polyethylene glycol PEG-300, about 8% w/w polyethylene glycol PEG-6/polyethylene glycol PEG-32/glycol stearate (Tefose-63), about 8% w/w cetostearyl alcohol, about 2% w/w ceteareth-6/stearyl alcohol (Cremophor A6), about 2% w/w ceteareth-25, and purified water (q.s.).

29. A stabilized topical cream formulation consisting of about 1.0% w/w oxymetazoline HCl, about 0.2% w/w methylparaben, about 0.05% w/w propylparaben, about 0.8% w/w phenoxyethanol, about 0.3% w/w sodium citrate dihydrate, about 0.219% w/w anhydrous citric acid, about 0.01% w/w disodium edetate, about 0.05% w/w butylated hydroxytoluene, about 2% w/w anhydrous lanolin, about 7% w/w/ medium chain triglycerides, about 7% w/w diisopropyl adipate, about 7% w/w oleyl alcohol, about 4% w/w polyethylene glycol PEG-300, about 8% w/w polyethylene glycol PEG-6/polyethylene glycol PEG-32/glycol stearate (Tefose-63), about 8% w/w cetostearyl alcohol, about 2% w/w ceteareth-6/stearyl alcohol (Cremophor A6), about 2% w/w ceteareth-25, and purified water (q.s.).

30. A stabilized topical cream formulation consisting of about 1.5% w/w oxymetazoline HCl, about 0.2% w/w methylparaben, about 0.05% w/w propylparaben, about 0.8% w/w phenoxyethanol, about 0.3% w/w sodium citrate dihydrate, about 0.219% w/w anhydrous citric acid, about 0.01% w/w disodium edetate, about 0.05% w/w butylated hydroxytoluene, about 2% w/w anhydrous lanolin, about 7% w/w/ medium chain triglycerides, about 7% w/w diisopropyl adipate, about 7% w/w oleyl alcohol, about 4% w/w polyethylene glycol PEG-300, about 8% w/w polyethylene glycol PEG-6/polyethylene glycol PEG-32/glycol stearate (Tefose-63), about 8% w/w cetostearyl alcohol, about 2% w/w ceteareth-6/stearyl alcohol (Cremophor A6), about 2% w/w ceteareth-25, and purified water (q.s.).

31. A stabilized topical cream formulation as described in any one of Tables 1, a, 1b or 1c in Example 1 above.

32. A method of treating facial erythema associated with rosacea in a patient in need of such treatment, comprising topically administering once daily to the site of erythema on the face of the patient a stabilized topical cream formulation comprising 0.5%, 1.0% or 1.5% oxymetazoline HCl as the sole active ingredient, wherein the stabilized topical cream formulation is as described in any one of embodiments 25-31.

33. The method of embodiment 32, wherein the patient experiences no rebound or worsening of erythema during any period post-treatment.

34. The method of embodiment 32 or 33, wherein the topical administration is well tolerated by the patient and results in limited systemic exposure of the oxymetazoline or a pharmaceutically acceptable salt thereof.

35. The method of embodiment 34, wherein the limited systemic exposure after 28 days of topical administration is less than about 42 picograms/milliliter when 0.5% oxymetazoline or a pharmaceutically acceptable salt thereof is administered; less than about 66 picograms/milliliter when 1.5% oxymetazoline or a pharmaceutically acceptable salt thereof is administered; or less than about 115 picograms/milliliter when 1.5% oxymetazoline or a pharmaceutically acceptable salt thereof is administered.

A number of references have been cited, the entire disclosures of which have been incorporated herein in their entirety for all purposes.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

What is claimed is:

1. A method of treating persistent facial erythema associated with rosacea in a female adult human patient in need of such treatment, the method comprising topically administering once daily to one or more sites of erythema on the face of the adult human patient, a pharmaceutical composition comprising 1.0% w/w oxymetazoline hydrochloride as the sole active ingredient, wherein the pharmaceutical composition is a cream.

2. The method of claim 1, wherein the female patient is aged 45 to 64.

3. The method of claim 1, wherein the pharmaceutical composition further comprises methylparaben, propylparaben, phenoxyethanol, sodium citrate, citric acid, disodium edetate, butylated hydroxytoluene, lanolin, medium chain triglycerides, diisopropyl adipate, oleyl alcohol, PEG-300, PEG-6 stearate, PEG-32 stearate, glycol stearate, cetostearyl alcohol, ceteareth-6, stearyl alcohol, ceteareth-25, and purified water.

4. The method of claim 1, wherein the pharmaceutical composition comprises about 1.0% w/w oxymetazoline HCl, about 0.2% w/w methylparaben, about 0.05% w/w propylparaben, about 0.8% w/w phenoxyethanol, about 0.3% w/w sodium citrate dihydrate, about 0.2% w/w anhydrous citric acid, about 0.01% w/w disodium edetate, about 0.05% w/w butylated hydroxytoluene, about 2% w/w anhydrous lanolin, about 7% w/w medium chain triglycerides, about 7% w/w diisopropyl adipate, about 7% w/w oleyl alcohol, about 4% w/w polyethylene glycol PEG-300, about 8% w/w polyethylene glycol PEG-6/polyethylene glycol PEG-32/glycol stearate, about 8% w/w cetostearyl alcohol, about 2% w/w ceteareth-6/stearyl alcohol, about 2% w/w ceteareth-25, and purified water.

5. The method of claim 1, wherein the administering results in an at least 2-grade improvement from baseline on Clinician's Erythema Assessment (CEA) scale, Subject Self-Assessment of Erythema (SSA), or both.

6. The method of claim 1, wherein the administering results in an at least 1-grade improvement from baseline on Clinician's Erythema Assessment (CEA) scale, Subject Self-Assessment of Erythema (SSA), or both.

7. The method of claim 1, wherein the administering once daily for 28 days results in a mean $C_{max}$±standard deviation (SD) of 66.4±67.1 pg/mL in said adult human patient.

8. The method of claim 1, wherein the administering once daily for 28 days results in mean±SD $AUC_{0-24}$ of 1050±992 pg·hr/mL in said adult human patient.

9. The method of claim 1, wherein the administering comprises topically applying a pea sized amount of the pharmaceutical composition to the one or more sites of erythema on the face of the adult human patient.

10. A method of treating persistent facial erythema associated with rosacea in a female adult human patient in need of such treatment, the method comprising topically administering once daily to the face of the adult human patient, a pharmaceutical composition comprising 1.0% w/w oxymetazoline hydrochloride as the sole active ingredient, wherein the pharmaceutical composition is a cream.

11. The method of claim 10, wherein the female patient is aged 45 to 64.

12. The method of claim 10, wherein the topically administering comprises applying a thin layer of said pharmaceutical composition over the entire face avoiding the eyes and lips.

13. The method of claim 10, wherein the pharmaceutical composition further comprises methylparaben, propylparaben, phenoxyethanol, sodium citrate, citric acid, disodium edetate, butylated hydroxytoluene, lanolin, medium chain triglycerides, diisopropyl adipate, oleyl alcohol, PEG-300, PEG-6 stearate, PEG-32 stearate, glycol stearate, cetostearyl alcohol, ceteareth-6, stearyl alcohol, ceteareth-25, and purified water.

14. The method of claim 10, wherein the pharmaceutical composition further comprises about 1.0% w/w oxymetazoline HCl, about 0.2% w/w methylparaben, about 0.05% w/w propylparaben, about 0 8% w/w phenoxyethanol, about 0.3% w/w sodium citrate dihydrate, about 0.2% w/w anhydrous citric acid, about 0.01% w/w disodium edetate, about 0.05% w/w butylated hydroxytoluene, about 2% w/w anhydrous lanolin, about 7% w/w medium chain triglycerides, about 7% w/w diisopropyl adipate, about 7% w/w oleyl alcohol, about 4% w/w polyethylene glycol PEG-300, about 8% w/w polyethylene glycol PEG-6/polyethylene glycol PEG-32/glycol stearate, about 8% w/w cetostearyl alcohol, about 2% w/w ceteareth-6/stearyl alcohol, about 2% w/w ceteareth-25, and purified water.

15. The method of claim 10, wherein the administering results in an at least 2-grade improvement from baseline on Clinician's Erythema Assessment (CEA) scale, Subject Self-Assessment of Erythema (SSA), or both.

16. The method of claim 10, wherein the administering once daily for 28 days results in a mean $C_{max} \pm SD$ of $66.4 \pm 67.1$ pg/mL in the adult patient.

17. The method of claim 10, wherein the administering once daily for 28 days results in a mean $AUC_{0-24} \pm SD$ of $1050 \pm 992$ pg·hr/mL in the adult patient.

\* \* \* \* \*